US011433086B2

(12) United States Patent
Magnani et al.

(10) Patent No.: US 11,433,086 B2
(45) Date of Patent: Sep. 6, 2022

(54) COMBINATION OF T-CELL CHECKPOINT INHIBITORS WITH INHIBITORS OF E-SELECTIN OR CXCR4, OR WITH HETEROBIFUNCTIONAL INHIBITORS OF BOTH E-SELECTIN AND CXCR4

(71) Applicant: GlycoMimetics, Inc., Rockville, MD (US)

(72) Inventors: John L. Magnani, Gaithersburg, MD (US); William E. Fogler, Baltimore, MD (US)

(73) Assignee: GlycoMimetics, Inc., Rockville, MD (US)

(*) Notice: Subject to any disclaimer, the term of this patent is extended or adjusted under 35 U.S.C. 154(b) by 61 days.

(21) Appl. No.: 16/323,685

(22) PCT Filed: Aug. 7, 2017

(86) PCT No.: PCT/US2017/045690
§ 371 (c)(1),
(2) Date: Feb. 6, 2019

(87) PCT Pub. No.: WO2018/031445
PCT Pub. Date: Feb. 15, 2018

(65) Prior Publication Data
US 2019/0201429 A1 Jul. 4, 2019

Related U.S. Application Data

(60) Provisional application No. 62/418,722, filed on Nov. 7, 2016, provisional application No. 62/417,045, filed on Nov. 3, 2016, provisional application No. 62/372,116, filed on Aug. 8, 2016.

(51) Int. Cl.
A61K 31/7034 (2006.01)
C07K 16/28 (2006.01)
A61K 47/61 (2017.01)
A61P 35/00 (2006.01)
A61K 31/197 (2006.01)
A61K 31/395 (2006.01)
A61K 31/69 (2006.01)
A61K 31/702 (2006.01)
A61K 31/7068 (2006.01)
A61K 39/395 (2006.01)
A61K 39/00 (2006.01)

(52) U.S. Cl.
CPC ........ A61K 31/7034 (2013.01); A61K 31/197 (2013.01); A61K 31/395 (2013.01); A61K 31/69 (2013.01); A61K 31/702 (2013.01); A61K 31/7068 (2013.01); A61K 39/3955 (2013.01); A61K 47/61 (2017.08); A61P 35/00 (2018.01); C07K 16/2818 (2013.01); C07K 16/2827 (2013.01); A61K 2039/505 (2013.01); C07K 2317/21 (2013.01); C07K 2317/76 (2013.01)

(58) Field of Classification Search
None
See application file for complete search history.

(56) References Cited

U.S. PATENT DOCUMENTS

| | | | |
|---|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |

(Continued)

FOREIGN PATENT DOCUMENTS

DE 2434953 2/1975
EP 319253 A2 6/1989

(Continued)

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*
Vajdos et al. (J Mol Biol. Jul. 5, 2002;320(2):415-28 ) (Year: 2002).*
Brown et al. (J Immunol. May 1996;156(9):3285-91 ) (Year: 1996).*
Guido et al (Curr Med Chem. 2008; 15(1):37-46) (Year: 2008).*
Clark et al (J. Med. Chem., 2014, 57 (12), pp. 5023-5038) (Year: 2014).*

(Continued)

Primary Examiner — Brian Gangle
Assistant Examiner — Andrea K McCollum
(74) Attorney, Agent, or Firm — Finnegan, Henderson, Farabow, Garrett & Dunner LLP

(57) ABSTRACT

Compositions and methods for the treatment of diseases, disorders, and/or conditions associated with the increased regulatory T lymphocyte cell function, comprising the administration of T-cell checkpoint inhibitors in combination with E-selectin inhibitors, C—X—C Motif Chemokine Receptor 4 (CXCR4) receptor inhibitors, and/or heterobifunctional inhibitors that comprise at least one E-selectin inhibitor linked to at least one CXCR4 receptor inhibitor, are disclosed.

12 Claims, 40 Drawing Sheets

(56) References Cited

U.S. PATENT DOCUMENTS

| | | |
|---|---|---|
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,595,756 A * | 1/1997 | Bally .............. A61K 9/1272 264/4.1 |
| 5,604,207 A | 2/1997 | DeFrees et al. |
| 5,618,785 A | 4/1997 | Heavner et al. |
| 5,622,937 A | 4/1997 | Kogan et al. |
| 5,632,991 A | 5/1997 | Gimbrone, Jr. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |
| 5,658,880 A | 8/1997 | Dasgupta et al. |
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,856,300 A | 1/1999 | Rittershaus et al. |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,043,348 A | 3/2000 | Lawman et al. |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,372,712 B1 | 4/2002 | Briesewitz |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 10/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,125 B2 | 1/2005 | Bistrup et al. |
| 6,872,714 B1 | 3/2005 | Schols |
| 6,875,738 B1 | 4/2005 | Clark-Lewis et al. |
| 6,887,842 B1 | 5/2005 | Briesewitz |
| 6,921,531 B2 | 7/2005 | Briesewitz |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,390,784 B2 | 6/2008 | Briesowitz |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 | 4/2013 | Magnani et al. |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 8,895,510 B2 | 11/2014 | Magnani |
| 8,921,328 B2 | 12/2014 | Ernst et al. |
| 9,109,002 B2 | 8/2015 | Magnani et al. |
| 9,254,322 B2 | 2/2016 | Levesque et al. |
| 9,486,497 B2 | 11/2016 | Levesque et al. |
| 9,534,009 B2 | 1/2017 | Magnani |
| 9,796,745 B2 | 10/2017 | Magnani et al. |
| 9,867,841 B2 | 1/2018 | Magnani |
| 2001/0046970 A1 | 11/2001 | Nagy et al. |
| 2001/0051370 A1 | 12/2001 | Bistrup et al. |
| 2002/0031508 A1 | 3/2002 | Wagner et al. |
| 2002/0040008 A1 | 4/2002 | Wagner et al. |
| 2002/0086356 A1 | 7/2002 | Tuschl et al. |
| 2002/0128225 A1 | 9/2002 | Liu et al. |
| 2002/0132220 A1 | 9/2002 | Berens et al. |
| 2002/0155429 A1 | 10/2002 | Allaway et al. |
| 2002/0164336 A1 | 11/2002 | Harrison et al. |
| 2002/0164748 A1 | 11/2002 | Bistrup et al. |
| 2002/0165178 A1 | 11/2002 | Schetter et al. |

(56) References Cited

U.S. PATENT DOCUMENTS

| | | |
|---|---|---|
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0036560 A1 | 2/2003 | Sonis et al. |
| 2003/0039683 A1 | 2/2003 | Cantrell et al. |
| 2003/0073632 A1 | 4/2003 | Ciaccia et al. |
| 2003/0211078 A1 | 11/2003 | Heavner |
| 2004/0067220 A1 | 4/2004 | Sykes |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0181987 A1 | 8/2005 | Blaszczyk-Thurin et al. |
| 2005/0187171 A1 | 8/2005 | Magnani et al. |
| 2005/0214283 A1 | 9/2005 | Sackstein et al. |
| 2006/0194745 A1 | 8/2006 | Magnani et al. |
| 2006/0217303 A1 | 9/2006 | Kriegler |
| 2006/0264451 A1 | 11/2006 | Shim et al. |
| 2006/0287253 A1 | 12/2006 | Kriegler et al. |
| 2007/0021378 A1 | 1/2007 | Varki et al. |
| 2007/0054870 A1 | 3/2007 | Magnani et al. |
| 2007/0054930 A1 | 3/2007 | Shim et al. |
| 2007/0213278 A1 | 9/2007 | Wong et al. |
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2008/0306098 A1 | 12/2008 | Mutz et al. |
| 2009/0036386 A1 | 2/2009 | Magnani et al. |
| 2009/0053198 A1 | 2/2009 | Sackstein |
| 2009/0054334 A1 | 2/2009 | Mutz et al. |
| 2009/0175792 A1 | 7/2009 | Magnani et al. |
| 2009/0176717 A1 | 7/2009 | Magnani |
| 2009/0253646 A1 | 10/2009 | Magnani |
| 2009/0312278 A1 | 12/2009 | Magnani et al. |
| 2010/0145032 A1 | 6/2010 | Laine et al. |
| 2010/0215575 A1 | 8/2010 | O'Neill et al. |
| 2010/0240773 A1 | 9/2010 | Korzekwa et al. |
| 2010/0292095 A1 | 11/2010 | Laukkanen et al. |
| 2010/0303766 A1 | 12/2010 | Miyaji et al. |
| 2010/0311105 A1 | 12/2010 | Lu et al. |
| 2011/0002881 A1 | 1/2011 | Levesque et al. |
| 2011/0020270 A1 | 1/2011 | Levesque et al. |
| 2011/0142856 A1 | 6/2011 | Kokubo et al. |
| 2011/0229409 A1 | 9/2011 | Ranganathan et al. |
| 2011/0245265 A1 | 10/2011 | Zuk et al. |
| 2011/0251148 A1 | 10/2011 | Magnani et al. |
| 2011/0257380 A1 | 10/2011 | Ernst et al. |
| 2012/0093782 A1 | 4/2012 | Grove et al. |
| 2012/0129712 A1 | 5/2012 | Satomaa et al. |
| 2012/0202762 A1 | 8/2012 | Magnani |
| 2012/0258043 A1 | 10/2012 | Ranganathan et al. |
| 2012/0329755 A1 | 12/2012 | Magnani et al. |
| 2013/0184229 A1 | 7/2013 | Magnani et al. |
| 2013/0261070 A1 | 10/2013 | Magnani et al. |
| 2013/0281646 A1 | 10/2013 | Korzekwa et al. |
| 2013/0331350 A1 | 12/2013 | Ernst et al. |
| 2014/0073594 A1 | 3/2014 | Magnani et al. |
| 2014/0178303 A1 | 6/2014 | Magnani et al. |
| 2015/0051164 A1 | 2/2015 | Magnani |
| 2015/0110808 A1 | 4/2015 | Magnani et al. |
| 2015/0284420 A1 | 10/2015 | Magnani et al. |
| 2016/0145290 A1 | 5/2016 | Magnani et al. |
| 2016/0184339 A1 | 6/2016 | Magnani |
| 2016/0193294 A1 | 7/2016 | Magnani et al. |
| 2016/0243145 A1 | 8/2016 | Magnani et al. |
| 2016/0289257 A1 | 10/2016 | Magnani et al. |
| 2016/0333043 A1 | 11/2016 | Magnani et al. |

FOREIGN PATENT DOCUMENTS

| | | |
|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| JP | 2009-507031 | 2/2009 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/25043 | 11/1994 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 95/31210 | 11/1995 |
| WO | WO 96/20204 | 7/1996 |
| WO | WO 96/25418 | 8/1996 |
| WO | WO 96/26950 | 9/1996 |
| WO | WO 96/40942 | 12/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 98/046771 | 10/1998 |
| WO | WO 99/42130 | 8/1999 |
| WO | WO 99/43353 | 9/1999 |
| WO | WO 99/43356 | 9/1999 |
| WO | WO 99/065712 | 12/1999 |
| WO | WO 00/02870 | 1/2000 |
| WO | WO 00/050032 | 8/2000 |
| WO | WO 00/066112 | 11/2000 |
| WO | WO 01/89564 | 11/2001 |
| WO | WO 02/22820 | 3/2002 |
| WO | WO 02/062810 | 8/2002 |
| WO | WO 03/032925 | 4/2003 |
| WO | WO 03/055876 | 7/2003 |
| WO | WO 03/088980 | 10/2003 |
| WO | WO 03/097658 | 11/2003 |
| WO | WO 04/004636 | 1/2004 |
| WO | WO 04/033663 | 4/2004 |
| WO | WO 04/058304 | 7/2004 |
| WO | WO 04/094619 | 11/2004 |
| WO | WO 05/016349 | 2/2005 |
| WO | WO 05/046597 | 5/2005 |
| WO | WO 05/046997 | 5/2005 |
| WO | WO 05/051920 | 6/2005 |
| WO | WO 05/054264 | 6/2005 |
| WO | WO 05/058934 | 6/2005 |
| WO | WO 05/085219 | 9/2005 |
| WO | WO 05/116088 | 12/2005 |
| WO | WO 06/017180 | 2/2006 |
| WO | WO 06/022454 | 3/2006 |
| WO | WO 06/062946 | 6/2006 |
| WO | WO 06/074426 | 7/2006 |
| WO | WO 06/074428 | 7/2006 |
| WO | WO 06/089106 | 8/2006 |
| WO | WO 06/127906 | 11/2006 |
| WO | WO 07/021721 | 2/2007 |
| WO | WO 07/022089 | 2/2007 |
| WO | WO 07/022385 | 2/2007 |
| WO | WO 07/028050 | 3/2007 |
| WO | WO 07/033329 | 3/2007 |
| WO | WO 08/008852 | 1/2008 |
| WO | WO 08/008854 | 1/2008 |
| WO | WO 08/011094 | 1/2008 |
| WO | WO 08/060378 | 5/2008 |
| WO | WO 08/100453 | 8/2008 |
| WO | WO 08/109154 | 9/2008 |
| WO | WO 09/011889 | 1/2009 |

(56) References Cited

FOREIGN PATENT DOCUMENTS

| | | |
|---|---|---|
| WO | WO 09/073911 | 6/2009 |
| WO | WO 09/073916 | 6/2009 |
| WO | WO 09/126556 | 10/2009 |
| WO | WO 09/152245 | 12/2009 |
| WO | WO 10/126888 | 11/2010 |
| WO | WO 12/037034 | 3/2012 |
| WO | WO 12/045913 | 4/2012 |
| WO | WO 12/061662 | 5/2012 |
| WO | WO 12/151576 | 11/2012 |
| WO | WO 13/096926 | 6/2013 |
| WO | WO 14/070991 | 5/2014 |
| WO | WO 14/149837 | 9/2014 |
| WO | WO 15/019284 | 2/2015 |
| WO | WO-2015019284 A2 * | 2/2015 ......... A61K 31/7028 |
| WO | WO 15/048616 | 4/2015 |
| WO | WO 15/109049 | 7/2015 |
| WO | WO 16/089872 | 6/2016 |
| WO | WO 16/164394 | 10/2016 |
| WO | WO 17/023918 | 2/2017 |
| WO | WO 17/095904 | 6/2017 |

OTHER PUBLICATIONS

Aagaard et al (Advanced Drug Delivery Reviews 59 (2007) 75-86) (Year: 2007).*

Warzocha et al (Leukemia and Lymphoma (1997) vol. 24. pp. 267-281) (Year: 1997).*

McKeague et al (J Nucleic Acids. 2012;2012:748913. Epub Oct. 24, 2012) (Year: 2012).*

FDA Guideline for Industry Dose-response Information to Support Drug Registration (ICH-E4, Nov. 1994) (Year: 1994).*

Ma (Modern Drug Discovery 2004, 7(6)) (Year: 2004).*

Steinman et al (Nat Med. Jan. 6, 2012;18(1):59-65) (Year: 2015).*

Blumberg et al (Nat Med.; 18(1): 35-41) (Year: 2015).*

Sporn et al, "Chemoprevention of Cancer," Carcinogenesis, vol. 21 (2000), 525-530 (Year: 2000).*

Auerbach et al (Cancer and Metastasis Reviews, 2000, 19: 167-172) (Year: 2000).*

Gura T (Science, 1997, 278(5340): 1041-1042, encloses 1-5) (Year: 1997).*

Jain RK (Scientific American, Jul. 1994,58-65) (Year: 1994).*

HogenEsch et al (J Control Release. Dec. 10, 2012; 164(2): 183-186.) (Year: 2012).*

Topalian et al (N Engl J Med. Jun. 28, 2012;366(26):2443-54. doi: 10.1056/NEJMoa1200690. Epub Jun. 2, 2012). (Year: 2012).*

Abraham, W.M. et al., "Selectin Blockade Prevents Antigen-induced Late Bronchial Response and Airway Hyperresponsiveness in Allergic Sheep," Am J. RespirCrit Care Med. 159:1205-1214, 1999.

Acord, J. et al., "A rapid microplate method for quantifying inhibition of bacterial adhesion to eukaryotic cells," Journal of Microbiological Methods 60: 55-62, 2005.

Adams, E. W. et al., "Oligosaccharide and Glycoprotein Microarrays as Tools in HIV Glycobiology: Glycan-Dependent gp120/Protein Interactions," Chemistry & Biology 11:875-881, Jun. 2004.

Aggoune et al., "The Vascular Niche Is Involved in Regulating Leukemic Stem Cells in Murine Chronic Myelogenous Leukemia" Blood, 124(21):516, Dec. 6, 2014.

Aggoune et al., "The vascular niche is involved in regulating leukemic stem cells in murine chronic myelogenous leukemia," Proceedings of the 56th Annual Meeting of the American Society of Hematology, Abstract#516 Oral Presentation, Dec. 8, 2014, San Francisco, CA.

Natoni et al., "Multiple Myeloma Cells Express Functional E-Selectin Ligands Which Can be Inhibited Both in vitro and in vivo Leading to Prolongation of Survival in a Murine Transplant Model," Blood, Dec. 6, 2014, XP055349837, 56th Annual Meeting of the American Society of Hematology, Dec. 6-9, 2014, San Francisco, CA.

Alessandro, et al., "Role of S128R polymorphism of E-selectin in colon metastasis formation," Int. J. Cancer, 121(3): 528-535 (2007).

Ali, M., et al., "Polymers bearing sLex-mimetics are superior inhibitors of E-selectin-dependent leukocyte rolling in vivo", The FASEB Journal 18(1), (2004), 152-154.

Alousi, A., et al., "Reduced-Intensity Conditioning Allogeneic Hematopoietic Stem Cell Transplantation", Clinical Advances in Hematoloav & Oncoloav. 5(7), (2007), 560-570.

Angelini et al., "E-Selectin Antagonist GMI-1271 Shows a Favorable Safety, PK and Bleeding Profile in Phase I Studies of Healthy Volunteers," Blood, 128(22), Abstract #3826, Dec. 2, 2016.

Angelini et al., "E-selectin Antagonist GMI-1271 Shows a Favorable Safety, PK and Bleeding Profile in Phase I Studies of Healthy Volunteers," Proceedings of the 58th Annual Meeting of the American Society of Hematology, Poster Presentation, Dec. 3-6, 2016, San Francisco, CA.

Arakaki, R. et al., "T134, a Small-Molecule CXCR4 Inhibitor, Has No Cross-Drug Resistance with AMD3100, a CXCR4 Antagonist with a Different Structure," Journal of Virology 73(2):1719-1723, Feb. 1999.

Aref et al., "L and E Selectins in Acute Myeloid Leukemia: Expression, Clinical Relevance and Relation to Patient Outcome," Hematology, 7(2), 83-87, 2002.

Arshad, S. et al., "Primary prevention of asthma and atopy during childhood by allergen avoidance in infacny: a randomised controlled study," Thorax., 58:489-493 (2003).

Arshad, S. et al., "Primary prevention of asthma and allergy," J. Allergy Clin. Immunol., 116: 3-14 (2005).

Azab et al., "P-selectin Glycoprotein Ligand Regulates the Interaction of Multiple Myeloma Cells with the Bone Marrow Microenvironment", Blood, 119(6),1468-1478, Nov. 16, 2011.

Azab et al., "Role of Selectins in the Pathogenesis of Multiple Myeloma", J Clin Oncol, 27(15s):Absrt 11103, 2009.

Azab et al., "Role of Selectins in the Pathogenesis of Multiple Myeloma", ASCO Annual Meeting 2009, Poster #11103, May 2009.

Azab et al. "CXCR4 inhibitor AMD3100 disrupts the interaction of multiple myeloma cells with the bone marrow microenvironment and enhances their sensitivity to therapy." Blood, 113(18) 4341-4351, 2009.

Baeckstrom et al., "Purification and Characterization of a Membrane-bound and a Secreted Mucin-type Glycoprotein Carrying the Carcinoma-associated Sialyl-Le$^a$ Epitope on Distinct Core Proteins," J. Biol. Chem. 266(32):21537-21547, 1991.

Banteli, R. et al., "Potent E-Selectin Antagonists," Helvetica Chimica Acta 83(11): 2893-2907, 2000.

Banteli et al., "Synthesis of sialyl lewisx mimics. Modifications of the 6-position of galactose," Bioorganic & Medicinal Chemistry Letters, 11(4): 459-462 (2001).

Barasch et al., "Palifermin for Management of Treatment-Induced Oral Mucositis in Cancer Patients", Biologies: Targets & Therapy, 3:111-116, 2009.

Barnes, P. et al., "How do corticosteroids work in asthma?" Ann. Intern. Med., 139: 359-370 (2003).

Barthel et al., "Targeting selectins and selectin ligands in inflammation and cancer," Expert Opinion Therapeutic Targets, 11(11), 1473-1491, 2007.

Bastin, R.. et al,"Salt Selection and Optimisation Procedures for Pharmaceutical New Chemical Entities" Organic Process Research & Development (2000), vol. 4, pp. 427-435.

Bedard et al., "Expert Opinion: Selectin Inhibitors: A Patent Review," Rights Link, 20(6):781-793, 2010.

Belcher, J.D. et al., "Activated monocytes in sickle cell disease: potential role in the activation of vascular endothelium and vaso-occlusion," Blood 96(7):2451-2459, Oct. 1, 2000.

Belcher, J.D. et al., "Inflammatory response in transgenic mouse models of human sickle cell anemia," Blood 96(11)Pt. 1 :600a, Abstract #2574, Nov. 16, 2000.

Bennett, C. F., et al., "Inhibition of Endothelial Cell Adhesion Molecule Expression with Antisense Oligonucleotides", Journal of Immunology. 152(7), (1994), 3530-3540.

Berg et al., "A Carbohydrate Domain Common to Both Sialyl Le$^a$ and Sialyl Le$^x$ Is Recognized by the Endothelial Cell Leukocyte Adhesion Molecule ELAM-1," J. Biol. Chem. 266(23):14869-14872, 1991.

(56) References Cited

OTHER PUBLICATIONS

Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.
Berger et al., "Adoptive transfer of effector CD8+ T cells derived from central memory cells establishes persistent T cell memory in primates." J. Clin. Invest. 118(1):294-305 (2008).
Bevilacqua, et al., "Endothelial-leukocyte adhesion molecules in human disease," Ann. Rev. Med., 45:361-378 (1994).
Bhaskar, V. et al. "E-selectin Up-regulation Allows for Targeted Drug Delivery in Prostate Cancer," Cancer Research, 63: 6387-6394 (Oct. 2003).
Bird and Kimber, "Oligosaccharides Containing Fucose Linked α(1-3) and α(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978, and English Translation.
Bochner, B. et al., "Glycan array screening reveals a candidate ligand for Siglec-8," Journal of Biological Chemistry, 280(6): 4307-4312 (2005).
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour With Respect to the Enzyme Trehalase," European Journal of Biochemistry, 131:595-600, 1983.
Bogden, A. E., et al., "Amelioration of Chemotherapy-Induced Toxicity by Cotreatment with AcSDKP, a Tetrapeptide Inhibitor of Hematopoietic Stem Cell Proliferation", Annals New York Academy of Sciences. 628, (1991), 126-139.
Borsig et al., "Synergistic effects of L- and P-selectin in facilitating tumor metastasis can involve non-mucin ligands and implicate leukocytes ad enhancers of metastasis," Proceedings of the National Academy of Sciences, 99(4), 2193-2198, 2002.
Bowen et al., "Characterization of a Human Homologue of the Murine Peripheral Lymph Node Homing Receptor," Journal of Cell Biology, 109:421-427, 1989.
Bradford, G. B., et al., "Quiescence, cycling, and turnover in the primitive hematopoietic stem cell compartment", Experimental Hematology. 25, (1997), 445-453.
Brandley et al., "Carbohydrate Ligands of LEC Cell Adhesion Molecules," Cell, 63:861-863, 1990.
Breems et al., "Prognostic Index for Adult Patients With Acute Myeloid Leukemia in First Relapse," Journal of Clinical Oncology, 23(9(), 1969-1978, 2005.
Bridger, GJ et al. "Synthesis and Structure—Activity Relationships of Phenylenebis(methylene)—Linked Bis-Tetraazamacrocycles That Inhibit HIV Replication. Effects of Macrocyclic Ring Size and Substituents on the Aromatic Linker," J. Med. Chem., 38: 366-378 (1995).
Brodt et al., "Liver endothelial E-selectin mediates carcinoma cell adhesion and promotes liver metastasis," Int. J. Cancer, 71(4): 612-619 (1997).
Broquet et al., "Effect of Desipramine on a Glycoprotein Sialyltransferase Activity in C6 Cultured Glioma Cells," J. Neurochem., 54:388-394, 1990.
Burkhardt, K., et al., "The Significance of Adhesion Molecules in Nephrology", Artificial Organs 20(5), (1996), 433-436.
Calarese, D. A. et al., "Antibody Domain Exchange is and Immunological Solution to Carbohydrate Cluster Recognition," Science 300:2065-2071, Jun. 2003.
Calarese, D. A. et al., "Dissection of the Carbohydrate Specificity of the Broadly Neutralizing Anti-HIV-1 Antibody 2G12," Proceedings of the National Academy of Sciences 102(38):13372-13377, Sep. 2005.

Cao, X. et al., "Defective Lymphoid Development in Mice Lacking Expression of the Common Cytokine Receptor Y Chain," Immunity, 2:223-238, Mar. 1995.
Ceder, O. et al., "On the Absolute Configuration of3-Cyclohexene-1-carboxylic Acid," Acta Chemica Scandivavica, 24(8):2693-2698, 1970.
Chang et al., "Effects of Pan-Selectin Antagonist GMI-1070 on the Treatment of Vaso-Occlusion in Sickle Cell Mice", Blood, 112(11), Abstract #535, Nov. 2008.
Chang, J. et al. "GMI-1070, a novel pan-selectin antagonist, reverses acute vascular occlusions in sickle cell mice," Blood, 116(10): 1779-1786 (Sep. 2010).
Chase et al., "E-Selectin Ligands as Mechanosensitive Receptors on Neutrophils in Health and Disease", Annals of Biomedical Engineering, 40(4), pp. 849-899, Apr. 2012.
Chen et al. "CXCR4 inhibition in tumor microenvironment facilitates anti-programmed death receptor-1 immunotherapy in sorafenib-treated hepatocellular carcinoma in mice." Hepatology 61.5 (2015): 1591-1602.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML," Proceedings of the 54th Annual Meeting of the American Society of Hematology, Abstract #4092, Poster Presentation, Dec. 10, 2012, San Diego, CA.
Chien et al., "Adhesion of Acute Myeloid Leukemia Blasts to E-Selectin in the Vascular Niche Enhances Their Survival By Mechanisms Such as Wnt Activation", Blood, 122(21):61, Nov. 15, 2013.
Chien et al., "579 Novel Dual E-Selectin-CXCR4 Inhibitors Mobilize Human Acute Myeloid Leukemia (AML) Cells in the NODscid IL2Rγc-/- Xenograft and Confer Susceptibility to Cytarabine," Blood, 118(21) Abstract #579, Oral, Nov. 18, 2011.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", Blood, 120(21), Abstract #4092, Nov. 16, 2012.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", 2012 ASH Annual Meeting, Poster #54715, Dec. 10, 2012.
Chien et al., "Novel Dual E-Selectin-CXCR4 Inhibitors Mobilize Human Acute Myeloid Leukemia (AML) Cells in the NODscid IL2R{gamma}c-/- Xenograft and Confer Susceptibility to Cytarabine", Blood, 118(21), Abstract #579, Nov. 18, 2011.
Childs et al. ,"High-molecular-weight glycoproteins are the major carriers of the carbohydrate differentiation antigens I, I and SSEA-1 of mouse teratocarcinoma cells," Biochem. J., 215:491-503 (1983).
Choi, S. et al., "Synthetic Multivalent Molecules: Concepts and Biomedical Applications," Wiley-Interscience, p. xxi-xxvi, 1-17, 2004.
Christianson, S.W. et al.,"Enhanced Human CD4+ T Cell Engraftment in B2-Microglobulin-Deficient NOD-scid Mice," The Journal of Immunology, 158:3578-3586 (1997).
Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).
Collier, et al., "Membrane translocation by anthrax toxin," Molecular Aspects of Medicine, 30(6): 413-422 (Dec. 1, 2009).
Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).
Corson, Timothy W. et al., "Design and Applications of Bifunctional Small Molecules: Why Two Heads Are Better Than One," ACS Chemical Biology 3(11):677-692, Nov. 2008.
Cottler-Fox, M.H. et al., "Stem Cell Mobilization," Amer. Sci. Hematology, 419-437, (2003).
Crawford et al., "AMD070, a CXCR4 Chemokine Receptor Antagonist: Practical Large-Scale Laboratory Synthesis," Org. Process Res. Devel. 12:823-830, 2008.

(56) References Cited

OTHER PUBLICATIONS

Cumpstey, I. et al. "C2-Symmetrical Thiodigalactoside Bis-Benzamido Derivatives as High-Affinity Inhibitors of Galectin-3: Efficient Lectin Inhibition through Double Arginine-Arene Interactions," Angew Chem., 117:5240-5242 (2005).
Dagia, Nilesh et al., "G-CSF induces E-selecting ligand expression on human myeloid cells," Nature Medicine, 12(10): 1185-90, Oct. 1, 2006.
Daoudii, Jean-Michel et al., "New bicyclam-GalCer analogue conjugates: synthesis and in vitro anti-HIV activity," Bioorg. & Med. Chem. Letters 14:495-498, 2004.
Datta and Takayama, "Isolation and purification of trehalose 6-mono- and 6,6'-di-corynomycolates from Cornyebacterium matruchotii. Structural characterization of $^1$H NMR," Carbohydrate Research 245:151-158, 1993.
De Castro et al., "Effects of GMI-1070, a Pan-Selectin Inhibitor, On Pain Intensity and Opioid Utilization in Sickle Cell Disease", Blood, 122(21):775, Nov. 15, 2013.
De Clercq, Erik, "The bicyclam AMD3100 story," Nat. Rev. Drug Disc. 2:581-587, Jul. 2003.
DeAngelo, "A Phase I/II Study of GMI-1271, a Novel ESelectin Antagonist, in Combination with Induction Chemotherapy in Relapsed/Refractory and Elderly Previously Untreated Acute Myeloid Leukemia; Results to Date," Blood, 128(22), Abstract #4049, Dec. 2, 2016.
DeAngelo et al. "GMI-1271, a novel E-selectin antagonist, in combination with chemotherapy in relapsed/refractory AML", Journal of Clinical Oncology, vol. 35, No. 15, suppl, May 20, 2017, p. 2520.
Definition of allogenic. Medline Plus-Merriam-Webster Medical Dictionary (last accessed Jun. 3, 2013).
Definition of syngeneic. Medline Plus-Merriam-Webster Medical Dictionary (last accessed Jun. 3, 2013).
Definition of xenogeneic. Medline Plus-Merriam-Webster Medical Dictionary (last accessed Jun. 3, 2013).
Demain et al. "Natural products for cancer chemotherapy," Microbio. Biotechnol. 4(6): 687-699, 2011.
Devata et al., First in Human Phase 1 Single Dose Escalation Studies of the E-Selectin Antagonist GMI-1271 Show a Favorable Safety, Pharmacokinetic, and Biomarker Profile, Proceedings of the 57$^{th}$ Annual Meeting of the American Society of Hematology, Abstract #1004, Poster Presentation, Dec. 5, 2015, Orlando, FL.
Devata et al., "First in Human Phase 1 Single Dose Escalation Studies of the E-Selectin Antagonist GMI-1271 Show a Favorable Safety, Pharmacokinetic, and Biomarker Profile," Blood, 126(23), Abstract#1004, Dec. 3, 2015.
Devereux, J., et al., "A comprehensive set of sequence analysis programs for the VAX", Nucleic Acids Research 12(1), (1984), 387-395.
Devine, "Rapid Mobilization of CD34+ Cells Following Administration of the CXCR4 Antagonist AMD 3100 to Patients With Multiple Myeloma and Non-Hodgkin's Lymphoma," Journal of Clinical Oncology, 22(6): 1095-1102 (Feb. 23, 2004).
Deweerdt, "Animal models: Towards a myeloma mouse," Nature, 480 (7377): S38-39 (2011).
Diamandis et al., "Reflection on the Discovery of Carcinoembryonic Antigen, Prostate-Specific Antigen, and Cancer Antigens CA125 and CA19-9", Clin Chem, 59(1), Nov. 30, 2012.
Diaz-Ricart et al., "rPSGL-lg" Drugs of the Future 27(4):346 (2002).
Dimasi et al., "Expression, crystallization and preliminary crystallographic analysis of the extracellular IgV-like domain of the human natural killer cell inhibitory receptor p75/AIRM1," Acta Crystallographica Section D, Biological Crystallography, 59(Pt 10), 1856-1858, 2003.
Dimasi et al., "Structure of the saccharide-binding domain of the human natural killer cell inhibitory receptor p75/AIR1. Erratum," Acta Crystallographica Section D, Biological Crystallography, 60(Pt 2), Erratta, 401-403, 2004.
Dittmar et al., "Adhesion Molecules and Chemokines: the Navigation System for Circulating Tumor (Stem) Cells to Metastasize in an Organ-Specific Manner," Clin. Exp. Metastasis 25:11-32, 2008.
Doranz et al., "Safe Use of the CXCR4 Inhibitor ALX40-4C in Humans," AIDS Research and Human Retroviruses 17(6):475-486, 2001.
Duijvestijn et al., "High Endothelial Differentiation in Human Lymphoid and Inflammatory Tissues Defined by Monoclonal Antibody HECA-452," Am. J. Path. 130:147-155, 1988.
Dupre et al., "Glycomimetic Selectin Inhibitors: (.alpha.-D-Mannopyranosyloxy)methylbiphenyls," Bioorganic & Medicinal Chemistry Letters 6(5): 569-572, 1996.
Dutta et al "E-selectin inhibition mitigates splenic HSC activation and myelopoiesis in hypercholesterolemic mice with myocardial infarction highlights" Arteriosclerosis, Thrombosis, and Vascular Biology 36(9):1802-08 (2016).
Dykewicz, "Summary of the Guidelines for Preventing Opportunistic Infections among Hematopoietic Stem Cell Transplant Recipients," Clin. Infectious Diseases, 33:139-144, Jul. 15, 2001.
Edgington, "How Sweet It Is: Selectin-Mediating Drugs," Biotechnology 10: 383-389, 1992.
Edwards, "Generally Applicable, Convenient Solid-Phase Synthesis and Receptor Affinities of Octreotide Analogs," J. Med. Chem. 37:3749-3757, 1994.
Egberink et al. "Bicyclams, Selective Antagonists of the Human Chemokine Receptor CXCR4, Potently Inhibit Feline Immunodeficiency Virus Replication," Journal of Virology, 73(8): 6346-6352 (1999).
Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al., "Specific Interaction between Le$^x$ and Le$^x$ Determinants. A Possible Basis for Cell Recognition in Preimplantation Embryos and in Embryonal Carcinoma Cells," J. Biol. Chem. 264(16):9476-9484, 1989.
Egger et al. "Nanomolar E-Selectin Antagonists with Prolonged Half-Lives by a Fragment-Based Approach," JACS, 135(26): 9820-9828 (Jul. 2013).
Embury et al., "The contribution of endothelial cell P-selectin to the microvascular flow of mouse sickle erythrocytes in vivo," Blood 104(10):3378-3385, Nov. 15, 2004.
Ernst et al., "Design and Synthesis of E-Selectin Antagonists," Chimia 55:268-274, 2001.
Ernst et al., "From carbohydrate leads to glycomimetic drugs," Nature Reviews 8:661-677, Aug. 2009.
Ernst, "Substrate and donor specificity of glycosyl transferases," Glycoconjugate Journal 16: 161-170, 1999.
Esposito et al., "Exploration of a Potent E-selectin Antagonist (GMI-1271) as a Potential Therapeutic for Treating Breast Cancer Metastasis to the Lung and Bone", AACR Annual Meeting 2014, Poster #4039, Apr. 8, 2014.
Esposito et al., "Exploration of a Potent E-selectin Antagonist (GMI-1271) as a Potential Therapeutic for Treating Breast Cancer Metastasis to the Lung and Bone", Cancer Res, Abstract #4039, Oct. 1, 2014.
Faber et al., "The Many Facets of SDF-1a, CXCR4 Agonists and Antagonists on Hematopoietic Progenitor Cells," J. Biomed. & Biotech. Article ID 26065:1-10, 2007.
Faderl et al., "Clofarabine Plus Cytarabine Compared With Cytarabine Alone in Older Patients With Relapsed or Refractory Acute Myelogenous Leukemia: Results From the CLASSIC I Trial," Journal of Clinical Oncology, 30(20), 2492-2499, 2012.
Feletou, M. et al., "Endothelial dysfunction: a multifaceted disorder," Am. J. Physiol. Heart Circ. Physiol., 291: H985-H1002 (2006).
Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.

(56) References Cited

OTHER PUBLICATIONS

Fenderson et al., "The blood group I antigen defined by monoclonal antibody C6 is a marker of early mesoderm during murine embryogenesis," Differentiation 38:124-133, 1988.
Filser, C. et al., "Synthetic glycopeptides from the E-selectin ligand 1 with varied sialyl Lewis(x) structure as cell-adhesion inhibitors of E-selectin," Angewandte Chemie—International Edition, 46(12): 2108-2111 (2007).
Flanner et al., "Comparison of Predicted GMI-1070 Human Intravenous Pharmacokinetics from in silico PBPK and Allometric Scaling Models", AAPS Annual Meeting, Abstract, Nov. 2009.
Frenette, Paul S. et al., "Sulfated Glycans Induce Rapid Hematopoietic Progenitor Cell Mobilization: Evidence for Selectin-Dependent and Independent Mechanisms," Blood, 96:2460-2468, (2000).
Frison, N. et al., "Oligolysine-Based Oligosaccharide Clusters: Selective Recognition and Endocytosis by the Mannose Receptor and Dendritic Cell-Specific Intercellular Adhesion Molecule 3 (ICAM-3)-Grabbing Nonintegrin," The Journal of Biological Chemistry 278(26):23922-23929, Apr. 2003.
Fruehauf, S., et al., "Protection of hematopoietic stem cells from chemotherapy-induced toxicity by multidrug-resistance 1 gene transfer," Recent Results in Cancer Research, 144, Abstract Only), (1998), 1 pQ.
Fukushi et al., "Novel Fucolipids Accumulating in Human Adenocarcinoma," J. Biol. Chem. 259(16):10511-10517 (1984).
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al., "Endogenous Tumor Lectins: Overview and Perspectives," Anticancer Res. 6:573-578, 1986.
Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocytes," Nature 304:30-34, 1983.
Garber, N. et al., "On the specificity of the D-galactose-binding lectin (PA-I) of Pseudomonas aeruginosa and its strong binding to hydrophobic derivatives of D-galactose and thiogalactose," Biochimica et Biophysica Acta, 1116:331-333 (1992).
Gelbrich, T. et al., "Preparation of 4-benzylsulfanyl[1,2,3,5]dithiadiazol-1-ylium chlorides: potential precursors to meso-ionic 1,2,3,5-dithiadiazolium-4-thiolate,"Arkivoc, (vi): 224-223 (2002).
Ghobrial, IM, "Myeloma as a model for the process of metastasis: implications for therapy," 120(1): 20-30 (2012).
Gilboa-Gardner, N. et al., "A new mitogenic D-galactosephilic lectin isolated from seeds of the coral-tree Erythrina corallodendron. Comparison with Glycine max (soybean) and Pseudomonas aeruginosa lectins," Canadian Journal of Biochemistry, 59(5):315-320 (1981).
Goodman and Gillman's, "Pharmacological Basis of Therapeutics," 10$^{th}$ edition, p. 54 (2001).
Gooi et al., "Stage-specific embryonic antigen involves alpha 1-3 fucosylated type 2 blood group chains," Nature 292:156-158, 1981.
Gout, et al., "Selectins and selectin ligands in extravasation of cancer cells and organ selectivity of metastasis," Clin. Exp. Metastasis, 25(4): 335-344 (2008).
Gravina et al., "Abstract 428: Dual E-selectin and CXCR4 inhibition reduces tumor growth and increases the sensitivity to docetaxel in experimental bone metastases of prostate cancer," Cancer Research, 75(15 Supplemental), 428-429, Aug. 2, 2015.
Gravina et al., "Abstract 428: Dual E-selectin and CXCR4 inhibition reduces tumor growth and increases the sensitivity to docetaxel in experimental bone metastases of prostate cancer," Proceedings of the 106th Annual Meeting of the American Association for Cancer Research, Abstract #428, Apr. 18-22, 2015, Philadelphia, PA.
Griciuc et al., "Alzheimer's Disease Risk Gene CD33 Inhibits Microglial Uptake of Amyloid Beta," Neuron, 78(4), 631-643, May 22, 2013.
Griffioen and Vyth-Dreese, "Angiostasis as a way to improve immunotherapy." Thrombosis and Haemostasis, 101.06 (2009): 1025-1031.
Guha et al., "Cod glycopeptide with picomolar affinity to galectin-3 suppresses T-cell apoptosis and prostate cancer metastasis," Proceedings of the National Academy of Science, 110(13), 5052-5057, 2013.
Hakomori, "Aberrant Glycosylation in Cancer Cell Membranes as Focused on Glycolipids: Overview and Perspectives," Cancer Res. 45:2405-2414, 1985.
Hakomori et al., "Novel Fucolipids Accumulating in Human Adenocarcinoma. I. Glycolipids With Di-or Trifucosylated Type 2 Chain," J. Biol. Chem. 259(7):4672-4680, 1984.
Halloran et al., "Ley/H: An endothelial-selective cytokine-inducible angiogenic mediator," Journal of Immunology, 164(9): 4868-4877 (May 1, 2000).
Hamamoto et al., "Inhibition of Dextran Sulphate Sodium (DSS)-induced Colitis in Mice by Intracolonically Administered Antibodies Against Adhesion Molecules (Endothelial Leucocyte Adhesion Molecule-1 (ELAM-1) or Intercellular Adhesion Molecule-1 (ICAM-1))", Clin. Exp. Immunol., 117, (1999), 462-468.
Handa et al., "Selectin GMP-140 (CD62; PADGEM) Binds to Sialosyl-Le$^a$ and Sialosyl-Le$^x$, and Sulfated Glycans Modulate this Binding," Biochemical and Biophysical Research Communication 181 (3):1223-1230, 1991.
Handschel et al., "Irradiation induces increase of adhesion molecules and accumulation of beta2-integrin-expressing cells in humans" International Journal of Radiation Oncology, Biology, Physics 45(2): 475-481 (1999).
Hansson et al., "Biosynthesis of the Cancer-associated Sialyl-Le.sup.a Antigen," Journal of Biological Chemistry 260(16):9388-9392, 1985.
Harlan, "Introduction-anti-adhesion therapy in sickle cell disease," Blood 95:365-367, 2000.
Hasegawa et al., "Synthesis of deoxy-L-fucose-containing sialyl Lewis X ganglioside analogues," Carbohydrate Research 257: 67-80, 1994.
Hasegawa et al., "Synthesis of sialyl Lewis X ganglioside analogues containing modified L-fucose residues," Carbohydrate Research 274:165-181, 1995.
Hayashi et al., "Increased Level of Soluble E-Selectin in the Serum from Patients with Idiopathic Pulmonary Fibrosis," Inflammation, 28(1), 1-5, 2004.
Hebbar et al., "E-selectin gene S128R polymorphism is associated with poor prognosis in patients with stage II or III colorectal cancer," European Journal of Cancer, 45, 1871-1876, 2009.
Hebbel, P.R., "Blockade of Adhesion of Sickle Cells to Endothelium by Monoclonal Antibodies," The New England Journal of Medicine 342:1910-1912, Jun. 22, 2000.
Hendrix, C.W. et al., "Pharmacokinetics and Safety of AMD-3100, a Novel Antagonist of the CXCR-4 Chemokine Receptor, in Human Volunteers," Antimicrobial Agents and Chemotherapy 44(6):1667-1673, Jun. 2000.
Hickey et al., "Leukocyte-Endothelial Cell Interactions Are enhanced in Dermal Postcapillary Venules of MRL/fas$^{lpr}$ (Luplus-Prone) Mice: Roles of P- and E-Selectin," The Journal of Immunology, 168, 4728-4736, 2002.
Hiddemann et al., "Management of Acute Myeloid Leukemia in Elderly Patients," Journal of Clinical Oncology, 17(11), 3569-3576, 1999.
Hilal et al., "Electronic structure of orotic acid I. Geometry, conformational preference and tautomerism:, Journal of Molecular Structure (Theochem)" 685 (2004) 35-42.
Hilgenbrink et al., "Folate receptor-mediated drug targeting: from therapeutics to diagnostics," J. Pharm. Sci., 94(10): 2135-2146 (2005).
Holgate, ST et al., "Epithelium dysfunction in asthma," Current Reviews of Allergy and Clinical Immunology, 120: 1233-1234 (2007).
Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.

(56) References Cited

OTHER PUBLICATIONS

Hong, P. W.-P. et al., "Identification of the Optimal DC-SIGN Binding Site on Human Immunodeficiency Virus Type 1 gp120," Journal of Virology 18(15):8325-8336, Aug. 2007.
Horacek et al., "Multi-analytical evaluation of serum levels of cytokines and adhesion molecules in patients treated for acute myeloid leukemia using biochip array technology," Biomed Pap Med Fac Univ Palacky Olomouc, Czech Repub., 157(4), 277-279, Dec. 2013.
Horiya et al., "Recent strategies targeting HIV glycans in vaccine design," Nature Chemical Biology, 10, 990-999, 2014.
Huang et al., "Postischemic Cerebrovascular E-Selectin Expression Mediates Tissue Injury in Murine Stroke," Stroke, 31, 3047-3053, 2000.
Huse et al., "Generation of a Large Combinatorial Library of the Immunoglobulin Repertoire in Phage Lambda," Science 246:1275-1281, 1989.
Huwe, C. M. et al., "Design, Synthesis and Biological Evaluation of Aryl-substituted Sialyl Lewis X Mimetics Prepared via Cross-metathesis of C-Fucopeptides," Biological & Medicinal Chemistry 7:773-788, 1999.
Hynes, R., "Integrins: A Family of Cell Surface Receptors," Cell 48:549-554, 1987.
Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.
International Search Report and Written Opinion for PCT/US2017/045690 dated Jan. 3, 2018.
Inwald, D. P. et al., "Platelet and leucocyte activation in childhood sickle cell disease: association with nocturnal hypoxaemia," British Journal of Haematology, 111:474-481, Nov. 2000.
Ishikawa, F. et al., "Chemotherapy-resistant human AML stem cells home to and engraft within the Bone-marrow endosteal region," Nature Biotechnology 25(11):1315-1321, Nov. 2007.
Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.
Itai, S. et al., "Differentiation-dependent Expression of I and Sialyl I Antigens in the Developing Lung of Human Embryos and in Lung Cancers," Cancer Research 50: 7603-7611, 1990.
Jeffrey et al., "Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al., "Inhibition of Human Immunodeficiency Virus Type I Reverse Transcriptase by Suramin-related Compounds," The Journal of General Virology 68(8): 2183-2192, 1987.
Jentsch, TJ et al. "Ion Channels: Function Unravelled by Dysfunction," Nature Cell Biology, 6(11): 1039-1047 (Nov. 2004).
Jiang et al., "CD33 in Alzheimer's Disease," Molecular Neurobiology, 46, 529-535, 2014.
Jubeli et al., "E-selectin as a target for drug delivery and molecular imaging," Journal of controlled Release, 158, 194-206, 2012.
Juliusson et al., "Age and acute myeloid leukemia: real world data n decision to treat and outcomes from the Swedish Acute Leukemia Registry," Blood, 113, 4170-4187, 2009.
Kaila, N. et al., "B-C-Mannosides as Selectin Inhibitors," Journal of Medicinal Chemistry 45(8): 1563-1566, 2002.
Kaila, N. et al., "Design and synthesis of sialyl Lewis(x) mimics as E- and P-selectin inhibitors," Med Res Rev 22(6):566-601, Nov. 2002.
Kannagi, R. et al. "Carbohydrate-mediated cell adhesion in cancer metastasis and angiogenesis," Cancer Sci., 95(5): 377-384 (2004).
Kannagi et al., "Stage-specific embryonic antigens (SSEA-3 and -4) are epitopes of a unique globo-series ganglioside isolated from human teratocarcinoma cells," Embo J. 2(12):2355-2361, 1983.
Kansas, G., "Selectins and Their Ligands: Current Concepts and Controversies," Blood, 88(9): 3259-3287 (1996).
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Katayama, Y., et al., "CD 44 is a physiological E-selectin ligand on neutrophils", J. Exp. Med. 201(8), (2005), 1183-1189.
Katayama, Y. et al., "PSGL-1 Participates in E-Selectin-Mediated Progenitor Homing to Bone Marrow: Evidence for Cooperation Between E-Selectin Ligands and a4 Integrin," Blood, 102:2060-2067, (2003).
Kaul, D.K. et al., "Hypoxia/reoxygenation causes inflammatory response in transgenic sickle mice but not in normal mice," The Journal of Clinical Investigation 106(3):411-420, Aug. 2000.
Kayser, S. et al., "Advances in targeted therapy for acute myeloid leukemia", British Journal of Haematology, 180(4):484-500 (2018).
Khatib, A.-M., et al., "Inhibition of Hepatic Endothelial E-Selectin Expression by C-raf antisense Oligonucleotides Blocks Colorectal Carcinoma Liver Metastasis", Cancer Research 62(19), (2002), 5393-5398.
Kiel, M.J., et al., "SLAM Family Receptors Distinguish Hematopoietic Stem and Progenitor Cells and Reveal Endothelial Niches for Stem Cells," Cell, 121(7):1109-1121 (2006).
Kilgore et al., "Reducation of myocardial infarct size in vivo by carbohydrate-based glycomimetics" Journal of Pharmacology and Experimental Therapeutics, American Society for Pharmacology and Experimental Therapeutics, 284(1):427-435 (1998).
Kim et al., "Inhibition of the CXCR4/CXCL12 Chemokine Pathway Reduces the Development of Murine Pulmonary Metastases," Clin. Exp. Metastasis 25(3):201-211, 2008.
Kitagawa et al., "Characterization of Mucin-Type Oligosaccharides With the Sialyl-Le$^a$ Structure From Human Colorectal Adenocarcinoma Cells," Biochem. Biophys. Res. Commun. 178(3):1429-1436, 1991.
Kitagawa et al., "Immunoaffinity Isolation of a Sialyl-Le$^a$ Oligosaccharide from Human Milk," J. Biochem. 104:591-594, 1988.
Klyosov et al., "Galectins in Disease and Potential Therapeutic Approaches," In Galectins and Disease Implications for Targeted Therapeutics, American Chemical Society, Washington, DC, Chapter 1, pp. 3-43, 2012.
Kneuer et al: "Selectins—potential pharmacological targets?" Drug Discovery Today vol. 11, No. 21-22, pp. 1034-1040, Oct. 2006.
Ko, HL et al. "In Vitro and In Vivo Inhibition of Lectin Mediated Adhesion of Pseudomonas aeruginosa by Receptor Blocking Carbohydrates," Infection, 15(4): 21-24 (1987).
Kobayashi et al., "Cimetidine Inhibits Cancer Cell Adhesion to Endothelial Cells and Prevents Metastasis by Blocking E-selectin Expression," Cancer Research, 60, 3978-3984, 2000.
Koch, Alisa E et al., "Angiogenesis mediated by soluble forms of E-selectin and vascular cell adhesion molecule-1," Nature, 376(6540): 517-519 (1995).
Koenig et al., "Selectin Inhibition: Synthesis and Evaluation of Novel Sialylated, Sulfated and Fucosylated Oligosaccharides, Including the Major Capping Group of Glycam-1", Glycobiology, 7(1):79-93 (1997).
Kogan, T.P. et al., "Novel Synthetic Inhibitors of Selectin-Mediated Cell Adhesion: Synthesis of 1,6-Bis[3-(3-carboxymethylphenyl)-4-(2-α-D-monnopyranosyloxy)phenyl]hexane (TBC1269)," J Med. Chem. 41:1099-1111, 1998.
Kogan, T.P. et al., "Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38: 4976-4984, Dec. 22, 1995.
Kogan, T.P. et al., "Rational Design and Synthesis of Oligosaccharide Mimetics: Selectin Antagonists as Cell Adhesion Inhibitors," Abstracts of Papers, 210$^{th}$ ACS National Meeting, American Chemical Society, Chicago, IL, Aug. 20-24, 1995, MEDI-18.
Kohler et al., "Continuous cultures of fused cells secreting antibody of predefined specificity," Nature 256:495-497, 1975.
Kohler et al., "Derivation of specific antibody-producing tissue culture and tumor lines by cell fusion," Eur. J. Immunol. 6:511-519, 1976.
Kojima et al., "Specific Interaction between Gangliotriaosylceramide (Gg$_3$) and Sialosyllactosylceramide (G$_{M3}$) as a Basis for Specific Cellular Recognition between Lymphoma and Melanoma Cells," J. Biol. Chem. 264(34):20159-20162, 1989.

(56) References Cited

OTHER PUBLICATIONS

Kolb et al., "Development of Tool for the Design of Selectin Antagonists," Chem. Eur. J. 3(10):1571-1578, 1997.
Kolb et al., "Recent progress in the glycodrug area," Pure & Applied Chemistry 69(9):1879-1884, 1997.
Komrokji et al., "The Colony-Stimulating Factors: Use to Prevent and Treat Neutropenia and Its Complications," Expert Opin.Biol. Then, 4:1897-1910, (2004).
Koprowski et al., "Colorectal Carcinoma Antigens Detected by Hybridoma Antibodies," Somatic Cell Genetics 5(6):957-972, 1979.
Kulidjian et al., "Differential role of E-seletin and P-selectin in T lymphocyte migration to cutaneous inflammatory reactions induced by cytokines," International Immunology, 14(7), 751-760, 2002.
Kuuliala et al., "Circulating soluble E-selectin in early rheumatoid arthritis: a prospective five year study," Annals of Rheumatic Diseases, 61, 242-246, 2002.
Kuzuoka, "Antitumor activity of murine monoclonal antibody NCC-ST-421," Chem. Ab. 115:27344v, 1991.
Kwiatskowski et al., "Tautomerism and Electronic Structure of Biological Pyrimidines" Adv Het Chem 1975, pp. 199-335.
Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.
Kyriakides et al., Surgery, 128(2):327-31, Aug. 2000.
Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.
Lanne, B. et al., "Binding of the galactose-specific Pseudomonas aeruginose lectin, PA-I, to glycosphingolipids and other glycoconjugates," Glycoconjugate Journal, 11:292-298 (1994).
Larsen et al., "PADGEM-Dependent Adhesion of Platelets to Monocytes and Neutrophils is Mediated by a Lineage-Specific Carbohydrate, LNF III (CD15)," Cell 63:467-474, 1990.
Lee et al., "A new method of sequencing linear oligosaccharides on gels using charged, fluorescent coniugates" Carbohydrate Research, vol. 214, 1991, pp. 155-168, XP000226749.
Lemoli et al., "Hematopoietic stem cell mobilization," Haematologica, 93 (3): 321-324 (2008).
Leppla, S H et al., "Anthrax Toxin Fusion Proteins for Intracellular Delivery of Macromolecules," Journal of Applied Microbiology., 87(2): p. 284 (Aug. 1, 1999).
Ley, K. et al., "Selectins in T-cell Recruitment to Non-Lymphoid Tissues and Sites of Inflammation," Nature Reviews, 4: 1-11 (May 2004).
Ley, K., "The role of selectins in inflammation and disease," Trends in Molecular Medicine, 9(6): 263-268 (Jun. 2003).
Li et al., "Hematopoietic-Derived Galectin-3 Causes Cellular and Systemic Insulin Resistance," Cell, 167, 973-984, 2016.
Li et al., "Increased CSF E-Selectin in Clinical Alzheimer's Disease without Altered CSF $A\beta_{42}$ and Tau," Journal of Alzheimer's Disease, 47, 883-887, 2015.
Li, B., et al., "Delaying Acute Graft-Versus-Host Disease in Mouse Bone Marrow Transplantation by Treating Donor Cells with Antibodies Directed at L-Selectin and a4 Integrin Prior to Infusion," Scand. J, I Immunol 59:464-468, 2004.
Liang et al., "Clinicopathological and prognostic significance of sialyl Lewis X overexpression in patients with cancer: a meta-analysis," Onco Targets and Therapy, 9, 3113-3125, 2016.
Lindenberg et al., "Carbohydrate binding properties of mouse embryos," J. Reprod. Fert. 89:431-439, 1990.
Lipartiti et al., "Monosialoganglioside GM1 Reduces NMDA Neurotoxicity in Neonatal Rat Brain," Experimental Neurology 113:301-305, 1991.
Liu et al., "Altering the Specificity of the Antibody Response to HIV gp120 with a Glycoconjugate Antigen," ACS Chemical Biology, 11, 1702-1709, 2016.
Liu et al., "Broadly Neutralizing Antibody-Guided Carbohydrate-Based HIV Vaccine Design: Challenges and Opportunities," ChemMedChem, 11, 357-362, 2016.

Llmer et al., "Cell surface galectin-3 defines a subset of chemoresistant gastrointestinal tumor-initiating cancer cells with heightened stem cell characteristics," Cell Death and Disease, 7, e2337, 1-9, 2016.
Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.
Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.
Lowe et al., "ELAM-1-Dependent Cell Adhesion to Vascular Endothelium Determined by a Transfected Human Fucosyltransferase cDNA," Cell 63:475-484, 1990.
Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870, May 2009.
Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.
Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.
Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.
Magnani et al., "Glycomimetic Drugs—A New Source of Therapeutic Opportunities," Discovery Medicine, 8(43), 247-252, 2009.
Magnani et al., "Pan-selectin Antagonist GMI-1070 affects Biomarkers of Adhesion, Activation and the Coagulation Cascade in Sickle Cell Adults at Steady State", Blood, 120, Abstract #87, Nov. 2012.
Magnani, "The Discovery, Biology, and Drug Development of Sialyl Le$^a$ and Sialyl Le$^x$", Archives of Biochemistry and Biophysics, 426:122-131, May 8, 2004.
Magnani, J., "Carbohydrate Sequences Detected by Murine Monoclonal Antibodies," Chemistry and Physics of Lipids 42:65-74, 1986.
Magnani, J., "Potent Glycomimetic Inhibitors of the Adhesion Molecule, PA-IIL, for the Bacterial Pathogen, Pseudomonas auroginosa," Glycobiology 13(11): 854, Abstract No. 104, Oct. 2003.
Maly, P., et al., "The a(1,3)Fucosyltransferase Fuc-TVII Controls Leukocyte Trafficking through an Essential Role in L-, E-, and P-selection Ligand Biosynthesis", Cell. 86(4), It 1996), 643-653.
Mann, AP et al., "Identification of Thioaptamer Ligand against E-Selectin: Potential Application for Inflamed Vasculature Targeting," PLoS ONE, 5(9): 1-11 (Sep. 2010).
Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.
Matsui, N. M. et al., "The Novel Adhesion of Erythrocytes to P-Selectin in Sickle Cell Disease," Blood 96(11) Pt. 1:600a, Abstract #2575, Nov. 16, 2000.
Matsui, N. M.et al., "P-selectin mediates the adhesion of sickle erythrocytes to the endothelium," Blood 98(6):1955-1962, Sep. 15, 2001.
Mauch, P., et al., "Hematopoietic Stem Cell Compartment: Acute and Late Effects of Radiation Therapy and Chemotherapy", Int. J. Radiation Oncology Biol. Phys., 31(5): 1319-1339, 1995.
McCavit et al., "An Analysis of the Pediatric Sub-Group From the Phase 2 Study of GMI-1070—A Novel Agent for the Vaso-Occlusive Crisis of Sickle Cell Anemia", Blood, 122(21):2206, Nov. 15, 2013.
McCavit et al., "An Analysis of the Pediatric Sub-Group From the Phase 2 Study of GMI-1070—A Novel Agent for the Vaso-Occlusive Crisis of Sickle Cell Anemia", ASH Annual Meeting 2013, Poster #56448, Dec. 8, 2013.
McEver et al., "Leukocyte trafficking mediated by selectin-carbohydrate interactions," J. Biol. Chem., 270 (19): 11025-11028 (1995).

(56) References Cited

OTHER PUBLICATIONS

McKenzie et al., "Low rhodamine 123 retention identifies long-term human hematopoietic stem cells with the Lin-CD34+CD38- population", Blood. 109, (2007), 543-545.

McLean et al., "Effects of a small molecule inhibitor of ICAM-1 and E-selectin expression on colonic inflammatory hyperalgesia and colitis" Digestive Disease 2003, Orlando FL, May 2003, abstract.

Menendez et al., "A Peptide Inhibitor of HIV-1 Neutralizing Antibody 2G12 is not a Structural Mimic of the Natural Carbohydrate Epitope on gp120," The FASEB Journal 22:1380-1382, May 2008.

Mimeault, et al., "Stem cells: a revolution in therapeutics-recent advances in stem cell biology and their therapeutic applications in regenerative medicine and cancer therapies," Clin. Pharmacol. Therapeutics, 82(3): 252-264 (2007).

Mitsiades, et al., "Preclinical studies in support of defibrotide for the treatment of multiple myeloma and other neoplasias," Clin. Cancer Res., 15 (4): 1210-1221 (2009).

Moore et al., "Evolution of an HIV Glycan-Dependent Broadly Neutralizing Antibody Epitope Through Immune Escape," Nature Medicine doi:10.1038/nm.2985 pp. 1-6, Oct. 2012.

Moore, "Waking Up HSCs: A new Role for E-Selectin," Nat. Med., 18:16131614, (2012).

Mosley et al., "Recent Patents Regarding the Discovery of Small Molecule CXCR4 Antagonists," Expert Opin. Ther. Patents 19(1):23-38, 2009.

Mulligan et al., "Role of Endothelial-Leukocyte Adhesion Molecule 1 (ELAM-1) in Neutrophil-mediated Lung Injury in Rats," J Clin Invest.,88(4):1396-406, Oct. 1991.

Mulligan et al., "Selection for animal cells that express the *Escherichia coli* gene coding for xanthine-gunine phosphoribosyltransferase," Proc. Natl. Acad. Sci. USA 78:2072-2076, 1981.

Myers et al., "E-Selectin Inhibitor GMI-1271 Works in Combination with Low-Molecular Weight Heparin to Decrease Venous Thrombosis and Bleeding Risk in a Mouse Model", Blood, 124(21):593, Dec. 6, 2014.

Myers et al., "Novel E-Selectin Antagonist GMI-1271 Decreases Venous Thrombosis without Increased Bleeding Potential in a Mouse Model", ASH Annual Meeting 2012, Poster #53444, Dec. 10, 2012.

Myers et al., "Pan-Selectin Antagonist, GMI-1070 Decreases Venous Thrombosis in a Mouse Model", Blood, 118, Abstract #3273, Nov. 2011.

Myers JR. et al., "E-Selectin Inhibitor GMI-1271 Works in Combination with Low-Molecular Weight Heparin to Decrease Venous Thrombosis and Bleeding Risk in a Mouse Model," Proceedings of the 56th Annual Meeting of the American Society of Hematology, Abstract #593 Oral Presentation on Dec. 8, 2014, San Francisco, CA.

Myers JR. et al., "Novel E-Selectin Antagonist GMI-1271 Decreases Venous Thrombosis without Increased Bleeding Potential in a Mouse Model," Blood, 120(21), Abstract #3422, Nov. 16, 2012.

Myers JR. et al., "Novel E-Selectin Antagonist GMI-1271 Decreases Venous Thrombosis without Increased Bleeding Potential in a Mouse Model," Proceedings of the 54th Annual Meeting of the American Society of Hematology, Abstract #3422 Poster Presentation on Dec. 10, 2012, Atlanta, GA.

Nagel, R. L., "A Knockout of a Transgenic Mouse-Animal Models of Sickle Cell Anemia," The New England Journal of Medicine 339:194-195, Jul. 16, 1998.

Narita, T. et al., "Corticosteroids and medroxyprogesterone acetate inhibit the induction of breast cancer cells," Anticancer Research, 15(6B): 2523-2527 (1995)—Abstract.

Narum, Tetsuo et al., "Synthesis and Biological Evaluation of Selective CXCR4 Antagonists Containing Alkene Dipeptide Isosteres," Organic & Biomolecular Chemistry, 8(3): 616-621(Feb. 7, 2010).

Natarajan, M.M. et al., "Adhesion of sickle red blood cells and damage to interleukinlbeta stimulated endothelial cells underflow in vitro," Blood 87:4845-4852, 1996.

Natoni et al., "E-Selectin Ligand Expression Increases with Progression of Myeloma and Induces Drug Resistance in a Murine Transplant Model, Which Is Overcome by the Glycomimetic E-Selectin Antagonist, GMI-1271," Blood, 126(23), Abstract#1805, Dec. 3, 2015.

Natoni et al., "E-Selectin Ligand Expression Increases with Progression of Myeloma and Induces Drug Resistance in a Murine Transplant Model, Which Is Overcome by the Glycomimetic E-Selectin Antagonist, GMI-1271," Proceedings of the 57th Annual Meeting of the American Society of Hematology, Abstract #1805 Poster Presentation on Dec. 5, 2015 in Orlando, FL.

Natoni et al., "Multiple Myeloma Cells Express Functional E-Selectin Ligands Which Can be Inhibited Both in-Vitro and in-Vivo Leading to Prolongation of Survival in a Murine Transplant Model", Blood, 124(21):4718, Dec. 6, 2014.

Natoni et al., Multiple Myeloma Cells Express Functional E-Selectin Ligands Which Can be Inhibited Both in vitro and in vivo Leading to Prolongation of Survival in a Murine Transplant Model, Proceedings of the 56th Annual Meeting of the American Society of Hematology, Abstract #4718 Poster Presentation on Dec. 8, 2014 in San Francisco, CA.

Newlaczyl et al., "Galectin-3—A jack-of-all-trades in cancer," Cancer Letters, 313, 123-128, 2011.

Nguyen, M et al., "Novel synthetic analogs 1-29 of sialyl Lewis X can inhibit angiogenesis in vitro and in vivo," Biochemical and Biophysical Research Communications, 228(3): 716-723 (Nov. 21, 1996).

Nicolaou et al., "Total Synthesis of the Tumor-Associated Le$^x$ Family of Glycosphingolipids," J. Amer. Chem. Soc. 112:3693-3695, 1990.

Noguchi, M. et al. "A minor E-selectin ligand, CD65, is critical for extravascular infiltration of acute myeloid leukemia cells," Leukemia Research, 25: 847-853 (2001).

Norman et al., "Sialyl Lewisx(sLex) and an sLex Mimetic, CGP69669A, Disrupt E-Selectin-Dependent Leukocyte Rolling In Vivo," Blood, 91(2):475-483 (Jan. 15, 1998).

Nudelman et al., "Novel Fucolipids of Human Adenocarcinoma: Disialosyl Le$^a$ Antigen (III$^4$FucIII$^6$NeuAcIV$^3$NeuAcLc$_4$) of Human Colonic Adenocarcinoma and the Monoclonal Antibody (FH7) Defining This Structure," J. Biol. Chem. 261 (12):5487-5495,1986.

Nutku, E. et al., "Ligation of Siglec-8: a selective mechanism for induction of human eosinophil apoptosis," Blood, 101(12): 5014-5020 (2003).

Oancea et al., "Alleviation of Acute Drug-Induced Liver Injury Following Acetaminophen Overdose by Therapeutic Blockade of E-Selectin in Preclinical Mouse Model," Gastroenterology, 150(4), Supplement 1, S1029, Abstract #358, (no oral presentation available) New Orleans, LA, Apr. 2016.

Obermajer, N. et al., "Design, synthesis and activity evaluation of mannose-based DC-SIGN antagonists," Molecular Diversity 15:347-360, May 2011.

Orhlein, R., "Carbohydrates and Derivatives as Potential Drug Candidates with Emphasis on the Selectin and Linear-B Area," Mini Reviews in Medicinal Chemistry 1: 349-361, 2001.

Oxford Textbook of Oncology, vol. 1, published 1995 by Oxford University Press, pp. 447-453.

Palcic et al., "A Bisubstrate Analog Inhibitor for α(1->2)-Fucosyltransferase," J. Biol. Chem. 264:17174-17181, 1989.

Palcic et al., "Enzymic Synthesis of Oligosaccharides Terminating in the Tumor-Associated Sialyl-Lewis-a Determinant," Carbohydr. Res. 190:1-11, 1989.

Palcic et al., "Regulation of N-Acetylglucosaminyltransferase V Activity. Kinetic Comparisons of Parental, Rous Sarcoma Virus-Transformed BHK, and L-Phytohemagglutinin-Resistant BHK Cells Using Synthetic Substrates and an Inhibitory Substrate Analog," J. Biol. Chem. 265:6759-6769, 1990.

Palma-Vargas, J.M. et al., "Small-Molecule Selectin Inhibitor Protects Against Liver Inflammatory Response After Ischemia and Reperfusion," J. Am. Coll. Surg. 185: 365-372, 1997.

Pamphilon et al., "Stem Cell Donation—What advice can be given to the donor?," Br. J. Haematol. 147(1):71-76, Oct. 2009, Author manuscript available at NIH Public access Aug. 1, 2012.

(56) References Cited

OTHER PUBLICATIONS

Patton, J. T. et al., "GMI-1070: a Small Glycomimetic, Pan-selectin Antagonist that Improves Blood Flow and Inhibits Blood Cell Adhesion in Sickle Mice," Abstract ID:ABSTY-5APYL-CA6TP-V2ET6, Sep. 2, 2005.
Payre, et al., "Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.
Payre, N. et al., "Chemoenzymatic Synthesis of a Modified Pentasaccharide as a Specific Substrate for a Sensitive Assay of a-Amylase by Fluorescence Quenching," Angew. Chem. Int. Ed. Engl. 34(11): 1239-1241 (1995).
Peacock et al., "Emergency Department Use of Galectin-3," Critical Pathways in Cardiology, 13(2), 73-77, 2014.
Pejchal R. et al., "A Potent and Broad Neutralizing Antibody Recognizes and Penetrates the HIV Glycan Shield," Science 334:1097-1103, Nov. 2011.
Pelus, "Peripheral blood stem cell mobilization: new regimens, new cells, where do we stand," Curr. Opin. Hematol., 15(4): 285-292 (2008).
Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).
Pentelute, Brad L. et al., "Chemica 1 1-16 dissection of protein translocation through the anthrax toxin pore," Angewandte Chemie, 50(10): 2294-2296 (Mar. 1, 2011).
Perret, S. et al., "Structural basis for the interaction between human milk oligosaccharides and the bacterial lectin PA-IIL of Pseudomonas aeruginosa," Biochem. J. 389: 325-332, 2005. cited by other.
Pezeshkian et al., "Leukemia Mediated Endothelial Cell Activation Modulates Leukemia Cell Susceptibility to Chemotherapy through a Positive Feedback Loop Mechanism," PLOS One, 8(4), e60823, 2013.
Phillips et al., "ELAM-1 Mediates Cell Adhesion by Recognition of a Carbohydrate Ligand, Sialyl-Le$^x$," Science 250:1130-1132, 1990.
Picker er al., "The Neutrophil Selectin LECAM-1 Presents Carbohydrate Ligands to the Vascular Selectins ELAM-1 and GMP-140," Cell 66:921-933, 1991.
Plasterk, R. H. A., et al., "The silence of the genes", Current Opinion in Genetics and Develooment 10 (2000), 562-567.
Price et al., "Breast Cancer Cells Metastasize to Bone through E-Selectin Positive Vascular Gateways", AACR Annual Meeting 2014, Poster #4831, Apr. 9, 2014.
Price et al., "Breast cancer cells metastasize to bone through E-selectin + vascular gateways," Cancer Research, 74(19 Supplement), 4831, Sep. 20, 2014.
Price et al., "Breast Cancer Cells Metastasize to Bone through E-Selectin Positive Vascular Gateways," Proceedings of the 105$^{th}$ Annual Meeting of the AACR, 4831, Apr. 5-9, 2014, San Diego, CA.
Price et al., "Metastatic breast cancer cell communication within a pro-dormancy bone marrow niche," Cancer Research, 75(15 Supplement), Abstract #3212, Aug. 2015.
Price et al., "Metastatic Breast Cancer Cell Communication Within a Pro-Dormancy Bone Marrow Niche," Proceedings of the 106$^{th}$ Annual Meeting of the American Association for Cancer Research, Abstract #3212, Apr. 18-22, 2015, Philadelphia, PA.
Prokazova et al., "Sialylated lactosylceramides. Possible inducers of non-specific immunosuppression and atherosclerotic lesions," European Journal of Biochemistry 172:1-6, 1988.
Purton et al., "Limiting Factors in Murine Hematopoietic Stem Cell Assays," Cell Stem Cell 1:263-270, Sep. 2007.
Rapoport et al., "Ganglioside Binding Pattern of CD33-Related Siglecs," Bioorganicand Medicinal Chemistry Letters, 13(4), 675-678, Feb. 2003.
Rapoport, E. et al., "Probing Sialic Acid Binding Ig-Like Lectins (Siglecs) with Sulfated Oligosaccharides," Biochemistry (Moscow), 71(5): 496-504 (2006).
Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.
Ravandi et al., "Characteristics and outcome of patients with acute myeloid leukemia refractory to 1 cycle of high-dose cytarabine-based induction chemotherapy," Blood 116(26), 5818-5823, 2010.
Reina et al., "1,2-Mannobioside Mimic: Synthesis, DC-SIGN Interaction by NMR and Docking, and Antiviral Activity," ChemMedChem 2:1030-1036, 2007.
Rice et al., "An Inducible Endothelial Cell Surface Glycoprotein Mediates Melanoma Adhesion," Science 246:1303-1306, 1989.
Richert et al., "Inhibition of CXCR4 by CTCE-9908 Inhibits Breast Cancer Metastasis to Lung and Bone," Oncology Reports 21:761-767, 2009.
Roberge, J. Y., et al., "A Strategy for a Convergent Synthesis of N-Linked Glycopeptides on a Solid Support", Science 269(5221), (1995), 202-204.
Röllig et al., "Long-Term Prognosis of Acute Myeloid Leukemia According to the New Genetic Risk Classification of the European LeukemiaNet Recommendations: Evaluation of the Proposed Reporting System," Journal of Clinical Oncology, 29(20), 2758-2765, 2011.
Rood et al., "E-Selectin and Very Late Activation Antigen-r Mediate Adhesion of Hematopoietic Progenitor Cells to Bone Marrow Endothelium," Ann Hematol, 79:477-484, (2000).
Ruoslahti et al., "New Perspectives in Cell Adhesion: RGD and Integrins," Science 238:491-497, 1987.
Sackstein, "The Biology of CD44 and HCELL in Hematopoiesis: The 'Step 2-Bypass Pathway' and Other Emerging Perspectives", Current Opinion in Hematology, 18(4):239-248 (2011).
Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.
Salameh et al., "1H-1,2,3-Triazol-1-yl thiodigalactoside derivatives as high affinity galectin-3 inhibitors," Bioorganic & Medicinal Chemistry, 18, 5367-5378, 2010.
Sanz et al., "Roflumilast inhibits leukocyte-endothelial cell interactions, expression of adhesion molecules and microvascular permeability", British Journal of Pharmacology. 152(4), (2007), 481-492.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scanlan et al., "Exploiting the Defensive Sugars of HIV-1 for Drug and Vaccine Design," Nature 446:1038-1045, Apr. 2007.
Scanlan et al., "The Broadly Neutralizing Anti-Human Immunodeficiency Virus Type 1 Antibody 2G12 Recognizes a Cluster of a1-2 mannose Residues on the Outer Face of gp120," Journal of Virology 76:7306-7321, Jul. 2002.
Scharfman et al., "Pseudomonas aeruginosa binds to neoglycoconjugates bearing mucin carbohydrate determinants and predominantly to sialyl-Lewis x conjugates," Glycobiology 9(8): 757-764, 1999.
Scharfman et al., "Recognition of Lewis x Derivatives Present on Mucins by Flagellar Components of Pseudomonas aeruginosa," Infection and Immunity 69(9): 5243-5248, Sep. 2001.
Schief et al., "Challenges for Structure-Based HIV Vaccine Design," Current Opinion in HIV and AIDS 4:431-440, 2009.
Schwizer et al. "Pre-organization of the Core Structure of E-Selectin Antagonist," Chemistry—A European Journal, 18(5): 1342-1351 (Jan. 2012).
Shamay et al., "E-selectin binding peptide-polymer-drug conjugates and their selective cytotoxicity against vascular endothelial cells," Biomaterials, 30, 6460-6468, 2009.
Shan, M. et al., "HIV-1 gp120 Mannoses Induce Immunosuppressive Responses from Dendritic Cells," PLoS Pathogens 3(11):e169 1637-1650, Nov. 2007.
Sheen-Chen et al., "Serum levels of soluble E-selectin in women with breast cancer," British Journal of Surgery, 91, 1578-1581, 2004.

(56) References Cited

OTHER PUBLICATIONS

Shitara et al., "Application of Anti-Sialyl Le$^a$ Monoclonal antibody, KM231, for Immunotherapy of Cancer," Anticancer Res. 11:2003-2014, 1991.
Simanek et al. "Selectin-carbohydrate interactions: from natural ligands to designed mimics", Chemical Reviews vol. 98, No. 2, pp. 833-862, Jan. 1998.
Simon et al, "Effects of Selectin Antagonist GMI-1070 on the Activation State of Leukocytes in Sickle Cell Patients not in Crisis" ASH Annual Meeting 2010, Poster#32407, Dec. 6, 2010.
Simon et al., "Inhibition of E-Selectin Inflammatory Function by the Glycomimetic GMI-1070" Blood, 118, Abstract #851, Nov. 2011.
Simon et al., "Mightier than the sickle cell (editorial)", Blood, 116(10), 1633, Sep. 9, 2010.
Singh et al., "Evaluation of a CXCR4 Antagonist in a Xenograft Mouse Model of Inflammatory Breast Cancer," Clin. Exp. Metastasis 27:233-240, Mar. 2010.
Sipkins et al., "In Vivo Imaging of Specialized Bone Marrow Endothelial Microdomains for Tumor Engraftment," Nature Pub. Group GB 435 (7044):969-973, Jun. 2005.
Siuzdak et al., "Examination of the Sialyl Lewis X—Calcium Complex by Electrospray Mass Spectrometry," Bioorganic & Medicinal Chemistry Letters 4(24): 2863-2866, 1994.
Solovey et al., "Circulating Activated Endothelial Cells in Sickle Cell Anemia," The New England Journal of Medicine 337:1584-1590, Nov. 27, 1997.
Solovey et al. "Modulation of endothelial cell activation in sickle cell disease: a pilot study," Blood, 97(7): 1937-1941 (Apr. 2001).
Sprengard et al., "Synthesis and Biological Activity of Novel Sialyl-Lewis$^x$ Conjugates," Bioorganic & Medicinal Chemistry Letters 6(5): 509-514, 1996.
Stahn et al., Multivalent sialyl Lewis x ligands of definite structures as inhibitors of E-selectin mediated cell adhesion, Glycobiology, vol. 8, No. 4, 1998, pp. 311-319.
Stanley et al., "The LEC11 Chinese Hamster Ovary Mutant Synthesizes N-Linked Carbohydrates Containing Sialylated, Fucosylated Lactosamine Units. Analysis by One- and Two-Dimensional HNMR Spectroscopy," J. Biol. Chem. 263(23):11374-11381, 1988.
Steele et al., "#4503 a Small Molecule Glycomimetic Antagonist of E-selectin (GMI-1271) Prevents Pancreatic Tumor Metastasis and Offers Improved Efficacy of Chemotherapy," Proceedings of the 105$^{th}$ Annual Meeting of the American Association for Cancer Research, Abstract #4503, Apr. 5-9, 2014, San Diego, CA.
Steele et al., "425 a small molecule glycomimetic antagonist of E-selectin and CXCR4 (GMI-1359) prevents pancreatic tumor metastasis and offers improved chemotherapy" Cancer Research, Aug. 2015.
Steele et al., "425 a Small Molecule Glycomimetic Antagonist of E-selectin and CXCR4 (GMI-1359) Prevents Pancreatic Tumor Metastasis and Offers Improved Chemotherapy," Proceedings of the 106$^{th}$ Annual Meeting of the American Association for Cancer Research, Abstract #425, Apr. 18-22, 2015, Philadelphia, PA.
Steele et al., "A Small Molecule Glycomimetic Antagonist of E-selectin (GMI-1271) Prevents Pancreatic Tumor Metastasis and Offers Improved Efficacy of Chemotherapy", AACR Annual Meeting 2014, Poster #4503, Apr. 8, 2014.
Steele et al., "A Small Molecule Glycomimetic Antagonist of E-selectin (GMI-1271) Prevents Pancreatic Tumor Metastasis and Offers Improved Efficacy of Chemotherapy", Cancer Res, 74:Abstract 4503, Oct. 1, 2014.
Steele et al., "A small molecule glycomimetic antagonist of E-selectin and CXCR4 (GMI-1359) prevents pancreatic tumor metastasis and improves chemotherapy," Cancer Research, 75(15 Supplement), 425-426, Aug. 2, 2015.
Steele et al., "A small molecule glycomimetic antagonist of E-selectin and CXCR4 (GMI-1359) delays pancreatic tumor metastasis and significantly alters the pancreatic tumor microenvironment," Proceedings of the 107$^{th}$ Annual Meeting of the American Association for Cancer Research, Abstract #902, Apr. 16-20, 2016, New Orleans, LA.
Steele et al., "Abstract 4503: A small molecule glycomimetic antagonist of E-selectin (GMI-1271) prevents pancreatic tumor metastasis and offers a novel treatment for improved efficacy of chemotherapy," Cancer Research, 74(19 Supplement), Abstract #4503, Oct. 2014.
Stephens et al.,"The construction of highly efficient and versatile set of mammalian expression vectors," Nucleic Acids Research. 17:7110, 1989.
Stevenson et al., "Differential metastasis inhibition by clinically relevant levels of heparins," Clin. Cancer Res. 11(19): 7003-7011 (2005).
Streeter et al., "Immunohistologic and Functional Characterization of a Vascular Addressin Involved in Lymphocyte Homing into Peripheral Lymph Nodes," Journal of Cell Biology 107:1853-1862, 1988.
Stroud et al. ,"Extended Type 1 Chain Glycosphingolipids: Dimeric Le$^a$ (III$^4$V4Fuc$_2$Lc$_6$) as Human Tumor-associated Antigen," J. Biol. Chem. 266(13):8439-8446, 1991.
Styles et al., GMI-1070, a Pan-Selectin Inhibitor: Safety and PK in a Phase 1/2 Study in Adults with Sickle Cell Disease, ASH Annual Meeting 2010, Poster #31824, Dec. 4, 2010.
Sudhoff et al., "Cutting Edge Communication: Circulating Endothelial Adhesion Molecules (sE-Selectin, sVCAM-1 and SICAM-1) During rHuG-CSF-Stimulated Stem Cell Mobilization," Jour. Hematother. & Stem Cell Res., 11:147-151 (2002).
Supplementary European Search Report in EP 03739223 dated Jan. 16, 2009.
Suzuma et al., "Contribution of E-Selectin to Cellular Infiltration during Endotoxin-Induced Uveitis," Invest. Ophthalmol. Vis. Sci., 39: 1620-1630 (1998).
Svenson et al., "Coupling of Acid Labile *Salmonella* Specific Oligosaccharides to Macromolecular Carriers," J. Immunol. Meth. 25:323-335, 1979.
Symon et al., "Selectins and their Counter receptors: a bittersweet attraction," Thorax, 51: 1155-1157 (1996).
Tabarani et al., "Mannose Hyperbranched Dendritic Polymers Interact with Clustered Organization of DC-SGIN and Inhibit gp120 Binding," FEBS Letters 580:2402-2408, Mar. 2006.
Takada et al., "Adhesion of Human Cancer Cells to Vascular Endothelium Mediated by a Carbohydrate Antigen, Sialyl Lewis A$^1$," Biochem. Biophys. Res. Commun. 179(2):713-719, 1991.
Takahashi et al., "Design and Synthesis of a Water-Soluble Taxol Analogue : Taxol-Sialyl Conjugate," Bioorg. & Med. Chem. Letters 8:113-116, 1998.
Takeichi, "Cadherins: a molecular family essential for selective cell-cell adhesion and animal morphogenesis," Trends Genet. 3(8):213-217, 1987.
Tamamura, et al., "Identification of a New Class of Low Molecular Weight Antagonists against the Chemokine Receptor CXCR4 Having the Dipicolylamine-Zinc(II) Complex Structure" J. Med. Chem., 49:3412-3415 (2006).
Tanaka et al., "Azamacrocyclic Metal Complexes as CXCR4 Antagonists," ChemMedChem, 6:834-839 (2011).
Taniguchi et al., "Serum Levels of Galectin-3: Possible Association with Fibrosis, Aberrant Angiogenesis, and Immune Activation in Patients with Systemic Sclerosis," The Journal of Rheumatology, 39(3), 539-544, Mar. 2012.
Tedder et al., "The selectins: vascular adhesion molecules," FASEB J, 9(10): 866-73 (1995).
Tejler et al., "Fragment-based development of triazole-substituted O-galactosyl aldoximes with fragment-induced affinity and selectivity for galectin-3," Organic & Biomolecular Chemistry, 19(7), 3982-3992, 2009.
Tejler et al., "Synthesis of galactose-mimicking 1H-(1,2,3-triazol-l-yl)-mannosides as selective galectin-3 and 9N inhibitors," Carbohydrate Research, 342(12-13), 1869-1875, 2007.
Telen et al., "GMI 1070: Reduction in Time to Resolution of Vaso-Occlusive Crisis and Decreased Opioid Use in a Prospective, Randomized, Multi-Center Double Blind, Adaptive Phase 2 Study in Sickle Cell Disease" Blood, 122(21):776, Nov. 15, 2013.
Telen et al., "Randomized phase 2 study of GMI-1070 in SCD: reduction in time to resolution of vaso-occlusive events and decreased opioid use", Blood, 125(17):2656-2664, Apr. 23, 2015.

(56) References Cited

OTHER PUBLICATIONS

The Merck Manual of Diagnosis and Therapy, Seventeenth Edition, published 1999 by Merck Research Laboratories, pp. 397, 398, 948,949, 1916, 1979-1981.
Thoma G. et al., "A readily Available, Highly Potent E-Selectin Antagonist," Angew. Chem. Int. Ed. 40(19): 3644-3647, 2001.
Thoma, G et al., "Nanomolar E-selectin inhibitors: 700-fold potentiation of affinity by multivalent ligand presentation," Journal of the American Chemical Society, 123(41): 10113-10114 (Oct. 17, 2001).
Thoma, G. et al., "Preorganization of the Bioactive Conformation of Sialyl Lewis$^x$ Analogues Correlates with Their Affinity to E-Selectin," Angew. Chem. Int. Ed. 40(10): 1941-1945, 2001.
Thoma, G. et al., "Synthesis and biological evaluation of a potent E-selectin antagonist," J. Med. Chem. 42 (23): 4909-4913, Nov. 18, 1999.
Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.
Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.
Titz et al., "Is adamantine a suitable substituent to pre-organize the acid orientation in E-selectin antagonists?", Bioorganic & Medicinal Chemistry, 16 (2008), 1046-1056.
Titz et al., "Mimetics of Sialyl Lewis$^x$: The Pre-Organization of the Carboxylic Acid is Essential for Binding to Selectins", Chimia, 61:194-197, 2007.
Titz, A. et al., "Probing the carbohydrate recognition domain of E-selectin: The importance of the acid orientation in sLex mimetics," Bioorg. Med. Chem., 18(1): 19-27 (2010).
Todderund et al., "BMS-190394, a Selectin Inhbitor, Prevents Rat Cutaneous Inflammatory Reactions," J Pharmacal Exp Ther., 282(3):1298-304, Sep. 1997.
Toepfer et al., "Synthesis of Novel Mimetics of the Sialyl Lewis X Determinant," Tetrahedron Letters, vol. 36, No. 50, pp. 9161-9164, 1995.
Togel et al., "Administered mesenchymal stem cells protect against ischemic acute renal failure through differentiation-independent mechanisms," Am. J. Physical Renal Physiol., 289:F31-42, Jul. 2005.
Totani, K. et al., "Chemoenzymatic synthesis and application of glycopolymers containing multivalent sialyloligosaccharides with a poly(L-glutamic acid) backbone for inhibition of infection by influenza viruses," Glycobiology, 13(5): 315-326 (2003).
Trouet et al., "A covalent linkage between daunorubicin and proteins that is stable in serum and reversible by lysosomal hydrolases, as required fora lysosomotropic drug-carrier conjugate: In vitro and in vivo studies," Proc. Natl. Acad. Sci. USA 79:626-629, 1982.
Turhan, et al., "Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," The American Journal of Pathology, 169(6): 1901-1909 (Dec. 2006).
Tyrrell, D. et al. "Structural requirements for the carbohydrate ligand of E-selectin," PNAS, 88: 10372-10376 (Nov. 1991).
Ueda et al., "Structure-Activity Relationships of Cyclic Peptide-Based Chemokine Receptor CXCR4 Antagonists: Disclosing the Importance of Side-Chain and Backbone Functionalities," J. Med. Chem. 50:192-198, 2007.
Van Der Velde et al., "Galectin-3 and sST2 in prediction of left ventricular ejection fraction after myocardial infarction," Clinica Chimica Acta, 452, 50-57, Jan. 2016.
Venkataraman et al., "Reawakening Retrocyclins: Ancestral Human Defensins Active Against HIV-1," Plos Biology, 7(4): 720-729 (Apr. 2009).

Wai, "Blockade of Chemokine (C-X-C motif) Receptor 4 for the Inhibition of Hepatocellular Carcinoma Metastasis," A Thesis, in partial fulfillment of requirements for Ph.D. Degree at the Univ. of Hong Kong, Jun. 2008.
Waldmann et al., "Synthesis of 2-Acetamindo-2-Deoxyglucosylasparagine Glyco-Tripeptide and -Pentapeptides by Selective C- and N-Terminal Elongation of the Peptide Chain," Carbohydrate Research 196: 75-93, 1990.
Walker et al., "Rapid Development of Glycan-Specific, Broad, and Potent Anti-HIV-1 gp120 Neutralizing Antibodies in an R5 SIV/HIV Chimeric Virus Infected Macaque," Proceedings of the National Academy of Sciences 108(50):20125-20129, Dec. 2011.
Walsh, "Novel Therapies for Asthma—Advances and Problems," Current Pharmaceutical Design, 11(23): 3027-3038 (2005).
Walz et al., "Recognition by ELAM-1 of the Sialyl-Le$^x$ Determinant on Myeloid and Tumor Cells," Science 250:1132-1135, 1990.
Wang et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.
Wang et al., "Effect of ginsenoside rg1 and rh1 on the expression of hla-dr, cd25, cd44, cd11c and e-selectin on dendritic cell," Zhongguo Mianyixue Zazhi, 23(1): 46-48 (2007)—Abstract.
Wang et al., "Galectin-3 promotes HIV-1 budding via association with Alix and Gag p6," Glycobiology, 24(11), 1022-1035, 2014.
Wang et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.
Ward et al., "Blocking of adhesion molecules in vivo as anti-inflammatory therapy," Immunology 1: 165-171, 1994.
Wesche et al., "Characterization of membrane translocation by anthrax protective antigen," Biochemistry, 37(45): 15737-15746 (Nov. 10, 1998).
Whisler et al., "Regulation of Lymphocyte Responses by Human Gangliosides. I. Characteristics of Inhibitory Effects and the Induction of Impaired Activation," Journal of Immunology 125(5):2106-2111, 1980.
Wicklein et al., "E- and P-Selectins Are Essential for Repopulation of Chronic Myelogenous and Chronic Eosinophilic Leukemias in a Scid Mouse Xenograft Model," PLOS One, 8(7), e70139, 2013.
Winkler et al., "Absence of E-selectin at vascular niche delays hematopoietic stem cell turn-over," Blood, 110(11):188A, Nov. 2007.
Winkler et al., "Absence or blockage of E-Selectin-Mediated Cell Adhesion Delays Hematopoietic Stem Cell", ASH Annual Meeting 2009, Abstract #564, Nov. 2009.
Winkler et al., "Absence or blockage of E-Selectin-Mediated Cell Adhesion Delays Hematopoietic Stem Cell", Blood, 114(22), Abstract#564, Dec. 7, 2009.
Winkler et al., "Adhesion of E-selectin promotes growth inhibition and apoptosis of human and murine hematopoietic progenitor cells independent of PSGL-1," Blood, 103(5):1685-92, Mar. 1, 2004.
Winkler et al., "Administration of E-selectin Antagonist GMI-1271 Improves Survival to High-Dose Chemotherapy by Alleviating Mucositis and Accelerating Neutrophil Recovery", Blood, 122(21):2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery", ASH Annual Meeting, Poster#63045, Dec. 8, 2013.
Winkler et al., "Administration of E-Selectin Antagonist GMI-1271 Improves Survival After High-Dose Chemotherapy by Alleviating Mucositis and Accelerating Neutrophil Recovery," Blood, 122(21), Abstract #2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery," Proceedings of the 55$^{th}$ Annual Meeting of the American Society of Hematology, Abstract #2266, Poster Presentation on Dec. 9, 2013, New Orleans, LA.

(56) References Cited

OTHER PUBLICATIONS

Winkler et al., "Mobilisation of Reconstituting HSC Is Boosted by Synergy Between G-CSF and E-Selectin Antagonist GMI-1271", Blood, 124(21):317, Dec. 6, 2014.
Winkler et al., "Mobilisation of Reconstituting HSC Is Boosted by Synergy Between G-CSF and E-Selectin Antagonist GMI-1271," Blood, 124(21), Abstract#317, Dec. 6, 2014.
Winkler et al., "Mobilization of CD8+ Central Memory T-Cells with Enhanced Reconstitution Potential in Mice by a Combination of G-CSF and GMI-1271-Mediated E-Selectin Blockade," Blood, 126(23), Abstract#512, Dec. 3, 2015.
Winkler et al., "Mobilization of CD8+ Central Memory T-Cells with Enhanced Reconstitution Potential in Mice by a Combination of G-CSF and GMI-1271-Mediated E-Selectin Blockade," Proceedings of the 57th Annual Meeting of the American Society of Hematology, Abstract #512, Oral Presentation, Dec. 7, 2015, Orlando, FL.
Winkler et al., "Vascular E-Selectin Protects Leukemia Cells from Chemotherapy by Directly Activating Pro-Survival NF-Kb Signalling—Therapeutic Blockade of E-Selectin Dampens NF-Kb Activation," Blood, 128(22), Abstract #2823, Dec. 2, 2016.
Winkler et al., "Vascular Niche E-Selectin Protects Acute Myeloid Leukemia Stem Cells from Chemotherapy", Blood, 124(21):620, Dec. 6, 2014.
Winkler et al., "Vascular Niche E-Selectin Protects Acute Myeloid Leukaemia Stem Cells from Chemotherapy," Blood, 124(21), Abstract #620, Dec. 6, 2014.
Winkler et al., "Vascular Niche E-Selectin Regulates Hematopoietic Stem Cell Dormancy, Self Renewal and Chemoresistance", Nature Medicine, doi:10.1038/nm2969, Oct. 21, 2012.
Winkler et al., "Vascular niche E-selectin regulates hematopoietic stem cell dormancy, self renewal and chemoresistance," Nature Medicine, 18(11), 1651-1657, 2012.
Winkler et al., "Vascular niche E-selectin regulates hemopoietic stem cell dormancy, self-renewal and chemoresistance," Nature Medicine, 18(11), 1651-1657, Supplementary Figures and Table, 2012.
Winkler, "Mobilisation of reconstituting HSC is boosted by E-selectin antagonist GMI-1271," Proceedings of the 56th Annual Meeting of the American Society of Hematology, Abstract #317, Oral Presentation on Dec. 7, 2014, San Francisco, CA.
Winkler, "Vascular bone marrow niches protect AML Leukaemia stem cells from chemotherapy," Proceedings of the 56th Annual Meeting of the American Society of Hematology, Abstract #620, Oral Presentation on Dec. 8, 2014, San Francisco, CA.
Winnard, P. et al., "Real time non-invasive imaging of receptor-ligand interactions in vivo," J. Cell. Biochem., 90: 454-463 (2003).
Winzer, K. et al. "The Pseudomonas aeruginosa Lectins PA-IL and PA-IIL are Controlled by Quorom Sensing and by RpoS," J. Bacteriol. 182(22): 6401-6411 (2000).
Witz, "The involvement of selectins and their ligands in tumor-progression," Immunol. Lett., 104(1-2): 89-93 (2006).
Wu et al., "Salivary Agglutinin Inhibits HIV Type 1 Infectivity through Interaction with Viral Glycoprotein 120," AIDS Research and Human Retroviruses, 19(30), 201-209, 2003.
Wu, B. et al. "Structures of the CXCR4 Chemokine GPCR with Small-Molecule and Cyclic Peptide Antagonists," Science, 330(6007): 1066-1071 (Nov. 2010).
Wun et al., "Pan-Selectin Antagonist Rivipansel (GMI-1070) Reduces Soluble E-Selectin Levels While Improving Clinical Outcomes in SCD Vaso-Occlusive Crisis" Blood, 124(21):2704, Dec. 6, 2014.
Xu, J. et al., "Molecular insights and therapeutic targets for diabetic endothelial dysfunction," Circulation, 120: 1266-1286 (2009).
Yamazaki, F. et al,. "Synthesis of an appropriately protected core glycotetraoside, a key intermediate for the synthesis of 'bisected' complex-type glycans of a glycoprotein," Carbohydrate Research 201: 15-30, 1990.
Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang et al., "3790 The Dual E-Selectin/CXCR4 Inhibitor, GMI-1359, Enhances Efficacy of Anti-Leukemia Chemotherapy in FLT3-ITD Mutated Acute Myeloid Leukemia," Blood, 126(23), Abstract #3790, Dec. 3, 2015.
Zhang et al., "The Dual E-selectin/CXCR4 Inhibitor, GMI-1359, Enhances Efficacy of Chemotherapy in FLT3-ITD-Mutated Acute Myeloid Leukemia," Proceedings of the 57th Annual Meeting of the American Society of Hematology, Abstract #3790, Poster Presentation, Dec. 7, 2015, Orlando, FL.
Zhang et al., "The E-selectin/CXCR4 Inhibitor GMI-1359 Effectively Mobilizes Bone Marrow Leukemia Cells and Enhances FLT3 Inhibitor Efficacy in a Murine AML Model," Proceedings of the 107th Annual Meeting of AACR, 3284, Apr. 16-20, 2016, New Orleans, LA.
Zhang, Z. et al. "CXCR4 but not CXCR7 is mainly implicated in ocular leukocyte trafficking during ovalbumin-induced acute uveitis," Experimental Eye Research, 89: 522-531 (2009).
Zhao T. et al. "Targeting human CD34+ hematopoietic stem cells with anti-CD45 x antimyosin lightchain bispecific antibody preserves cardiac function in myocardial infarction" Journal of Applied Physiology, 10(6):1793-1800 (2008).
Zheng, CX et al. "The prognostic value of preoperative serum levels of Cea, CA19-9 and CA72-4 in patients with colorectal cancer," World J. Gastroentero, 7(3): 431-434 (2001).
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of ET-RA on expression of selectin on the surface of endothelial cell in mice with severe acute pancreatitis," Chongqing Yixue, 35(7): 624-626 (2006)—Abstract.
Zopf et al., "Affinity Purification of Antibodies Using Oligosaccharide-Phenethylamine Derivatives Coupled to Sepharose," Meth. Enzymol. 50:171-175, 1978.
Zuber et al., "Mouse models of human AML accurately predict chemotherapy response," Genes. Dev., 23 (7): 877-889 (2009).
Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," Journal of Virology 82(13):6359-6368, Jul. 2008.
Chemical Abstracts (STN), Accession No. 1997:584307, Inventor Name: Ito et al., Jul. 8, 1997.
Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.
Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kwong, P. D. et al., "Rational Design of Vaccines to Elicit Broadly Neutralizing Antibodies to HIV-1," Cold Spring Harbor Perspectives in Medicine 1-16, 2011.
Liu et al., "Targeting Regulatory T Cells in Tumors," FEBS J. 283:2731-2748, 2016.
Matsui, N. M. et al., "Heparin inhibits the flow adhesion of sickle red blood cells to P-selectin," Blood 100(10):3790-3796, Nov. 15, 2002.
Postow MA, et al., "Immune Checkpoint Blockade in Cancer Therapy," J. Clin. Oncol. 33(17):1974-1982, Jun. 10, 2015.

* cited by examiner

Group Summary

| Group # | Treatment | Dose (mg/kg/inj) | Schedule | Route | Toxicity | | | | Efficacy | | | | | |
|---|---|---|---|---|---|---|---|---|---|---|---|---|---|---|
| | | | | | Maximum Treatment-related Weight Loss (%) | Day of Max. Treatment-related Weight Loss | Recovery Time (days) | % Rx Related Deaths | Tumor Growth Delay (days) | % PD | % SD | % RD | % TFS | |
| 1 | Vehicle (saline) | 0.2mL/20g | QDx20; D3 start | IP | GAIN | NA | NA | 0 | NA | 100 | 0 | 0 | 0 | |
| 2 | GMI-1359 | 40.00 | QDx20; D3 start | IP | GAIN | NA | NA | 0 | 2.5 | 100 | 0 | 0 | 0 | |
| 3 | Isotype control antibody (LTF-2) | 10.00 | (Q3Dx2; 3off)x2.5; D3 start | IP | GAIN | NA | NA | 0 | 3.2 | 100 | 0 | 0 | 0 | |
| 4 | Anti-PD-L1 antibody (10F.9G2) | 10.00 | (Q3Dx2; 3off)x2.5; D3 start | IP | GAIN | NA | NA | 0 | 11.7 | 60 | 0 | 0 | 40 | |
| 5 | GMI-1359 + Isotype control antibody (LTF-2) | 40 + 10 | QDx20 + (Q3Dx2; 3off)x2.5; D3 start | IP + IP | GAIN | NA | NA | 0 | -0.1 | 100 | 0 | 0 | 0 | |
| 6 | GMI-1359 + Anti-PD-L1 antibody (10F.9G2) | 40 + 10 | QDx20 + (Q3Dx2; 3off)x2.5; D3 start | IP + IP | GAIN | NA | NA | 0 | 13.5 | 60 | 0 | 0 | 40 | |
| 7 | Vehicle (saline) | 0.2mL/20g | QDx12; D3 start | IP | GAIN | NA | NA | 0 | -3.3 | 80 | 20 | 0 | 0 | |
| 8 | GMI-1359 | 40.00 | QDx12; D3 start | IP | GAIN | NA | NA | 0 | -1.6 | 100 | 0 | 0 | 0 | |
| 9 | Isotype control antibody (LTF-2) | 10.00 | (Q3Dx2; 3off)x2; D3 start | NA | GAIN | NA | NA | 0 | NA | 80 | 0 | 0 | 20 | |
| 10 | Anti-PD-L1 antibody (10F.9G2) | 40 + 10 | (Q3Dx2; 3off)x2; D3 start | NA | GAIN | NA | NA | 0 | NA | 20 | 80 | 0 | 0 | |
| 11 | GMI-1359 + Isotype control antibody (LTF-2) | 40 + 10 | QDx12 + (Q3Dx2; 3off)x2; D3 start | NA | GAIN | NA | NA | 0 | NA | 100 | 0 | 0 | 0 | |
| 12 | GMI-1359 + Anti-PD-L1 antibody (10F.9G2) | 40 + 10 | QDx12 + (Q3Dx2; 3off)x2; D3 start | NA | GAIN | NA | NA | 0 | NA | 60 | 40 | 0 | 0 | |

GROUP SUMMARY ENDPOINT DEFINITIONS AND CALCULATION METHODS

| | |
|---|---|
| Maximum Mean BW Loss (%) | Calculated from the minimum of the mean BW curve (while there are greater than half the animals still surviving) for each group within the Rx period and out to 2 weeks after the end of Rx. |
| Day of Maximum Mean BW Loss | Calculated from the minimum of the mean BW curve (while there are greater than half the animals still surviving) for each group within the Rx period and out to 2 weeks after the end of Rx. |
| Recovery Time (days) | The number of days from the time of the minimum mean BW to recover the lost BW. Calculated only for animals which lost BW and later recovered the lost BW. |
| % Rx Related Deaths | % of mice in each group with treatment-related deaths. |
| Tumor Growth Delay (days) | The median time to evaluation size is calculated for each group (see Table 1). The tumor growth delay (TGD) is calculated by subtracting the median TGD for the control group from the median TGD for each treatment group. |
| Estimated Surviving Fraction (%) | Calculated using the observed net cell kill: Estimated surviving fraction = (100 / 10^Apparent Net Cell Kill) |
| Median Doubling Time (days) | Median doubling time for each group, based on doubling times calculated for each animal in the group from log-linear regressions on the tumor growth data. |
| % PD | % progressive disease was identified within the time frame of the experiment there was a >2x increase in tumor size when compared to the benchmark day (Day 9). |
| % SD | % stable disease was identified within the time frame of the experiment there is a period of time during which the tumor never gets to >2x the size observed on the benchmark day or never gets to less than 50% of the size vs the benchmark day. |
| % RD | % regressing disease was identified within the time frame of the experiment a tumor that is <50% of the size at the benchmark day. |
| % TFS | % of mice in each group that were tumor free survivors. |

FIG. 19

Time to Complete Response Rate in Tumor-bearing Mice Treated with anti-PD-L1 or anti-PD-L1 in Combination with GMI-1359

| Treatment Group | Complete response rate | Days post Rx initiation to complete response (median)[a] |
|---|---|---|
| α-PD-L1 | 40 | 14, 21, 25, 30 (23) |
| GMI-1359 + anti-PD-L1 | 40 | 7, 14, 14, 16 (14)[b] |

[a]Treatment completed day 20 post tumor injection
[b]p=0.0471 vs. anti-PD-L1 alone

*All mice achieving a complete response, rejected a subsequent challenge of CT-26*

*FIG. 20*

Competitive Binding Activity (IC50) of GMI-1359 Against
E-selectin and CXCR4

GMI-1359 was assessed for inhibition of sialyl Le$^x$ binding to immobilized
E-selectin and CXCR4 antibody binding to Raji cells. IC50's (µM) were determined.

| Compound | E-Selectin | CXCR4 |
|----------|------------|-------|
| GMI-1359 | 1.0        | 0.5   |

FIG. 21

Ratio of COS/Regulatory T cells in
Spleen and Tumor on Study Day 5

| Treatment Group | Spleen | Tumor |
|---|---|---|
| Saline | 0.97 | 7.07 |
| GMI-1359 | 0.88 | 5.33 |
| Ig control | 1.00 | 2.93 |
| Anti-PD-L1 | 0.55 | 9.15 |
| GMI-1359 + Ig control | 0.81 | 4.60 |
| GMI-1359 + anti-PD-L1 | 0.69 | 18.71 |

*FIG. 23*

| Group | Tumor Growth Delay (days) | % Progressive Disease | % Regressing Disease | % Tumor-free survivors |
|---|---|---|---|---|
| Saline | NA | 100 | 0 | 0 |
| GMI-1359 | 2.5 | 100 | 0 | 0 |
| Ig control | 3.2 | 100 | 0 | 0 |
| Anti-PD-L1 | 11.7 | 60 | 40 | 40 |
| GMI-1359 + Ig control | -0.1 | 100 | 0 | 0 |
| GMI-1359 + anti-PD-L1 | 13.5 | 60 | 40 | 40 |

*FIG. 24A*

COMBINATION OF T-CELL CHECKPOINT INHIBITORS WITH INHIBITORS OF E-SELECTIN OR CXCR4, OR WITH HETEROBIFUNCTIONAL INHIBITORS OF BOTH E-SELECTIN AND CXCR4

This application is a United States national stage application filed under 35 U.S.C. § 371 of International Patent Application No. PCT/US2017/045690 accorded an international filing date of Aug. 7, 2017; which application claims priority to U.S. Provisional Application Nos. 62/372,116, filed Aug. 8, 2016, 62/418,722, filed Nov. 7, 2016, and 62/417,045, filed Nov. 3, 2016; the disclosures of which are incorporated herein by reference.

Compositions and methods for the treatment of diseases, disorders, and/or conditions associated with the increased regulatory T lymphocyte cell ($T_{reg}$ cell) function, comprising the administration of T-cell checkpoint inhibitors in combination with E-selectin inhibitors, CXCR4 receptor inhibitors, and/or heterobifunctional inhibitors which comprise at least one E-selectin inhibitor linked to at least one CXCR4 receptor inhibitor, are disclosed. One such disease, disorder, and/or condition is cancer.

It is now understood that cancer tumors are not masses of solely malignant cells, but instead comprise some malignant cells and some recruited normal cell types. Liu et al., "Targeting Regulatory T Cells in Tumors," *FEBS J.* 283: 2731-48, at 2731 (2016). The malignant cells and normal cells both play roles in promoting tumor growth and metastasis. Id. One of the normal cells that supports cancer progression in the tumor microenvironment are $T_{reg}$ cells.

$T_{reg}$ cells down-regulate other immune cells, thereby playing an important role in, for example, preventing autoimmunity. In the tumor microenvironment, malignant cells can attract $T_{reg}$ cells and increase the local concentration of cytokines expressed by $T_{reg}$ cell that down-regulate other immune cells. $T_{reg}$ cells are induced and maintained by immunoregulatory receptors, such as PD-1. $T_{reg}$ cells also respond to homing signals within the inflamed tumor microenvironment that include the endothelial cell surface protein, E-selectin, and the CXCR4 ligand, SDF-1. Using these pathways, the cancer cells use $T_{reg}$ cells to prevent other immune cells from attacking the cancer. Thus, although the immune system is often able to produce a response against the malignancy, due at least in part to the influence of $T_{reg}$ cells, this response is often insufficient to eliminate the tumor.

This realization led to the interest in blocking immunoregulatory receptors called checkpoint proteins on T cells. By blocking the checkpoint proteins on T cells, the T cells are no longer able to down-regulate the rest of the immune response, and the immune cells are able to attack the malignant cancer cells. FDA approval has already been granted to two of these immune checkpoint inhibitors, nivolumab (Opdivo®) and ipilimumab (Yervoy®). Nivolumab inhibits the activity of a protein receptor called PD-1 on T cells and ipilimumab binds to a checkpoint protein on the surface of T cells called CTLA-4. These T-cell checkpoint inhibiting drugs may be used in combination with standard cancer treatments, such as radiation therapy and chemotherapy.

Success targeting CTLA-4 has created enthusiasm for clinical approaches targeting other immunologic checkpoints, namely PD-1/PD-L1. PD-1 is a negative regulator of T-cell activity that limits the activity of T cells at a variety of stages of the immune response when it interacts with its two ligands PD-L1 and PD-L2. When engaged by ligand, through phosphatase activity, PD-1 inhibits kinase signaling pathways that normally lead to T-cell activation. Mice deficient in PD-1 have a distinct autoimmune phenotype from mice deficient in CTLA-4. Perhaps this finding is unsurprising because, unlike CTLA-4, which is primarily believed to regulate immune responses early in T-cell activation, PD-1 is primarily believed to inhibit effector T-cell activity in the effector phase within tissue and tumors. PD-1 is expressed on many immunologic cells, including B cells and natural killer cells, and therapeutic blockade of the PD-1 pathway may influence the function of these cells as well.

A number of antibodies that disrupt the PD-1 axis have entered clinical development. Although the various antibodies differ in structure, they can largely be broken down into the following two main categories: those that target PD-1 (nivolumab, Bristol-Myers Squibb; pembrolizumab, Merck, Whitehouse Station, N.J.; pidilizumab, CureTech, Yavne, Israel) and those that target PD-L1 (MPDL3280A, Genentech, South San Francisco, Calif.; MEDI4736, MedImmune/AstraZeneca; BMS-936559, Bristol-Myers Squibb; MSB0010718C, EMD Serono, Rockland, Mass.). AMP-224 (Amplimmune, Gaithersburg, Md./GlaxoSmithKline, Philadelphia, Pa.) is a PD-L2 fusion protein that does not directly target PD-1 or PD-L1, but instead is believed to deplete PD-1-positive T cells.

The T-cell checkpoint inhibitors may be useful in treating cancer, but the course of treatment is usually lengthy and there are several side-effects. Furthermore, treatment with T-cell checkpoint inhibitors only target one aspect of the cancer cells' commandeering of the immune system—the inducement and maintenance of $T_{reg}$ cells—and it does not address the recruitment of the T cells to the tumor microenvironment by E-selectin and/or SDF-1.

Accordingly, there is an unmet need for additional compositions and treatments for suppressing $T_{reg}$ cell function for the treatment of cancer, in particular, compositions and treatments that address the E-selectin and/or SDF-1 related pathways. There is also an unmet need for additional compositions and treatments for suppressing $T_{reg}$ cell function for the treatment of other diseases, disorders, and/or conditions related to over-active or numerous $T_{reg}$ cells, such as bacterial and viral infections including sepsis, septic conditions, and HIV infection.

BRIEF DESCRIPTION OF DRAWINGS

Those of ordinary skill in the art will understand that the drawings, described below, are for illustrative purposes only. The drawings are not intended to limit the scope of the present teachings in any way.

Figure 4A:
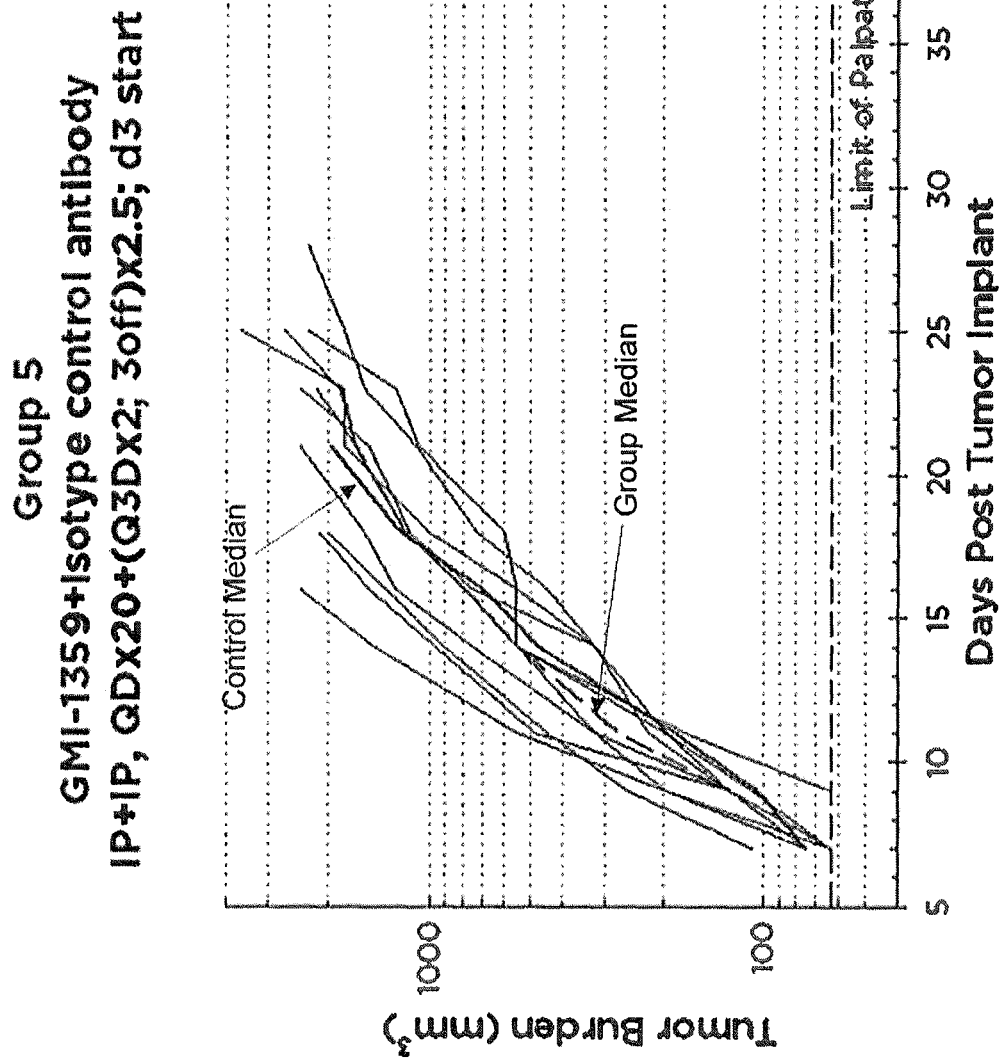
FIGS. 4A-D are graphs of the tumor growth of individual mice of group 5 (GMI-1359 and LTF-2 antibody, FIG. 4A); group 6 (GMI-1359 and anti-PD-L1 antibody treatment, FIG. 4B); group 7 (saline control, FIG. 4C); and group 8
Figure 4B:
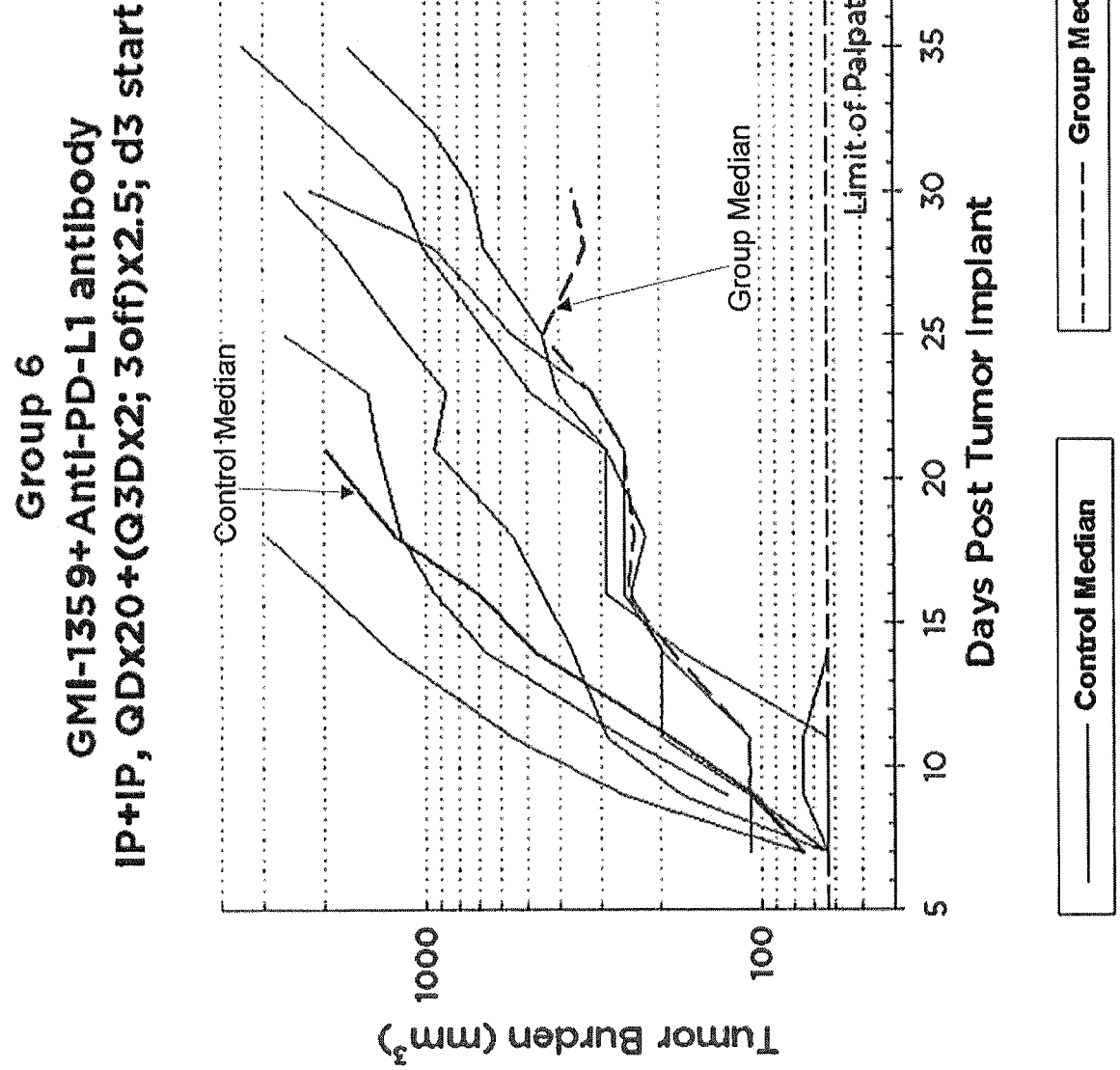
Figure 4C:
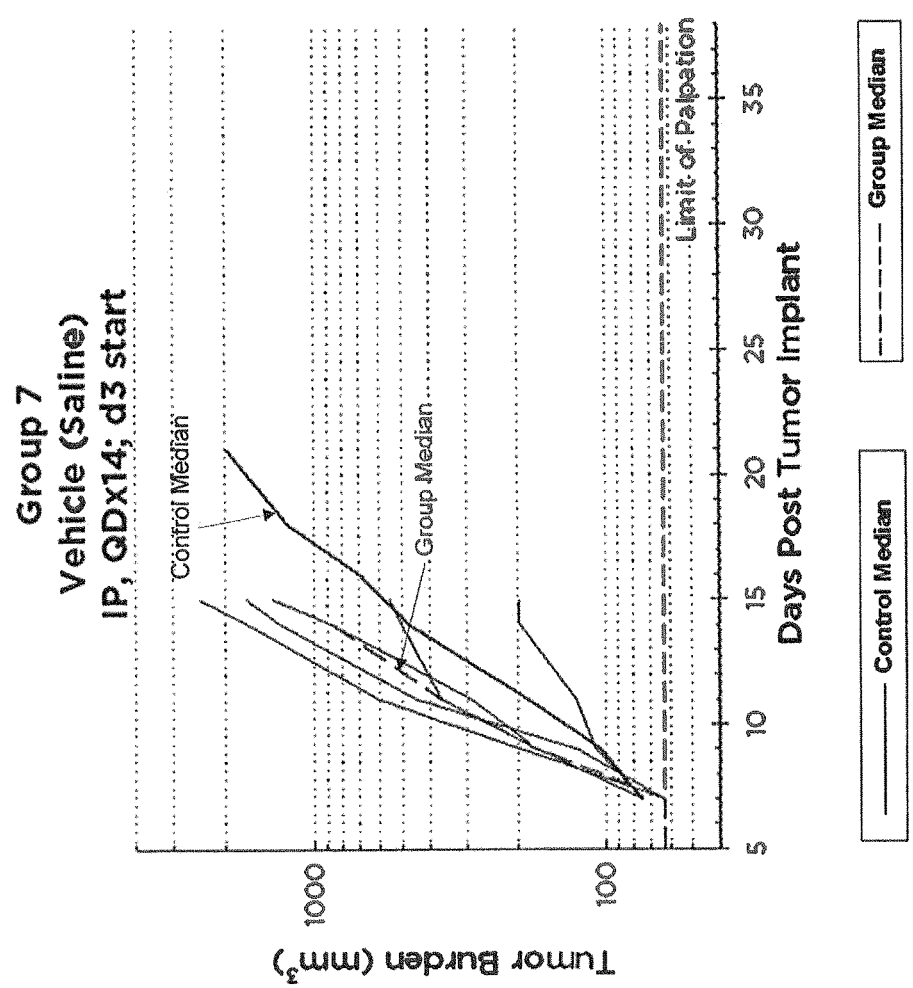
Figure 4D:
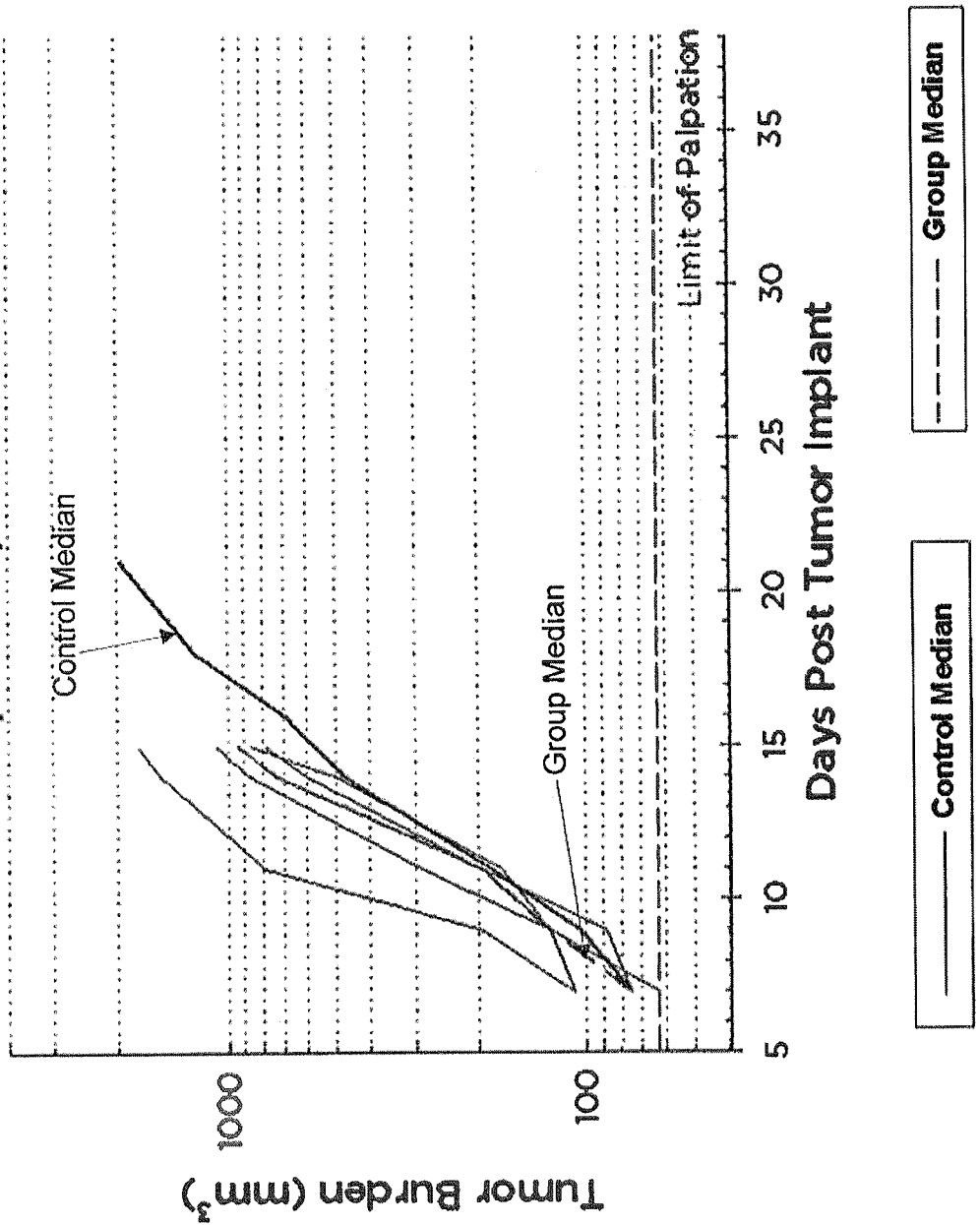
Figure 5A:
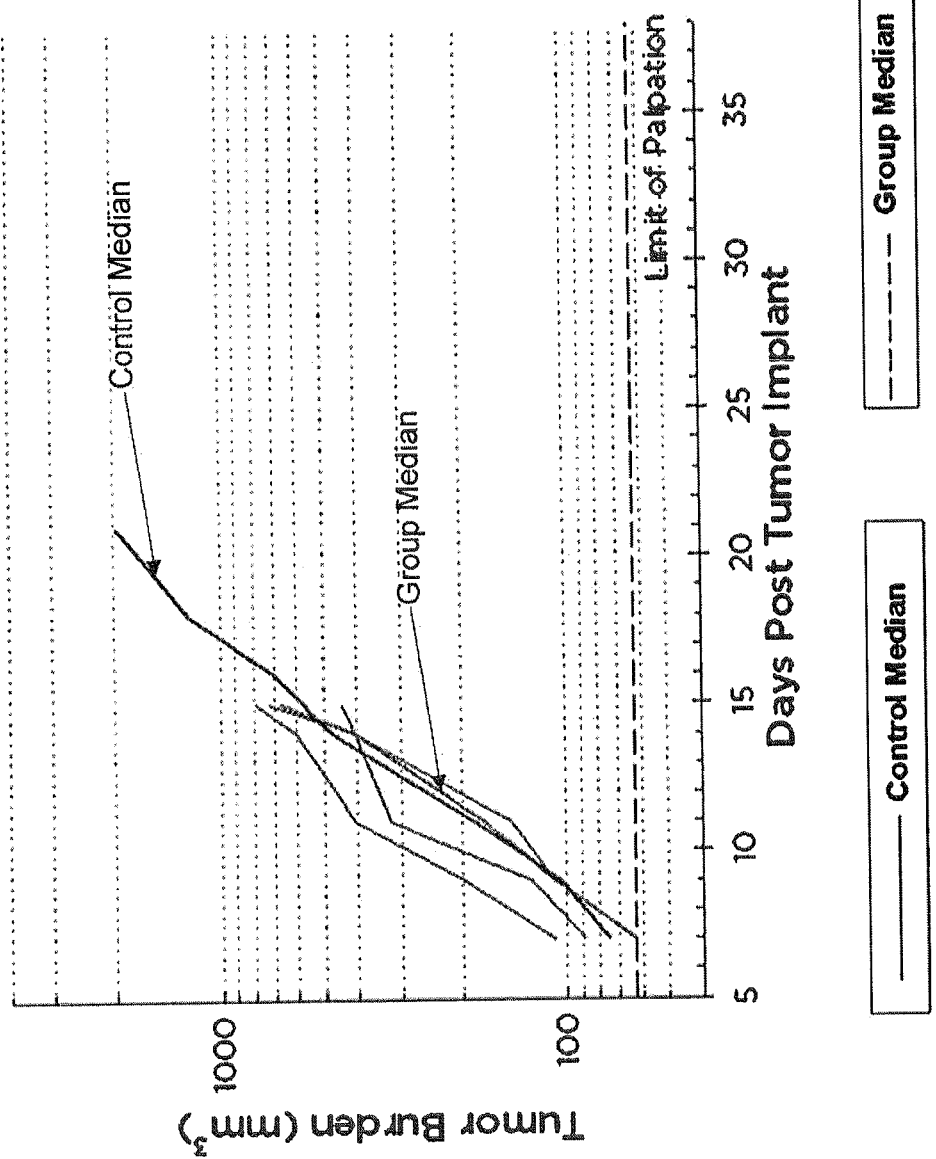
Figure 5B:
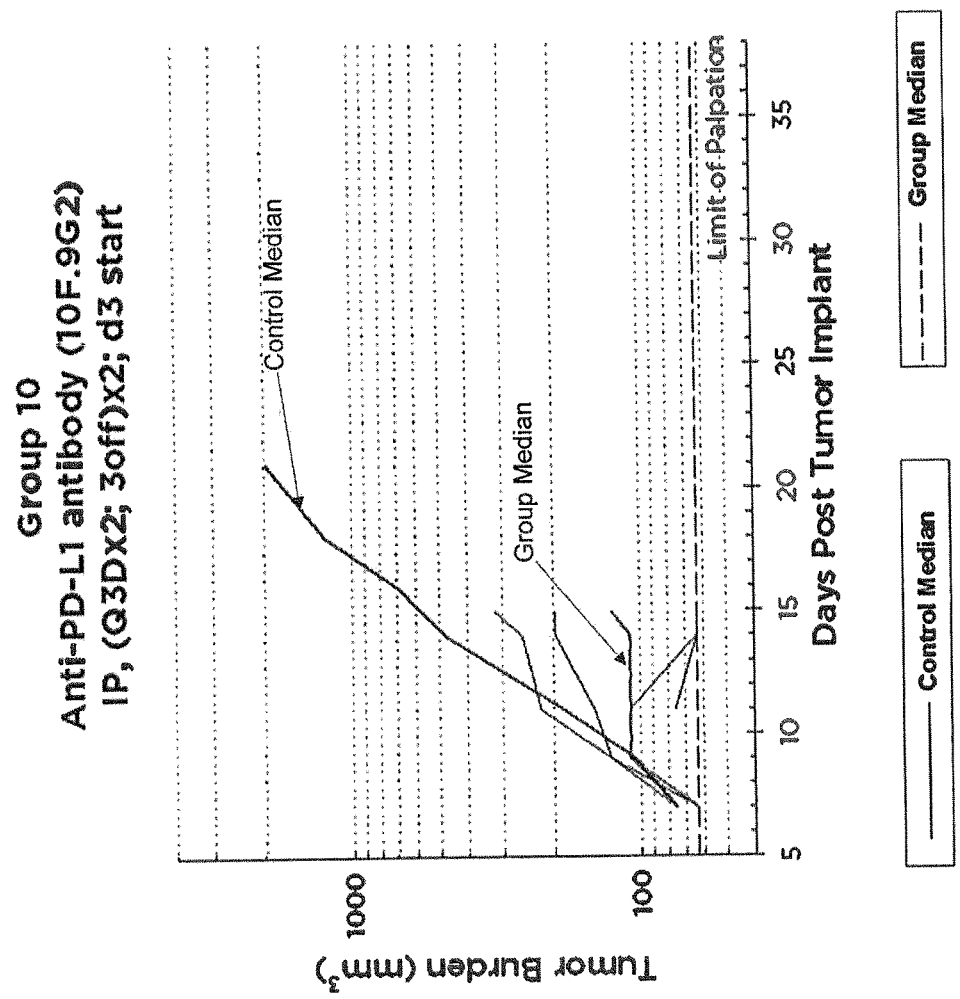
Figure 5C:
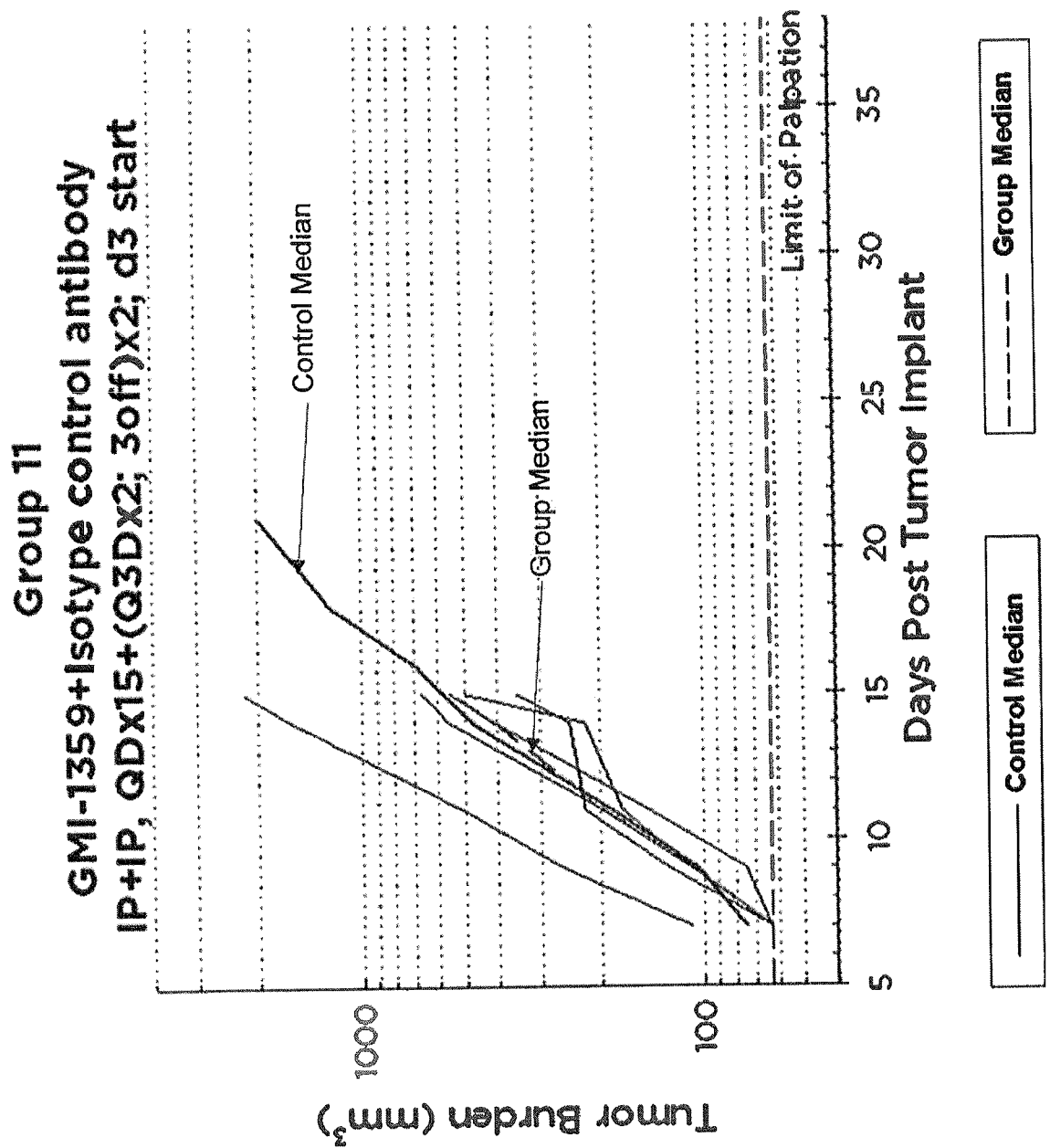
Figure 5D:
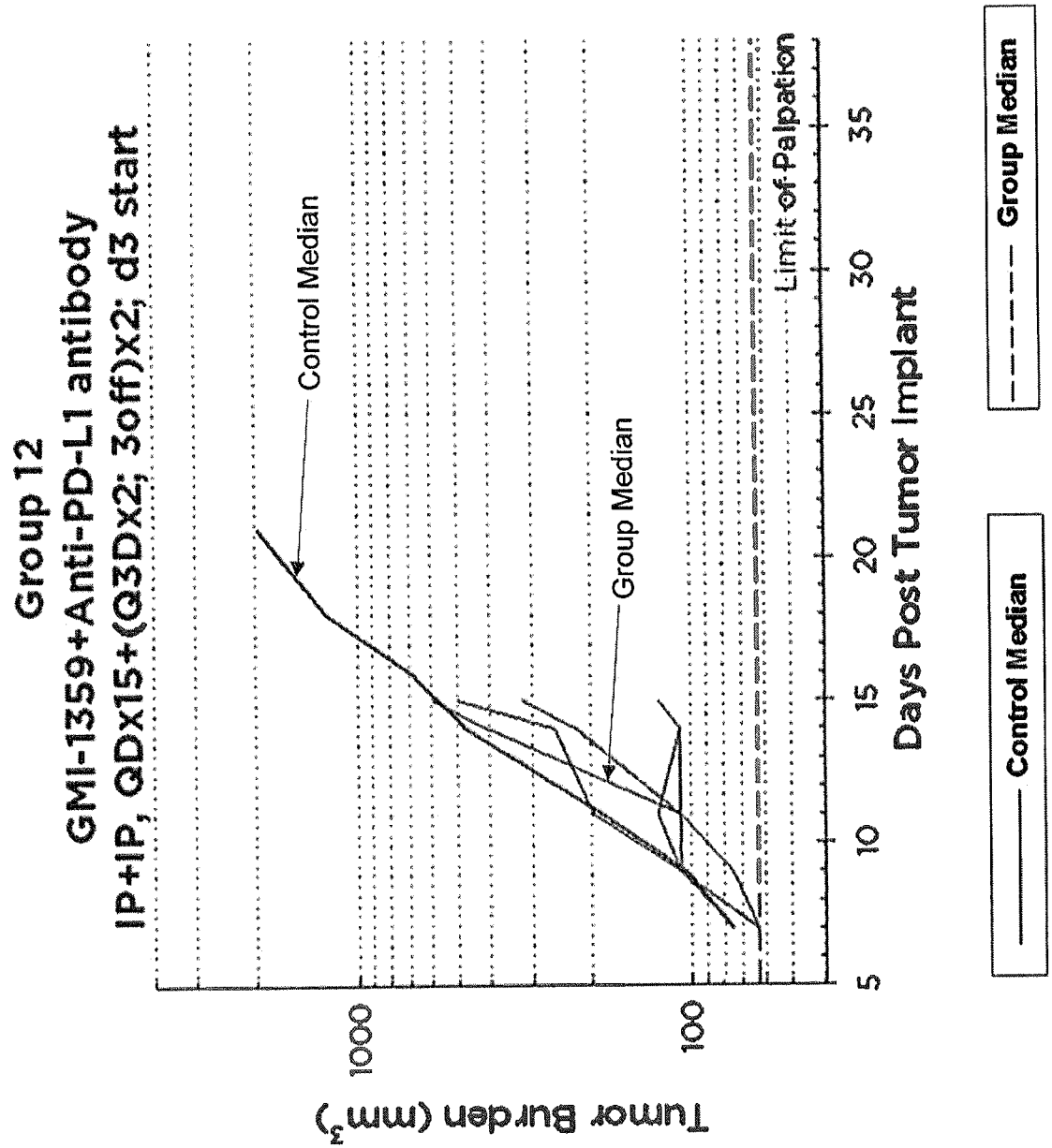

(GMI-1359 treatment, FIG. 4D), shown as tumor burden in mm³ and including control median and group median.

FIGS. 5A-D are graphs of the tumor growth of individual mice of group 9 (LTF-2 antibody, FIG. 5A); group 10 (anti-PD-L1 antibody treatment, FIG. 5B); group 11 (GMI-1359 and LTF-2 antibody, FIG. 5C); and group 12 (GMI-1359 and anti-PD-L1 antibody treatment, FIG. 5D), shown as tumor burden in mm³ and including control median and group median.

Figure 6:
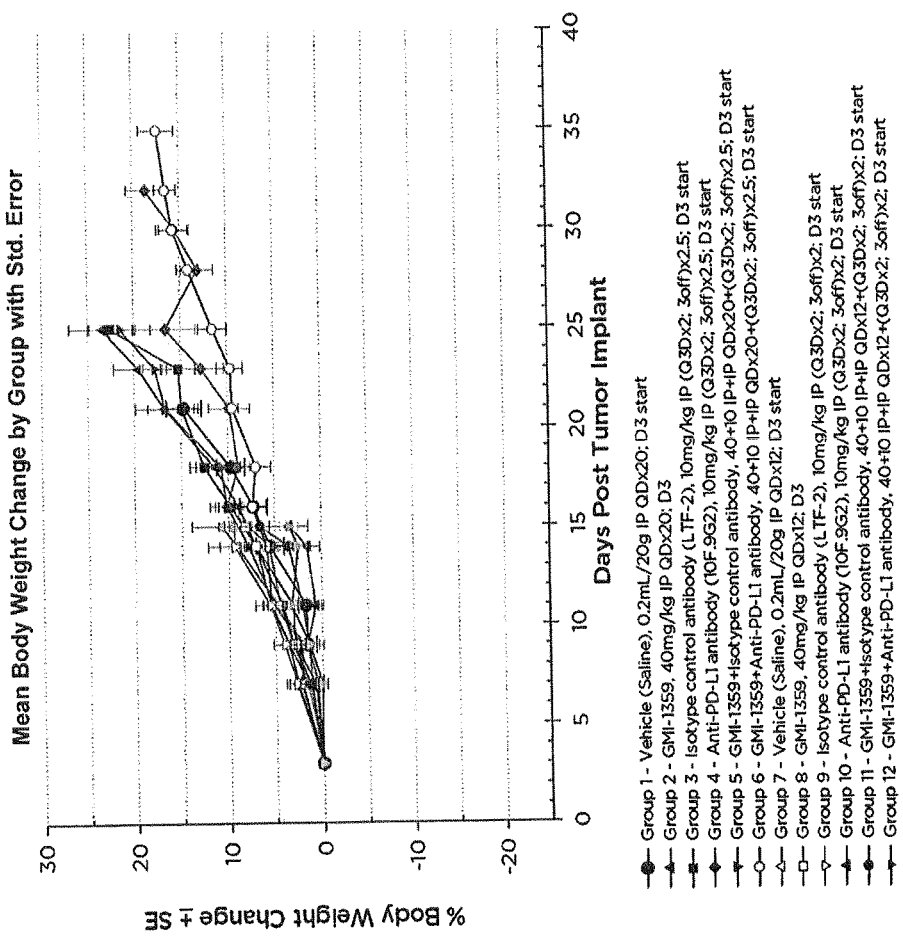

FIG. 6 is a graph of the percent mean body weight change for 12 experimental groups (control groups included as well), with standard error.

Figure 7:
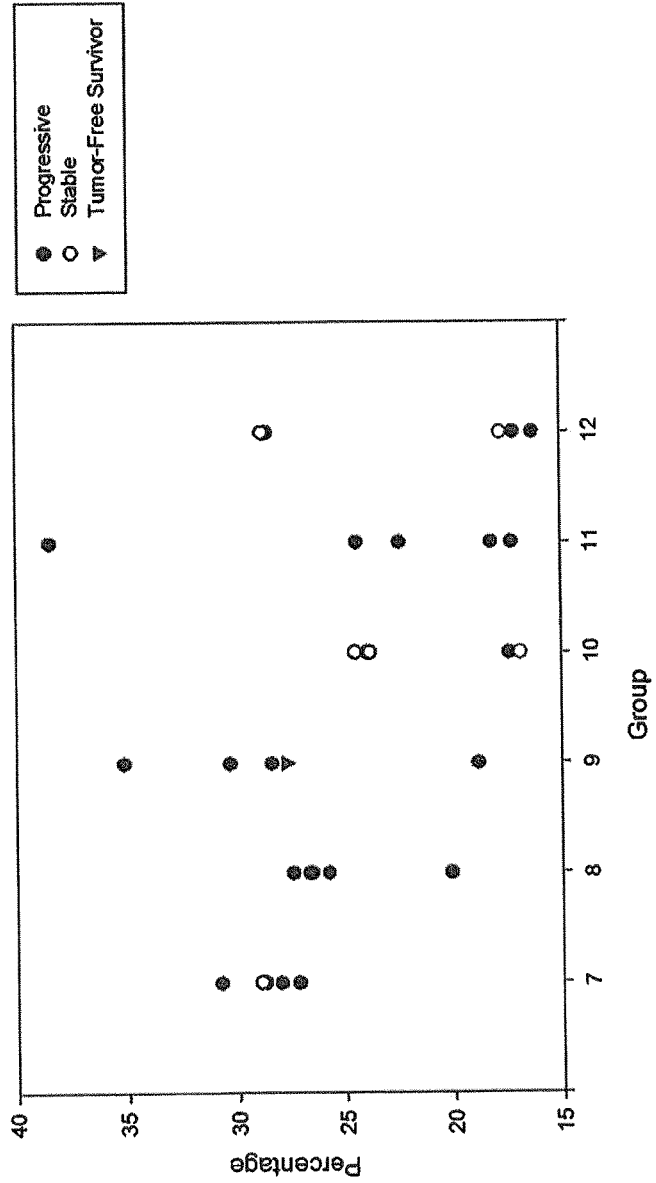

FIG. 7 is a graph of the percentage of $CD4^+/CCR7^+/CD62L^+$ cells in tumors for the individuals in experimental groups 7 through 12.

Figure 8:
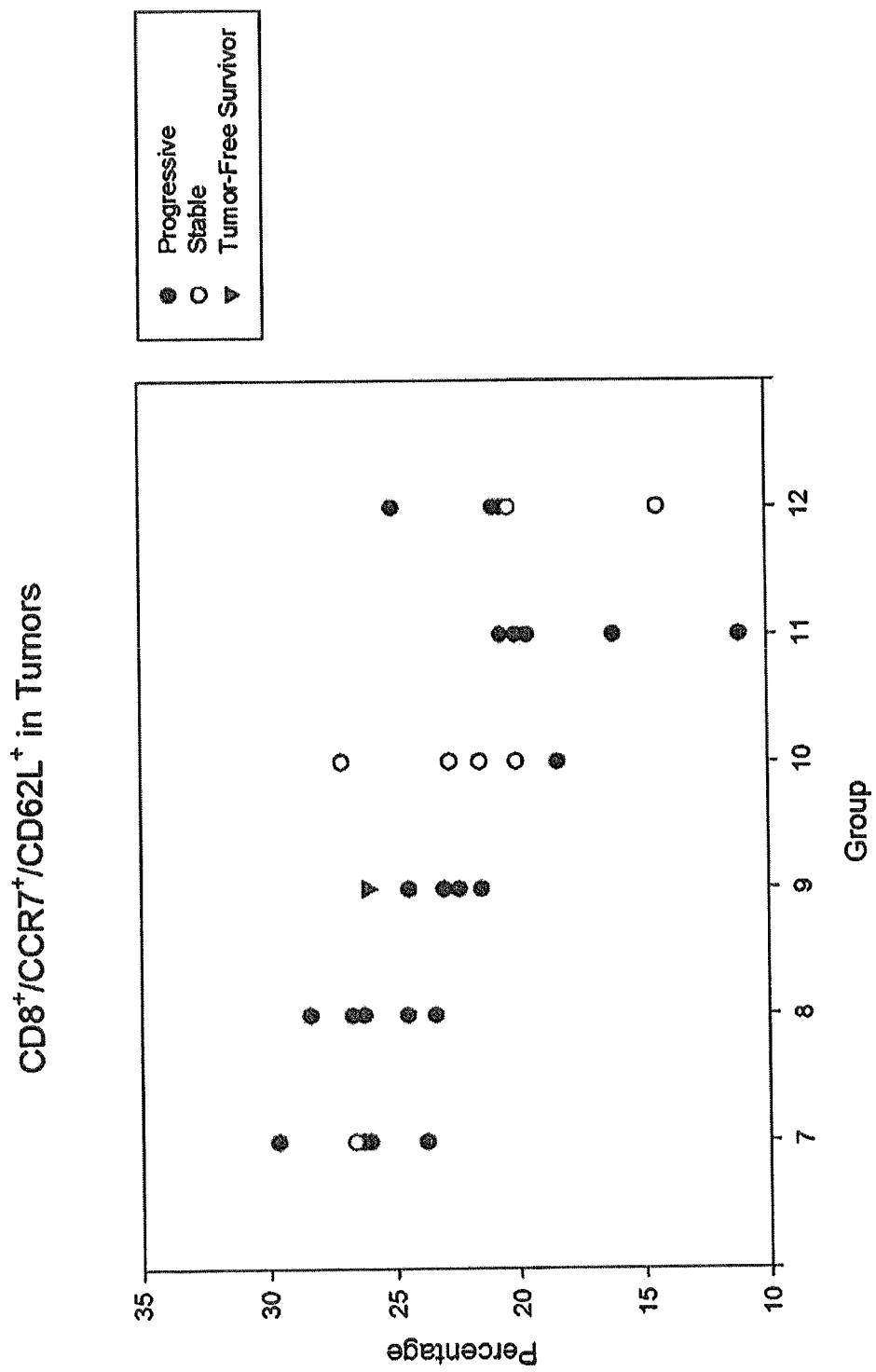

FIG. 8 is a graph of the percentage of $CD8^+/CCR7^+/CD62L^+$ cells in tumors for the individuals in experimental groups 7 through 12.

Figure 9:
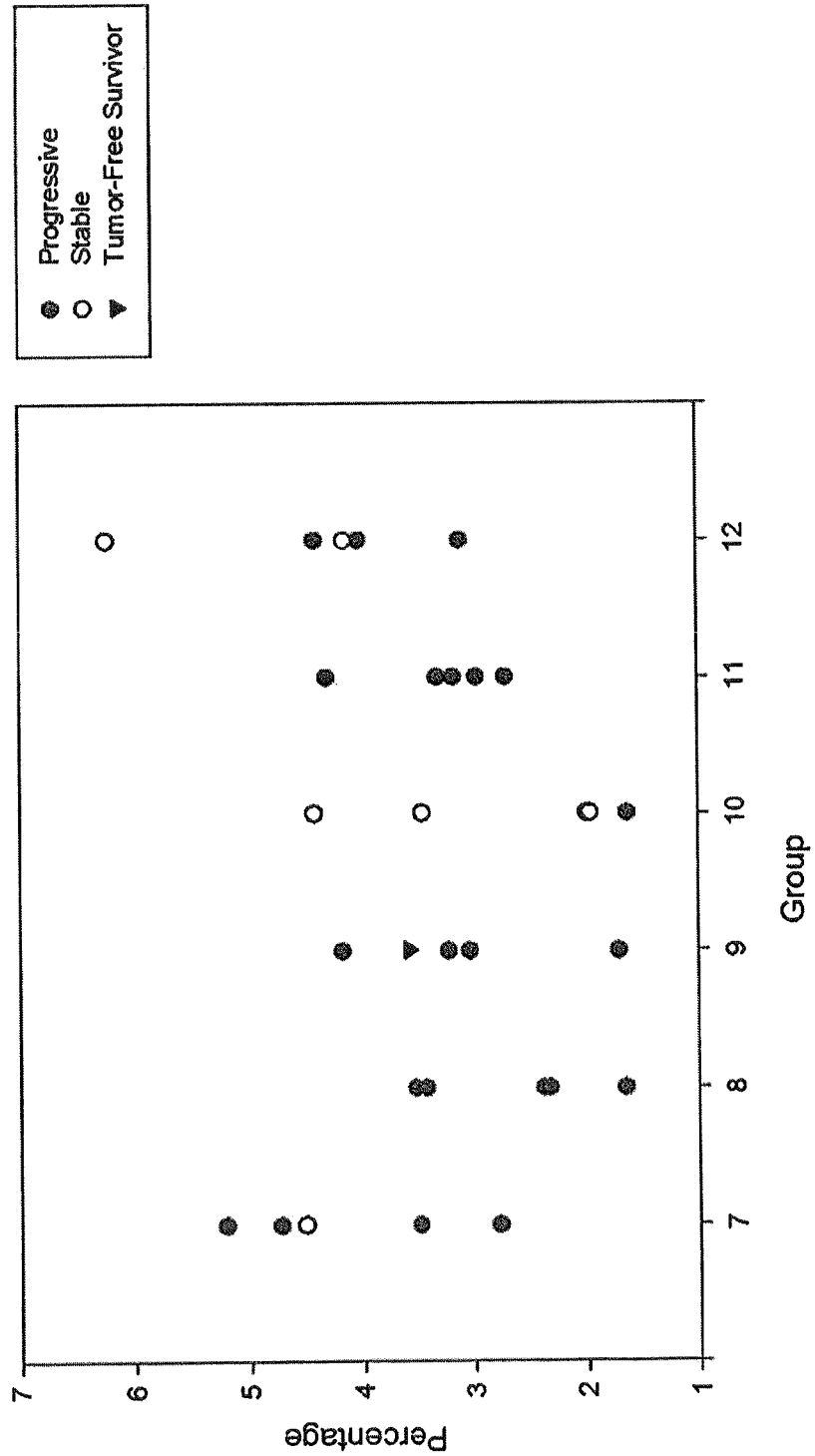

FIG. 9 is a graph of the percentage of $CD11b^+/GR1^+$ cells in tumors for the individuals in experimental groups 7 through 12.

Figure 10:
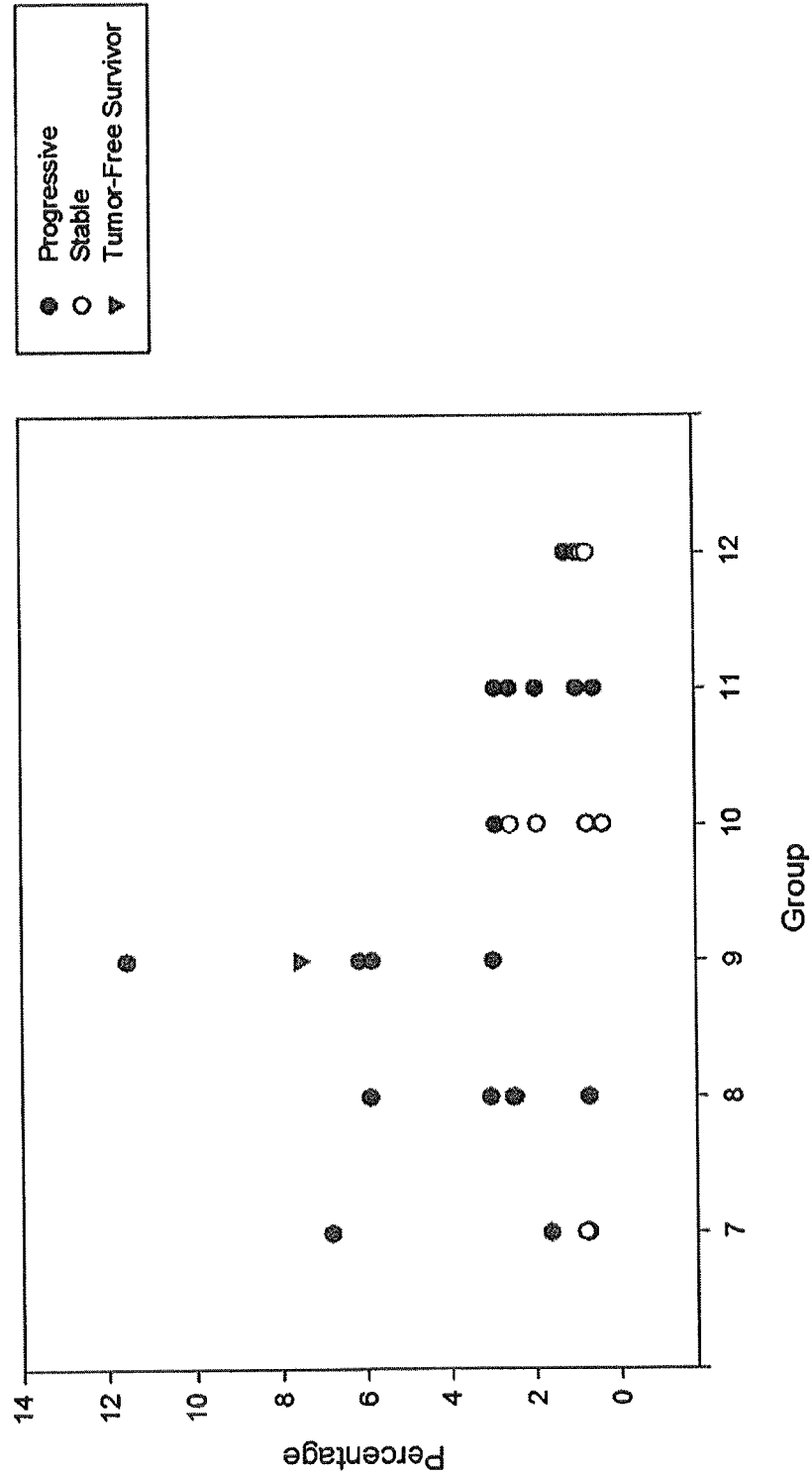

FIG. 10 is a graph of the percentage of $CD4^+/CD25^+/FoxP3^+$ cells ($T_{reg}$ cells) in tumors for the individuals in experimental groups 7 through 12.

Figure 11:
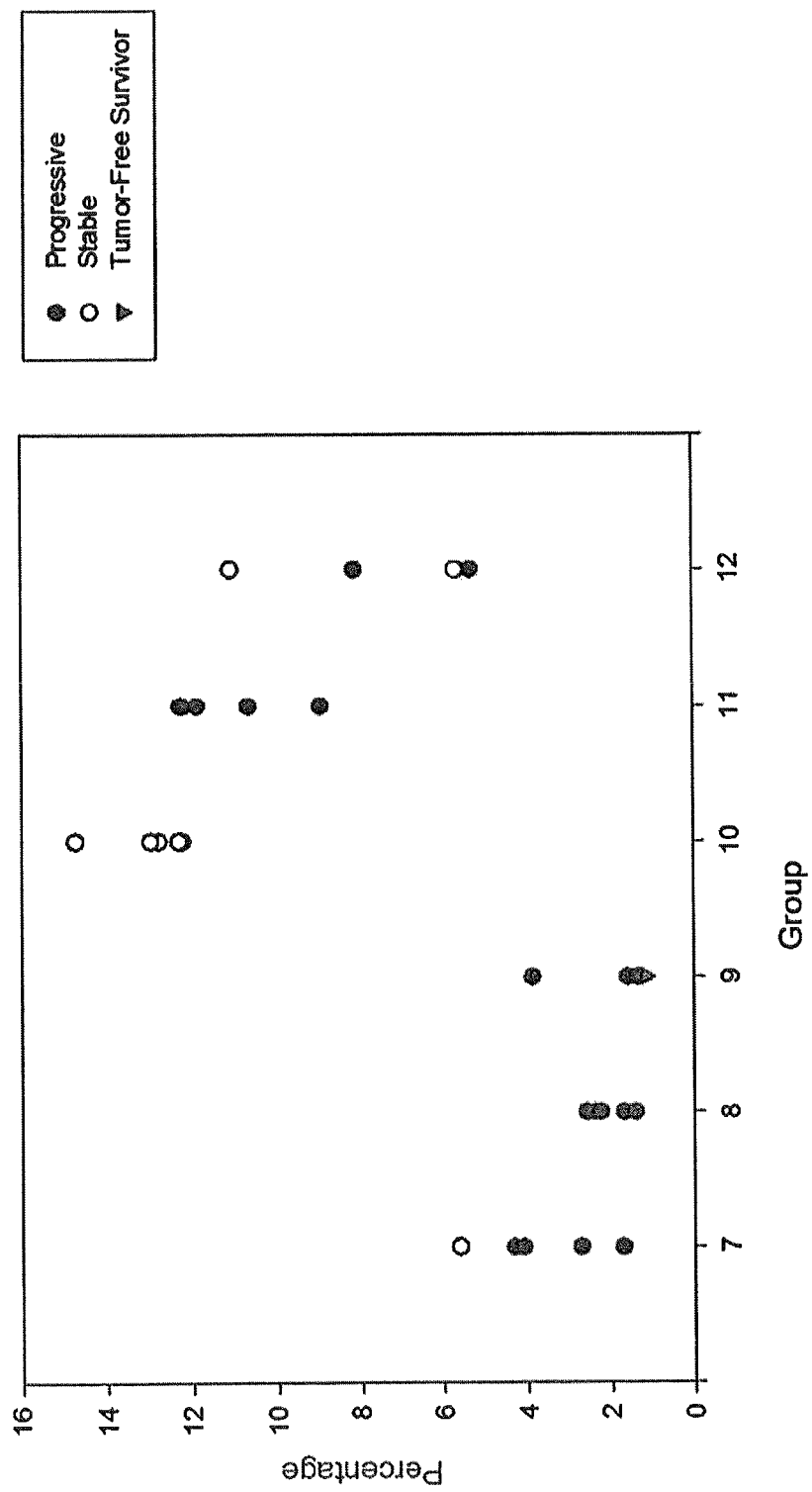

FIG. 11 is a graph of the percentage of $CD4^+/CCR7^+/CD62L^+$ cells in spleens for the individuals in experimental groups 7 through 12.

Figure 12:
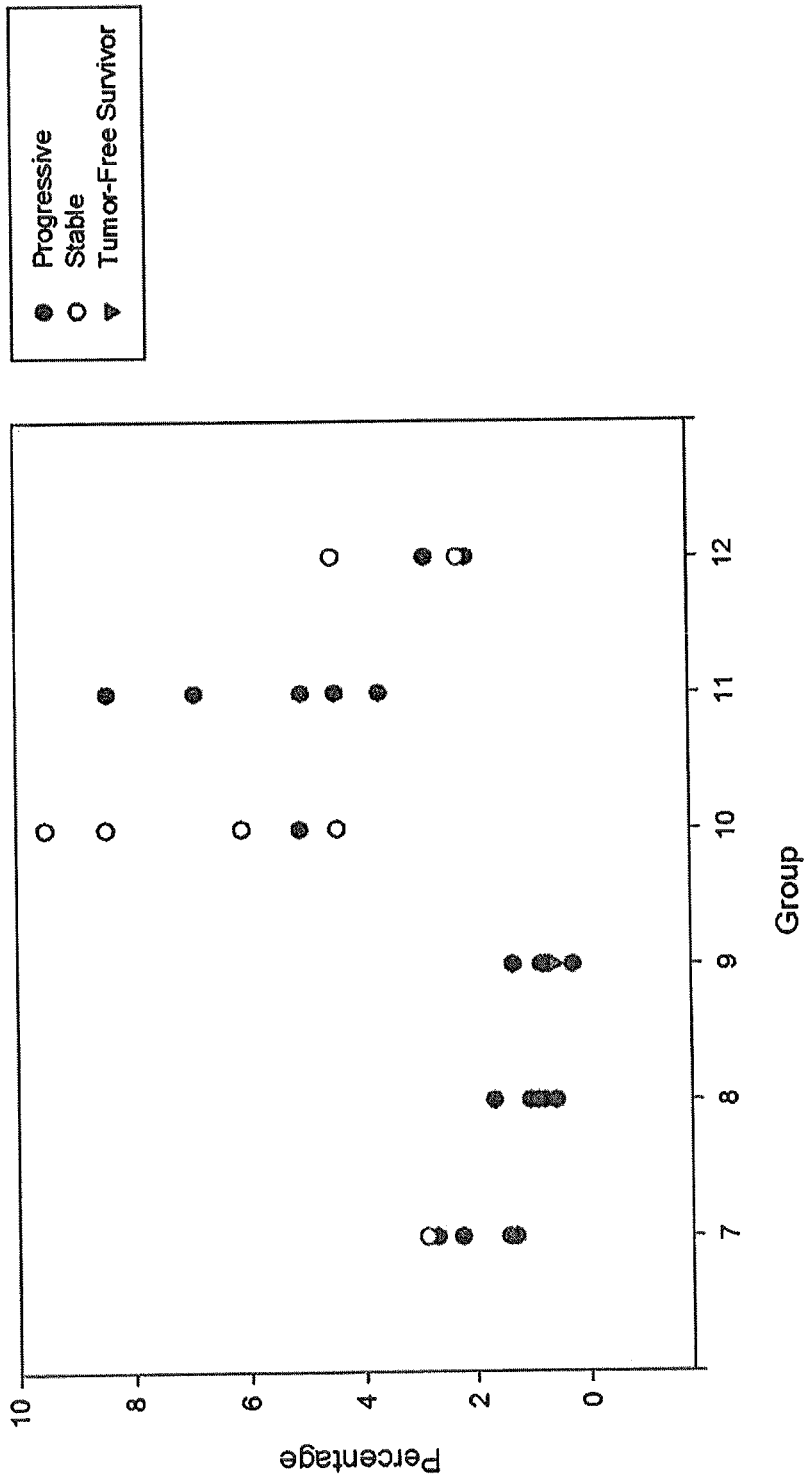

FIG. 12 is a graph of the percentage of $CD8^+/CCR7^+/CD62L^+$ cells in spleens for the individuals in experimental groups 7 through 12.

Figure 13:
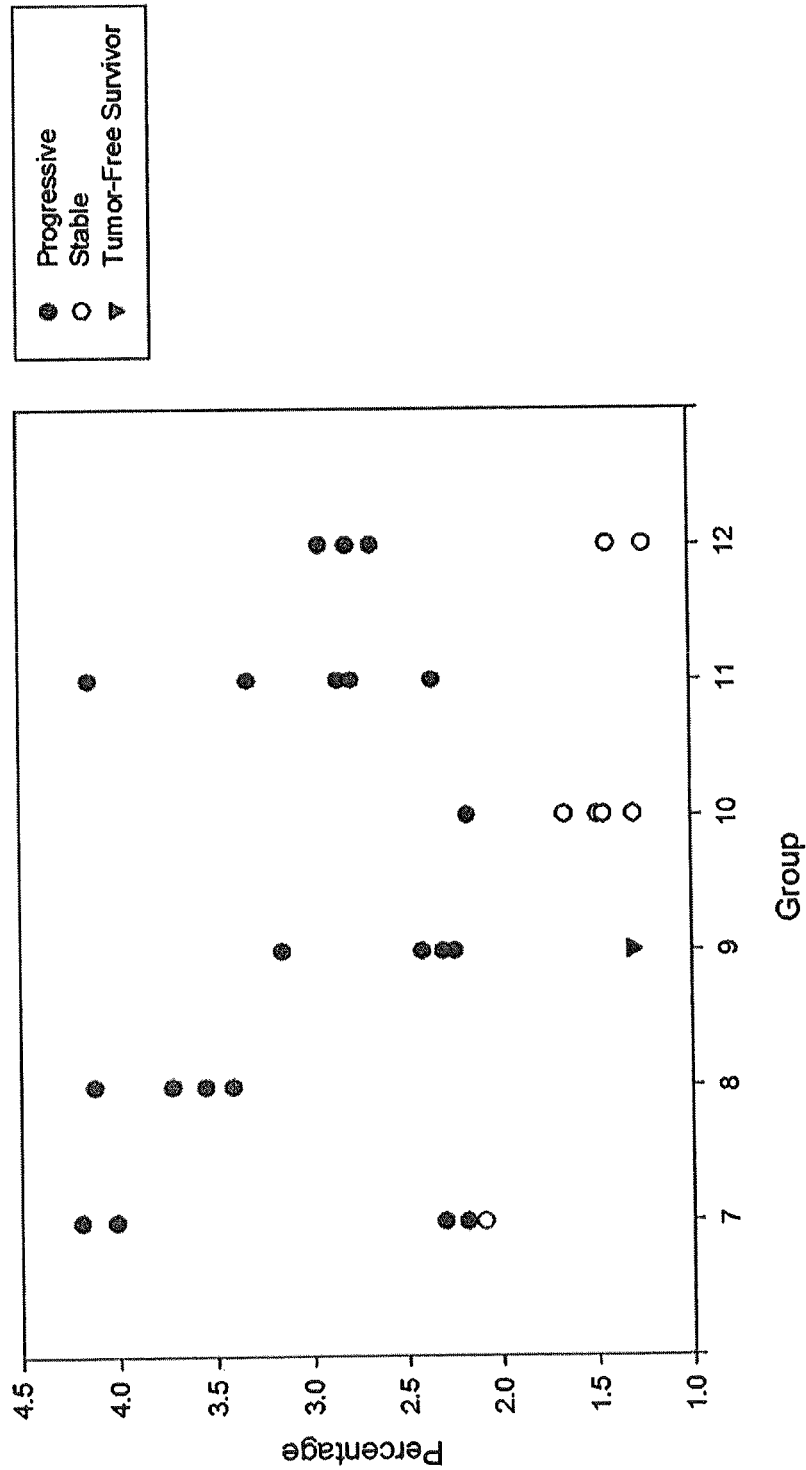

FIG. 13 is a graph of the percentage of $CD11b^+/GR1^+$ cells in spleens for the individuals in experimental groups 7 through 12.

Figure 14:
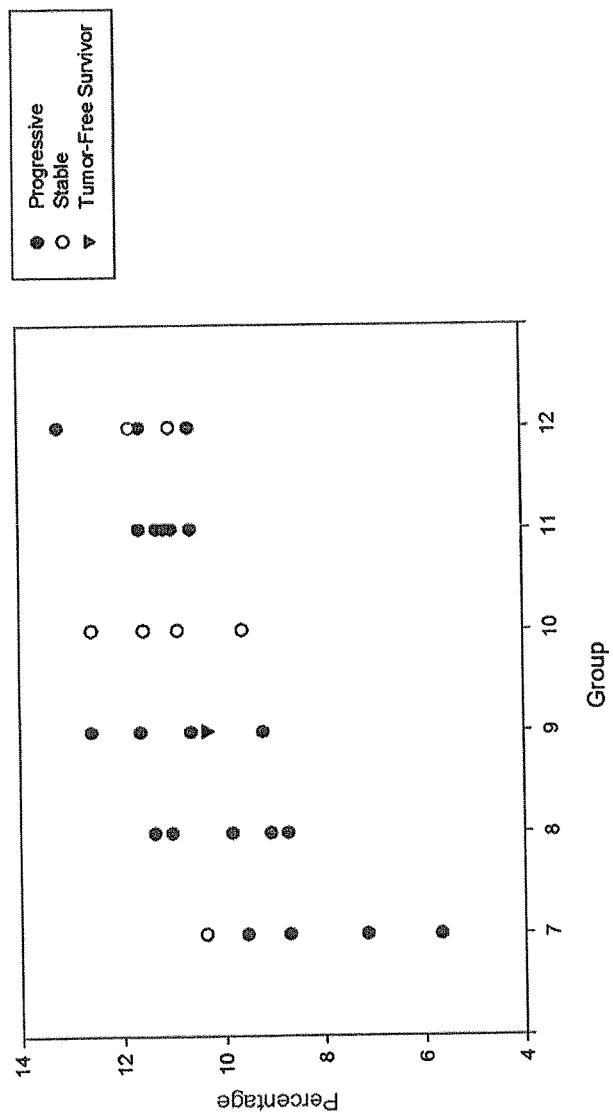

FIG. 14 is a graph of the percentage of $CD4^+/CD25^+/FoxP3^+$ cells ($T_{reg}$ cells) in spleens for the individuals in experimental groups 7 through 12.

Figure 15A:
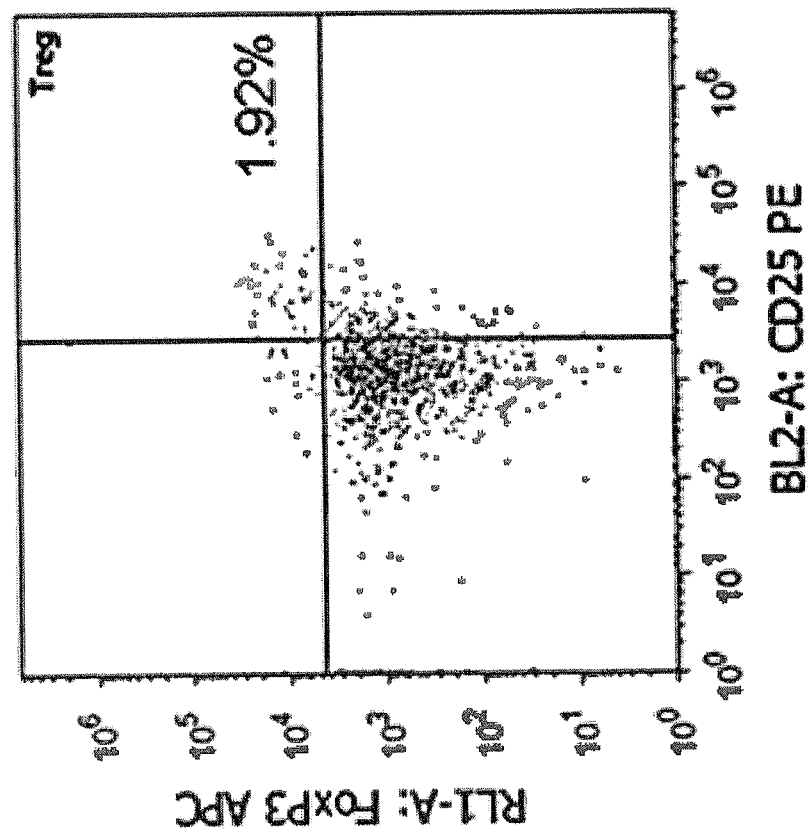
Figure 15B:
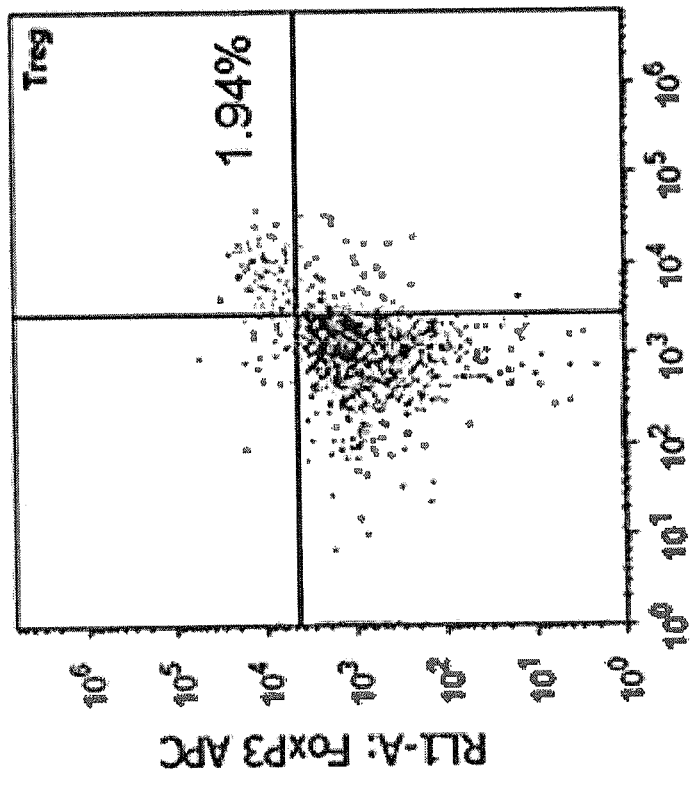
Figure 15C:
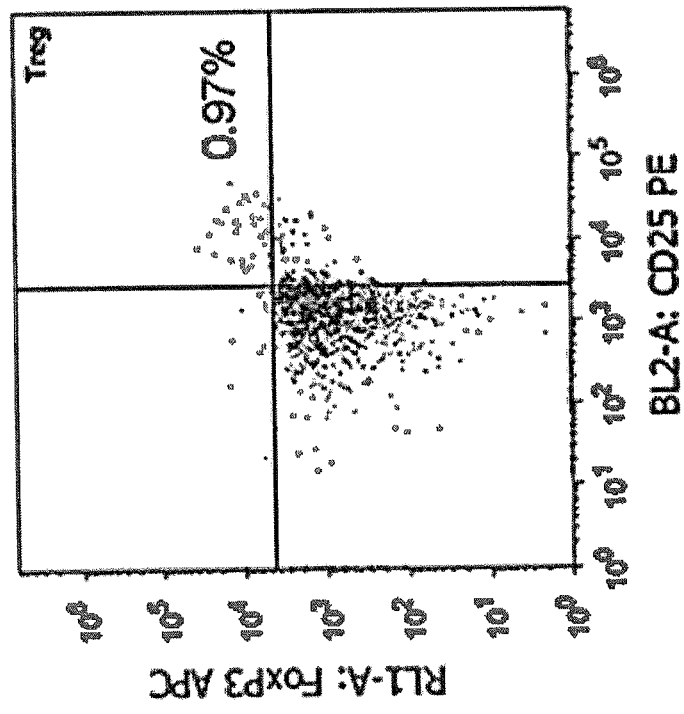

FIGS. 15A-C are representative scatter plots showing the $T_{reg}$ cells in tumors of an individual (mouse 5, group 10) treated with anti-PD-L1 antibody treatment (FIG. 15A); an individual (mouse 5, group 11) treated with GMI-1359 and LTF-2 antibody (FIG. 15B); and an individual (mouse 5, group 12) treated with GMI-1359 and anti-PD-L1 antibody treatment (FIG. 15C).

Figure 16A:
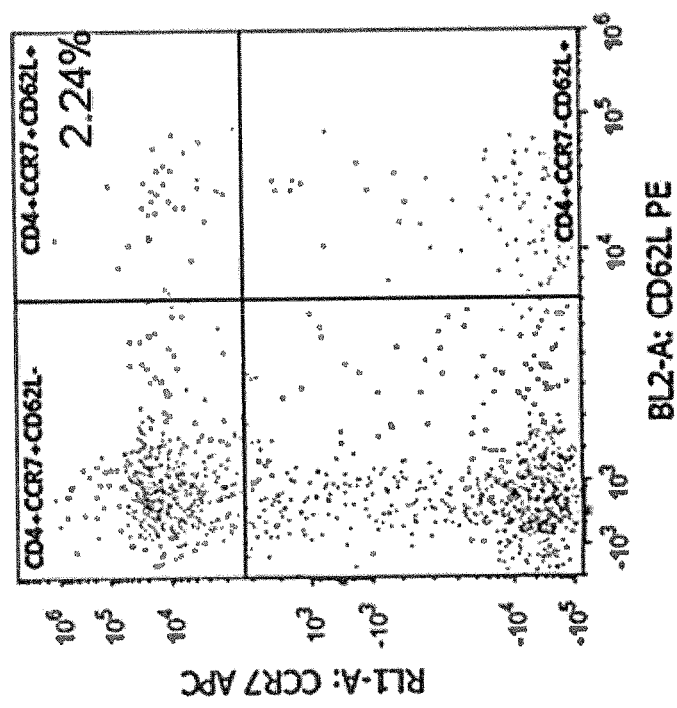
Figure 16B:
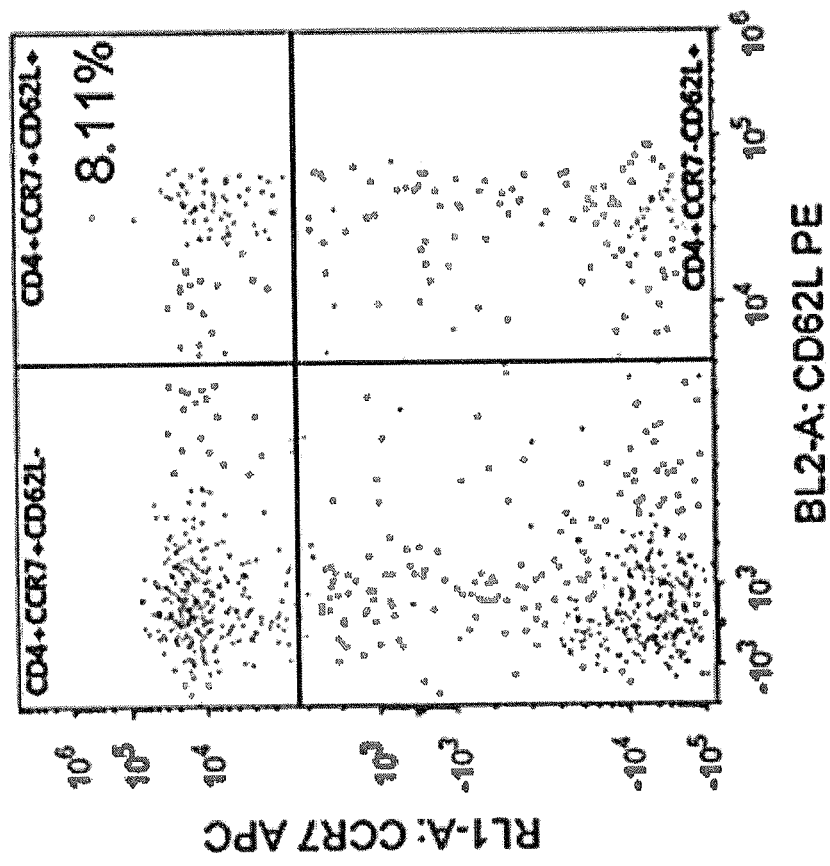

FIGS. 16A-B are representative scatter plots showing the $CD4^+/CCR7^+/CD62L^+$ cells in spleens of an individual (mouse 4, group 8) treated with GMI-1359 (FIG. 16A); and an individual (mouse 1, group 12) treated with GMI-1359 and anti-PD-L1 antibody treatment (FIG. 16B).

Figure 17A:
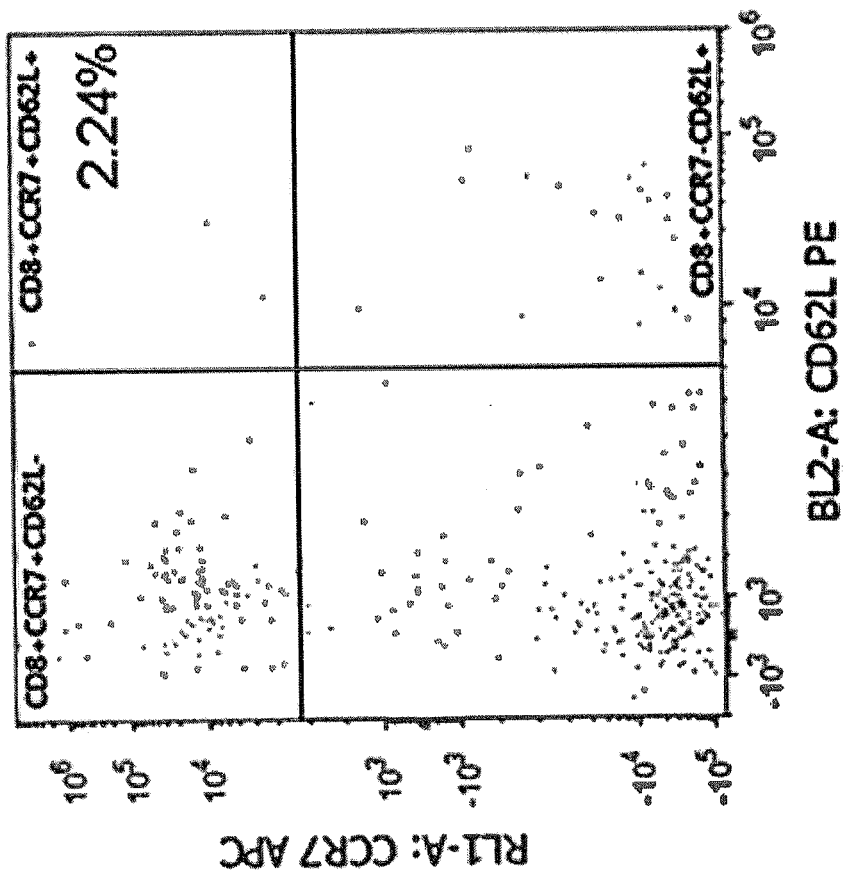
Figure 17B:
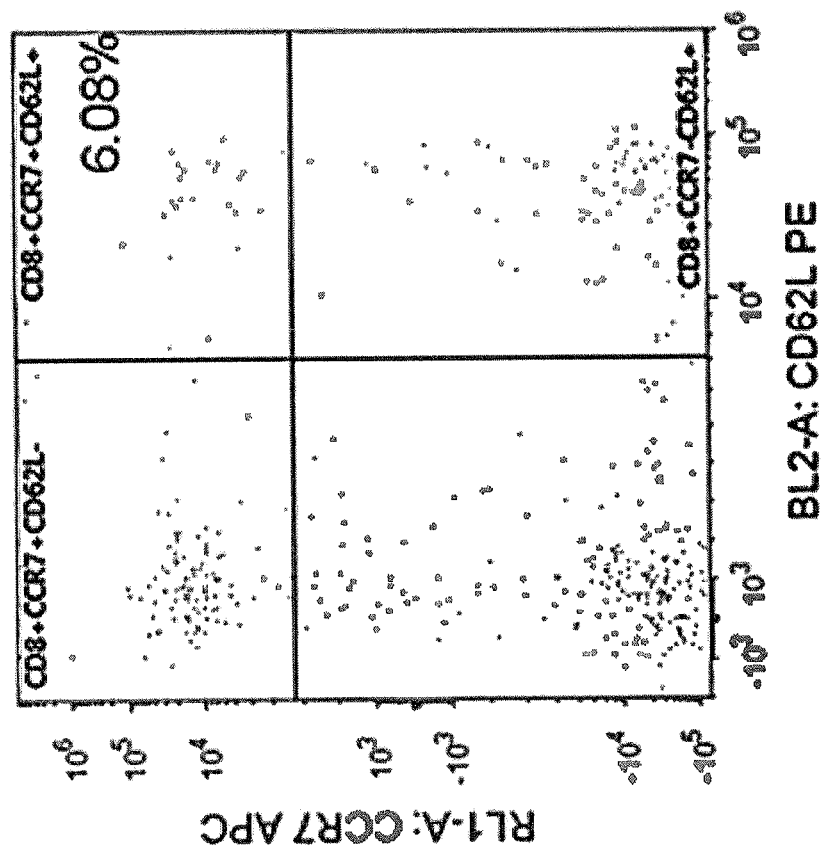

FIGS. 17A-B are representative scatter plots showing the $CD8^+/CCR7^+/CD62L^+$ cells in spleens of an individual (mouse 4, group 7) treated with saline (FIG. 17A); and an individual (mouse 3, group 10) anti-PD-L1 antibody treatment (FIG. 17B).

Figure 18A:
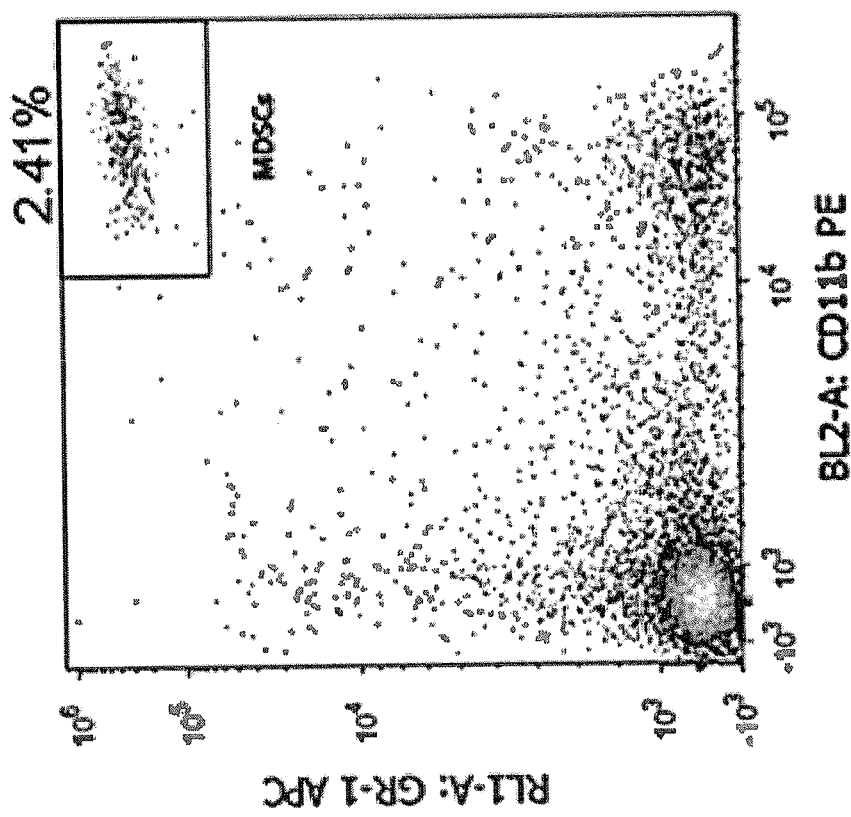
Figure 18B:
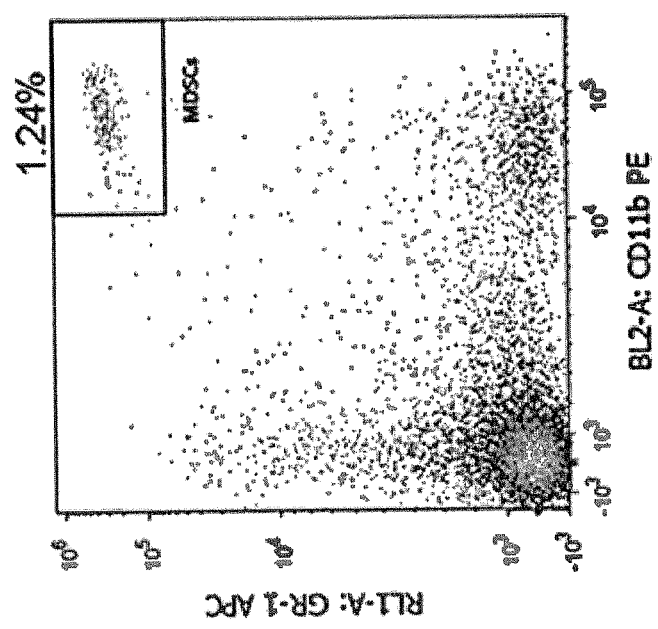
Figure 18C:
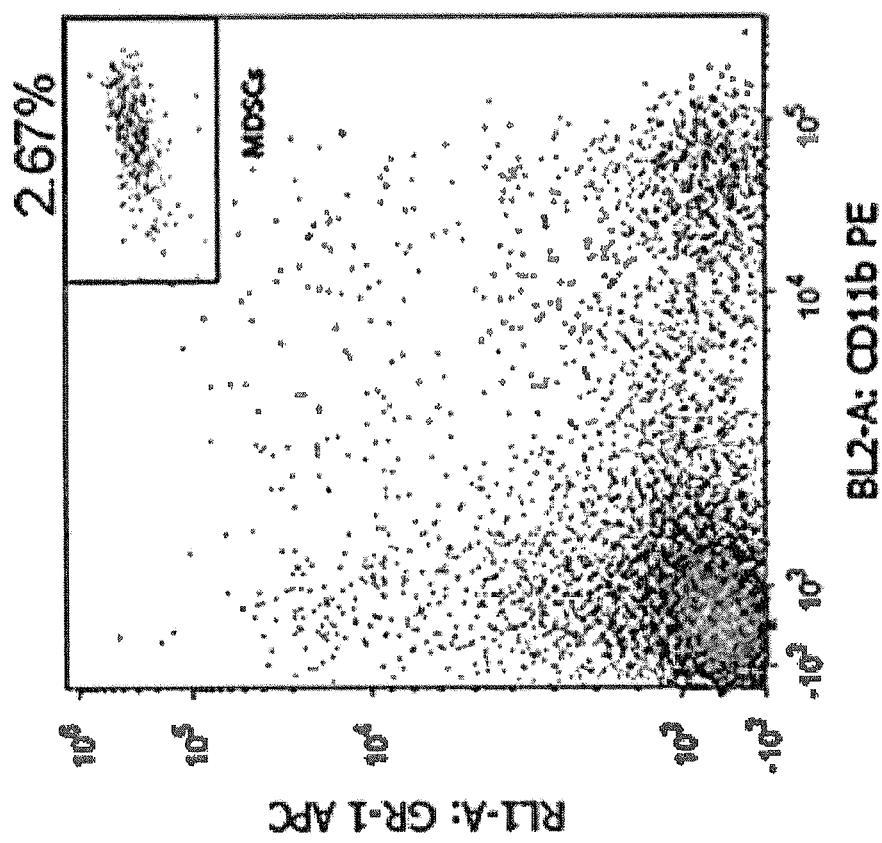

FIGS. 18A-C are representative scatter plots showing the $CD11b^+/GR1^+$ cells in tumors of an individual (mouse 3, group 9) treated with LTF-2 antibody treatment (FIG. 18A); an individual (mouse 3, group 12) treated with GMI-1359 and anti-PD-L1 antibody (FIG. 18B) and presenting with a stable disease state; and an individual (mouse 4, group 12) treated with GMI-1359 and anti-PD-L1 antibody treatment (FIG. 15C) and presenting with a progressive disease state.

FIG. 19 is a table of the toxicity and efficacy data for the 12 treatment groups.

FIG. 20 is a comparison of the complete response (CR) rate and the median days post treatment until to complete response for group 7 (anti-PD-L1 antibody treatment alone) and group 12 (GMI-1359 and anti-PD-L1 antibody treatment combined).

FIG. 21 is a table showing the competitive binding activity (IC50) of GMI-1359 against E-selectin and CXCR4.

Figure 22:
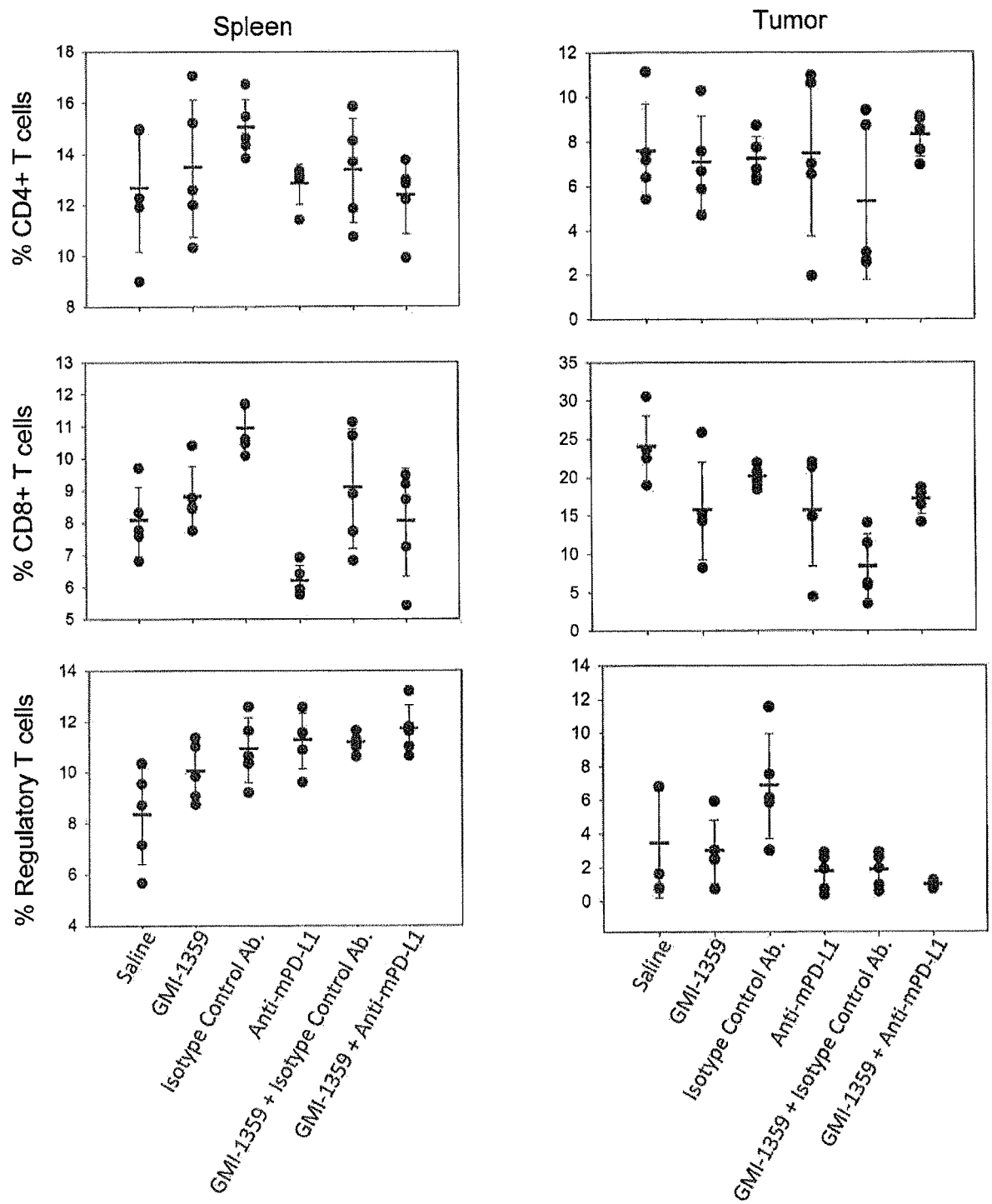

FIG. 22 displays graphs of the percentages of CD4+, CD8+ and Regulatory T cells in spleen and tumor tissue samples, in vivo, on study day 15, in each treatment group.

FIG. 23 is a table that shows the ratio of CD8/regulatory T cells in spleen and tumor tissue samples, in vivo, on study day 5, in each treatment group.

FIG. 24A shows a mean tumor burden group comparison and response summary table.

Figure 24B:
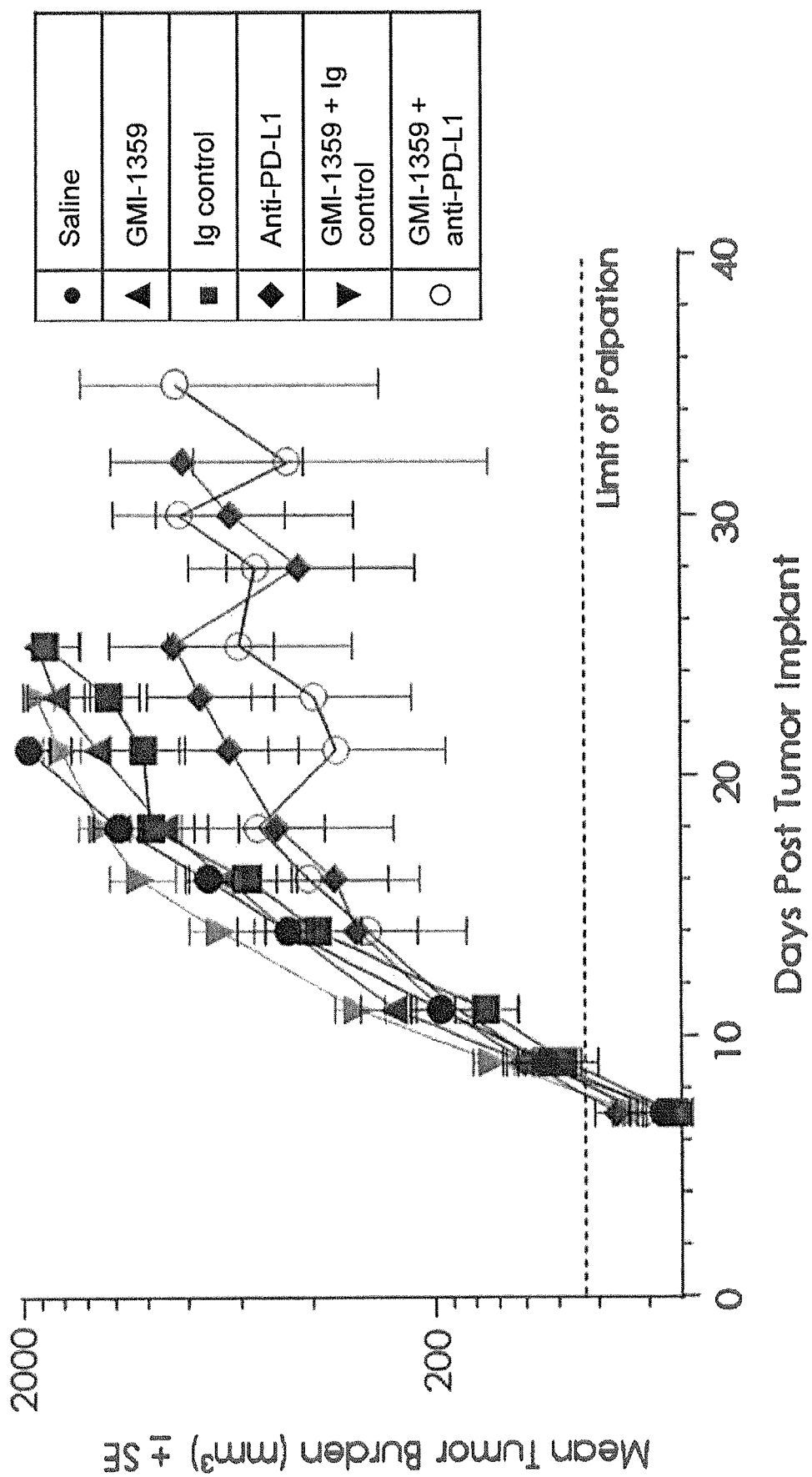

FIG. 24B is a graph that shows the number of days post tumor implant on the x-axis, and the mean tumor burden (mm³) in each treatment group, on the y-axis.

The terms defined below are more fully defined by reference to the specification as a whole. While the terms used herein are believed to be well understood by one of ordinary skill in the art, the definitions included in this document are set forth to facilitate explanation of the presently-disclosed subject matter.

Following long-standing patent law convention, the terms "a," "an," and "the" refer to "one or more" when used in this application, including the claims. Thus, for example, reference to "a cell" includes one cell or a plurality of cells, and so forth.

Throughout this disclosure, various embodiments can be presented in a range format. Numeric ranges are inclusive of the numbers defining the range. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range, such as from 1 to 6, should be considered to have specifically disclosed subranges, such as from 1 to 3, from 1 to 4, from 1 to 5, from 2 to 4, from 2 to 6, from 3 to 6 etc., as well as individual numbers within that range, for example, 1, 2, 2.7, 3.8, 4, 5.1, 5.3, and 6. This applies regardless of the breadth of the range.

E-selectin (CD62E) is a cell adhesion molecule that is expressed on activated endothelial cells and plays an important role in leukocyte recruitment to the site of injury. The terms "E-selectin inhibitor" or "E-selectin antagonist" and the like are used interchangeably and mean an agent that inhibits an activity of E-selectin or inhibits the binding of E-selectin to one or more E-selectin ligands (which in turn may inhibit a biological activity of E-selectin). The term "E-selectin inhibitor" includes inhibitors of E-selectin only, as well as inhibitors of E-selectin and either P-selectin or L-selectin, and inhibitors of E-selectin, P-selectin, and L-selectin.

The term "non-glycomimetic moiety" includes moieties having a structure not intended to mimic a carbohydrate molecule. A non-glycomimetic moiety may not be (and is typically not) active as an E selectin antagonist. Instead, non-glycomimetic moieties are generally moieties added to a glycomimetic moiety for purposes of altering at least one property, such as solubility, bio-availability, lipophilicity and/or other drug-like properties of the glycomimetic.

"$T_{reg}$ cells" are a subpopulation of T cells which modulate the immune system, maintain tolerance to self-antigens, and prevent autoimmune disease. $T_{reg}$ cells are immunosuppressive and generally suppress or downregulate induction and proliferation of other T cells. $T_{regs}$ cells express the biomarkers CD4, CD25, and FoxP3 (i.e., are CD4$^+$/CD25$^+$/FoxP3$^+$).

T-cell checkpoints are molecules that need to be activated or inactivated to start an immune response. "T-cell checkpoint inhibitors," "checkpoint inhibitors" or "immunoregulatory receptor blocks" are agents that prevent or inhibit the normal T-cell checkpoint operation and prevent an immune response. For example, PD-1 (cell death protein 1) is a checkpoint protein on T cells that is important in self-recognition. PD-1 usually prevents the T cells from attacking normal body cells because normal body cells present the PD-L1 (the ligand that binds to PD-1). When the PD-1 checkpoint protein attaches to the PD-L1 protein of a cell, the T cell does not attack that cell. As noted above, PD-L1 is present on normal cells, but some cancer cells have large amounts of PD-L1, which helps them evade immune attack. A T-cell checkpoint inhibitor may block the PD-L1 protein presented on the cancer cells (or it may block the PD-1 of the T-cells) to prevent the T-cell's PD-1 from binding to the PD-L1. If the PD-1 and PD-L1 binding is blocked, the T-cell does not recognize the cell as "self," and may attack the cell. Accordingly, a T-cell checkpoint inhibitor may assist the immune system in attacking cancer cells that present PD-L1 proteins. Examples of T-cell checkpoint inhibitors are known in the art, including anti-PD-1 antibodies, anti-PD-L1 antibodies, and anti-CTLA4 antibodies.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "therapy" refers to "treating" or "treatment" of a disease or condition including inhibiting the disease (slowing or arresting its development), providing relief from the symptoms or side-effects of the disease (including palliative treatment), and relieving the disease (causing regression of the disease). "Therapy" may also refer to prophylactic treatment, which includes preventing or delaying the onset of the disease or condition from occurring in a subject that may be predisposed to the disease but does not yet experience or exhibit symptoms of the disease.

As used herein, "together" is used to mean that the agents are administered concurrently. They can be administered in the same composition or in separate compositions. In contrast to "together," "sequentially" is used herein to mean that the gap between administering one agent and the other is significant, i.e., the first administered agent may no longer be present in the bloodstream in a therapeutic amount when the second agent and/or third agent is administered. When administered sequentially, the compounds may be administered in any order (e.g., a T-cell checkpoint inhibitor administered first followed by an E-selectin inhibitor or an E-selectin inhibitor administered first followed by an E-selectin inhibitor, etc.).

The term "treatment" means the slowing down, interruption, arrest, reversal or stoppage of the progression of the disease, which does not necessarily require the complete elimination of all the signs and symptoms of the disease. Furthermore, it is not necessary for the treatment to show effectiveness in 100% of the patients treated, rather, the term "treatment" is intended to mean that a statistically significant proportion of patients can be treated effectively, in such a way that the symptoms and clinical signs show at least an improvement. The person skilled in the art can easily establish whether the proportion is statistically significant using various statistical methods (e.g. confidence intervals, determination of them p value, Students t-test, Mann-Whitney test etc.). Confidence intervals have a confidence of at least 90%, at least 95%, at least 97%, at least 98% or at least 99%. The p values are 0.1, 0.05, 0.01, 0.005 or 0.0001.

In some embodiments, a method for treatment and/or prevention of at least one disease, disorder, or condition is disclosed, the method comprising administering to a subject in need thereof (1) an effective amount of at least one T-cell checkpoint inhibitor and (2) an effective amount of at least one other inhibitor chosen from E-selectin inhibitors, CXCR4 receptor inhibitors, and heterobifunctional inhibitors that comprise at least one E-selectin inhibitor linked to at least one CXCR4 receptor inhibitor.

In some embodiments, at least one of (1) the at least one T-cell checkpoint inhibitor and (2) the at least one other inhibitor is in the form of at least one pharmaceutical composition. In some embodiments, the at least one pharmaceutical composition further comprises at least one pharmaceutically acceptable ingredient. In some embodiments, the at least one T-cell checkpoint inhibitor is in the form of a first pharmaceutical composition and the at least one other inhibitor is in the form of a second pharmaceutical composition.

In some embodiments, a method for treatment and/or prevention of at least one bacterial infection, viral infection, or condition relating to at least one bacterial or viral infection is disclosed, the method comprising administering to a subject in need thereof (1) an effective amount of at least one T-cell checkpoint inhibitor and an effective amount of at least one other inhibitor chosen from E-selectin inhibitors, CXCR4 receptor inhibitors, and heterobifunctional inhibitors that comprise at least one E-selectin inhibitor linked to at least one CXCR4 receptor inhibitor, and/or (2) an effective amount of at least one pharmaceutical composition comprising at least one T-cell checkpoint inhibitor and at least one other inhibitor chosen from E-selectin inhibitors, CXCR4 receptor inhibitors, and heterobifunctional inhibitors that comprise at least one E-selectin inhibitor linked to at least one CXCR4 receptor inhibitor. In some embodiments, the infection is an HIV infection. In some embodiments, the condition relating to a bacterial or viral infection is sepsis or septic conditions.

In some embodiments, a method for treatment and/or prevention of at least one cancer is disclosed, the method comprising administering to a subject in need thereof (1) an effective amount of at least one T-cell checkpoint inhibitor and an effective amount of at least one other inhibitor chosen from E-selectin inhibitors, CXCR4 receptor inhibitors, and heterobifunctional inhibitors that comprise at least one E-selectin inhibitor linked to at least one CXCR4 receptor inhibitor, and/or (2) an effective amount of at least one pharmaceutical composition comprising at least one T-cell checkpoint inhibitor and at least one other inhibitor chosen from E-selectin inhibitors, CXCR4 receptor inhibitors, and heterobifunctional inhibitors that comprise at least one E-selectin inhibitor linked to at least one CXCR4 receptor inhibitor.

In some embodiments, a method for treatment and/or prevention of at least one disease, disorder, or condition in which suppression of $T_{reg}$ cells is desired, the method comprising administering to a subject in need thereof (1) an effective amount of at least one T-cell checkpoint inhibitor and an effective amount of at least one other inhibitor chosen from E-selectin inhibitors, CXCR4 receptor inhibitors, and heterobifunctional inhibitors that comprise at least one E-selectin inhibitor linked to at least one CXCR4 receptor inhibitor, and/or (2) an effective amount of at least one pharmaceutical composition comprising at least one T-cell checkpoint inhibitor and at least one other inhibitor chosen from E-selectin inhibitors, CXCR4 receptor inhibitors, and heterobifunctional inhibitors that comprise at least one E-selectin inhibitor linked to at least one CXCR4 receptor inhibitor.

In some embodiments, a method for treatment and/or prevention of at least one disease, disorder, or condition in which suppression of $T_{reg}$ cells is desired, the method comprising administering to a subject in need thereof (1) an effective amount of at least one T-cell checkpoint inhibitor and an effective amount of at least one E-selectin inhibitor and/or (2) an effective amount of at least one pharmaceutical composition comprising at least one T-cell checkpoint inhibitor and at least one E-selectin inhibitor.

In some embodiments, a method for treatment and/or prevention of at least one disease, disorder, or condition in which suppression of $T_{reg}$ cells is desired, the method comprising administering to a subject in need thereof (1) an effective amount of at least one T-cell checkpoint inhibitor and an effective amount of at least one CXCR4 receptor inhibitor and/or (2) an effective amount of at least one pharmaceutical composition comprising at least one T-cell checkpoint inhibitor and at least one CXCR4 receptor inhibitor.

In some embodiments, a method for treatment and/or prevention of at least one disease, disorder, or condition in which suppression of $T_{reg}$ cells is desired, the method comprising administering to a subject in need thereof (1) an effective amount of at least one T-cell checkpoint inhibitor and an effective amount of at least one heterobifunctional inhibitor that comprises at least one E-selectin inhibitor linked to at least one CXCR4 receptor inhibitor, and/or (2) an effective amount of at least one pharmaceutical composition comprising at least one T-cell checkpoint inhibitor and at least one heterobifunctional inhibitor that comprises at least one E-selectin inhibitor linked to at least one CXCR4 receptor inhibitor.

Any T-cell checkpoint inhibitor(s) can be used in the compositions and methods disclosed herein. In some embodiments, the at least one T-cell checkpoint inhibitor targets the PD-1 receptor and/or the CTLA-4 protein on $T_{reg}$ cells. In some embodiments, the at least one T-cell checkpoint inhibitor is a PD-L1 inhibitor. In some embodiments, the at least one T-cell checkpoint inhibitor is the anti-mPD-L1 antibody. In some embodiments, the at least one T-cell checkpoint inhibitor is chosen from nivolumab and ipilimumab.

The E-selectin inhibitors, which include the at least one E-selectin inhibitor herein, may be chosen from glycomimetics. In some embodiments, the E-selectin inhibitors are chosen from sialyl Lewis$^x$ (sLe$^x$) and sLe$^x$ mimetics. In some embodiments, the E-selectin inhibitors are chosen from small molecule glycomimetic antagonists of E-selectin, antibodies directed to E-selectin, aptamers to E-selectin, peptides directed to E-selectin, and peptidomimetics directed to E-selectin.

In some embodiments, the E-selectin inhibitors are chosen from compounds of Formula (I):

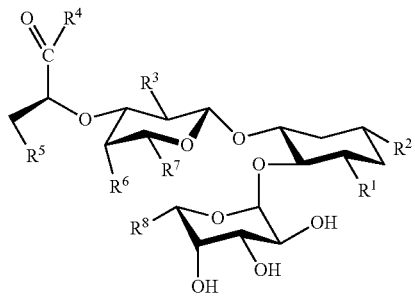

(I)

isomers of Formula (I), tautomers of Formula (I), and pharmaceutically acceptable salts of any of the foregoing, wherein:

$R^1$ is chosen from $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

$R^2$ is chosen from H, -M, and -L-M;

$R^3$ is chosen from —OH, —NH$_2$, —OC(=O)Y$^1$, —NHC(=O)Y$^1$, and —NHC(=O)NHY$^1$ groups, wherein Y$^1$ is chosen from $C_{1-8}$ alkyl, $C_{2-8}$ alkenyl, $C_{2-8}$ alkynyl, $C_{1-8}$ haloalkyl, $C_{2-8}$ haloalkenyl, $C_{2-8}$ haloalkynyl, $C_{6-18}$ aryl, and $C_{1-13}$ heteroaryl groups;

$R^4$ is chosen from —OH and —NZ$^1$Z$^2$ groups, wherein Z$^1$ and Z$^2$, which may be identical or different, are each independently chosen from H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups, wherein Z$^1$ and Z$^2$ may together form a ring;

$R^5$ is chosen from $C_3$-$C_8$ cycloalkyl groups;

$R^6$ is chosen from —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

$R^7$ is chosen from —CH$_2$OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

$R^8$ is chosen from $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

L is chosen from linker groups; and

M is a non-glycomimetic moiety chosen from polyethylene glycol, thiazolyl, chromenyl, —C(=O)NH(CH$_2$)$_{1-4}$NH$_2$, $C_{1-8}$ alkyl, and —C(=O)OY, wherein Y is chosen from $C_{1-4}$ alkyl, $C_{2-4}$ alkenyl, and $C_{2-4}$ alkynyl groups.

As would be recognized by one of ordinary skill in the art, the phrase 'isomers of Formula (I), tautomers of Formula (I), and pharmaceutically acceptable salts of any of the foregoing' includes hydrates and solvates.

In some embodiments, the E-selectin inhibitors are chosen from compounds of Formula (I), wherein the non-glycomimetic moiety comprises polyethylene glycol.

As used herein, "CXCR4 receptor inhibitors," "CXCR4 chemokine receptor inhibitors," "SDF-1 inhibitor," or "SDF-1 antagonist," and the like are used interchangeably and mean an agent inhibits the binding of the chemokine SDF-I to an SDF-I ligand (e.g., prevents the binding of SDF-I to CXCR4). Such inhibitors will typically prevent the binding of stromal derived factor-1 (SDF-1) to a CXCR4 receptor. Examples of CXCR4 chemokine receptor inhibitors are AMD-3100 (Hendrix et al., Antimicrob. Agents Chemother. 44:1667-1673, 2000); ALX40-4C (Doranz et al., AIDS Research and Human Retroviruses 17:475-486, 2001); and T134 (Arakaki et al., J. Virol. 73:1719-1723, 1999). These examples include a small organic molecule and amino acid-based molecules, such as the T22 peptide.

In some embodiments, the CXCR4 receptor inhibitors are chosen from peptides, diketopiperazine mimetics, bicyclams, tetrahydroquinolines, thiazolylisothiourea derivatives, and benzodiazepines. In some embodiments, the CXCR4 receptor inhibitors are chosen from AMD-3100, ALX40-4C, T134, and T22 peptide.

In some embodiments, the heterobifunctional inhibitors are chosen from compounds of Formula (II):

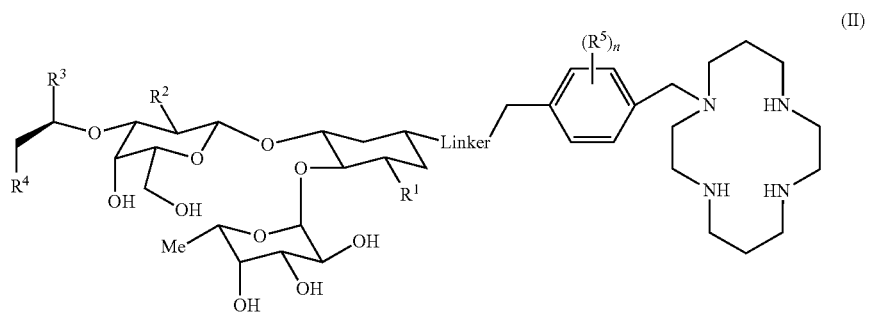

isomers of Formula (II), tautomers of Formula (II), and pharmaceutically acceptable salts of any of the foregoing, wherein:

$R^1$ is chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups;

$R^2$ is chosen from —OH, —$NH_2$, —OC(=O)$Y^1$, —NHC(=O)$Y^1$, and —NHC(=O)NH$Y^1$ groups, wherein $Y^1$ is chosen from $C_{1-8}$ alkyl, $C_{2-8}$ alkenyl, $C_{2-8}$ alkynyl, $C_{1-8}$ haloalkyl, $C_{2-8}$ haloalkenyl, $C_{2-8}$ haloalkynyl, $C_{6-18}$ aryl, and $C_{1-13}$ heteroaryl groups;

$R^3$ is chosen from —CN, —$CH_2$CN, and —C(=O)$Y^2$ groups, wherein $Y^2$ is chosen from $C_{1-8}$ alkyl, $C_{2-8}$ alkenyl, $C_{2-8}$ alkynyl, —$OZ^1$, —NHOH, —$NHOCH_3$, —NHCN, and —$NZ^1Z^2$ groups, wherein $Z^1$ and $Z^2$, which may be identical or different, are independently chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, wherein $Z^1$ and $Z^2$ may together form a ring;

$R^4$ is chosen from $C_{3-8}$ cycloalkyl groups;

$R^5$ is independently chosen from H, halo, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups;

n is chosen from integers ranging from 1 to 4; and

L is chosen from linker groups.

As would be recognized by one of ordinary skill in the art, the phrase 'isomers of Formula (II), tautomers of Formula (II), and pharmaceutically acceptable salts of any of the foregoing' includes hydrates and solvates.

In some embodiments, the heterobifunctional inhibitors are chosen from compounds of Formula (IIa):

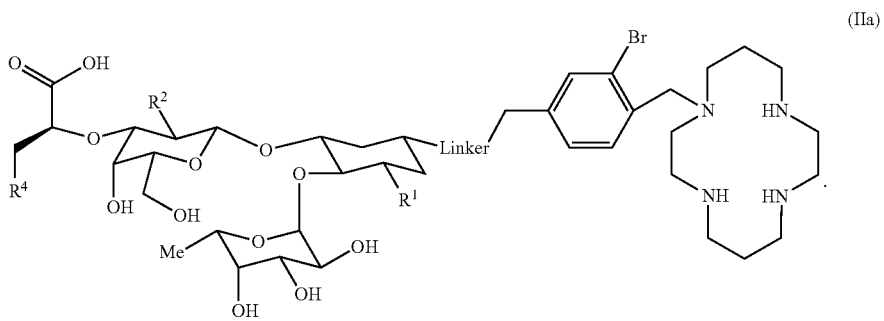

In some embodiments, the linker groups of Formula I and/or Formula II are independently chosen from groups comprising spacer groups, such spacer groups as, for example, —(CH$_2$)$_p$— and —O(CH$_2$)$_p$—, wherein p is chosen from integers ranging from 1 to 30. In some embodiments, p is chosen from integers ranging from 1 to 20. Other non-limiting examples of spacer groups include carbonyl groups and carbonyl-containing groups such as, for example, amide groups. A non-limiting example of a spacer group is

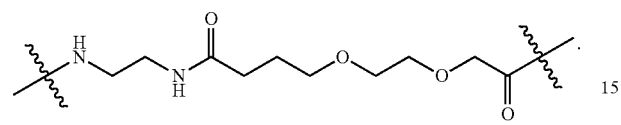

In some embodiments, the linker groups are independently chosen from

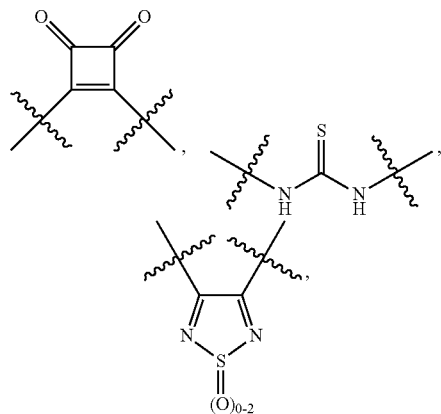

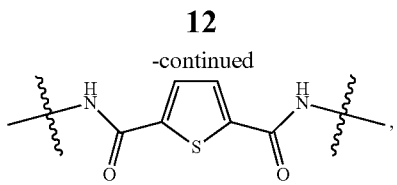

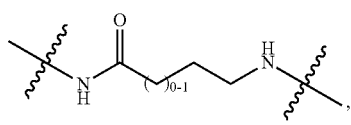

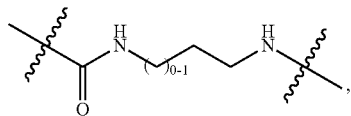

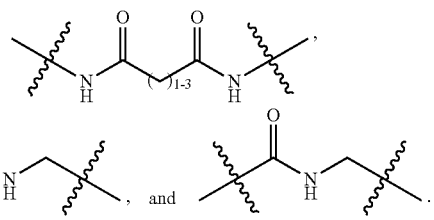

Other linker groups, such as, for example, polyethylene glycols (PEGs) and —C(=O)—NH—(CH$_2$)$_p$—C(=O)—NH—, wherein p is chosen from integers ranging from 1 to 30, or wherein p is chosen from integers ranging from 1 to 20, will be familiar to those of ordinary skill in the art and/or those in possession of the present disclosure.

In some embodiments, at least one linker group is

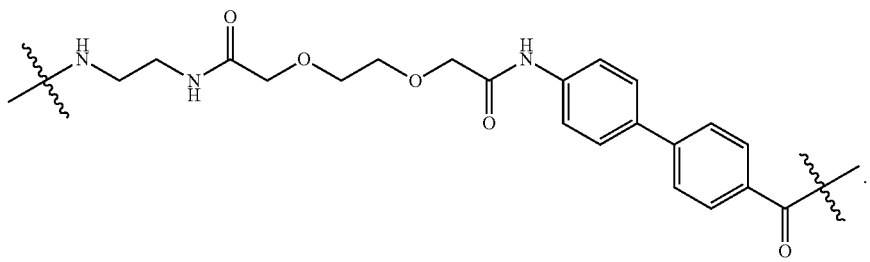 [SMILES: *NCCNC(=O)COCCOCC(=O)Nc1ccc(-c2ccc(C(*)=O)cc2)cc1]

In some embodiments, at least one linker group is

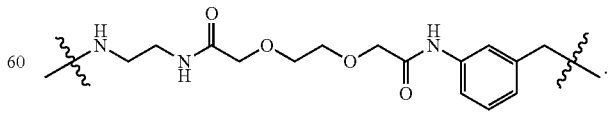

In some embodiments, at least one linker group is chosen from —C(=O)NH(CH$_2$)$_2$NH—, —CH$_2$NHCH$_2$—, and —C(=O)NHCH$_2$—. In some embodiments, at least one linker group is —C(=O)NH(CH$_2$)$_2$NH—.

In some embodiments, the at least one E-selectin inhibitor is chosen from compounds of Formula (Ia):

(Ia)

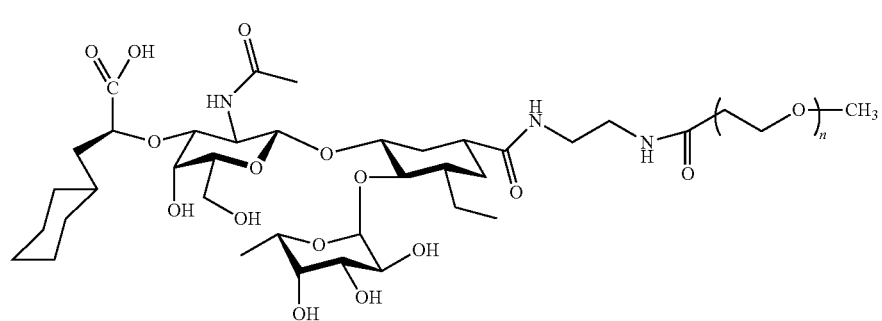

wherein n is chosen from integers ranging from 1 to 100. In some embodiments, n is chosen from 4, 8, 12, 16, 20, 24, and 28.

In some embodiments, the E-selectin inhibitors are chosen from E-selectin inhibitors disclosed in U.S. Pat. No. 9,109,002, which is hereby incorporated by reference. In some embodiments, the E-selectin inhibitor is GMI-1271. See, e.g., Price et al., "Dormant breast cancer micrometastases reside in specific bone marrow niches that regulate their transit to and from bone," Science Translational Medicine, Vol. 8(340), May 25, 2016, [DOI:10.1126/scitranslmed.aad4059]; Dutta et al., "E-Selectin Inhibition Mitigates Splenic HSC Activation and Myelopoiesis in Hypercholesterolemic Mice With Myocardial Infarction", Arterioscler Thromb Vasc Biol [DOI: 10.1161/ATVBAHA.116.307519]

In some embodiments, the heterobifunctional inhibitors are chosen from compounds of the following Formulae:

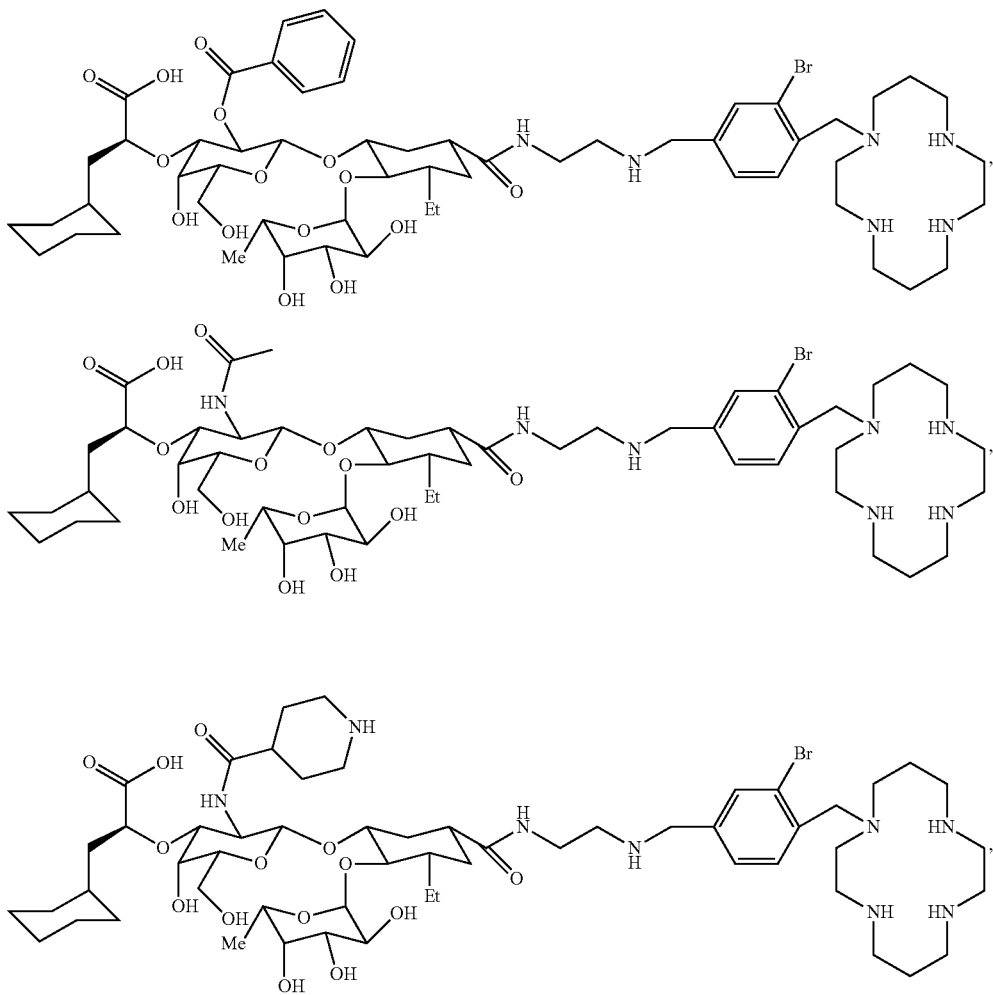

-continued
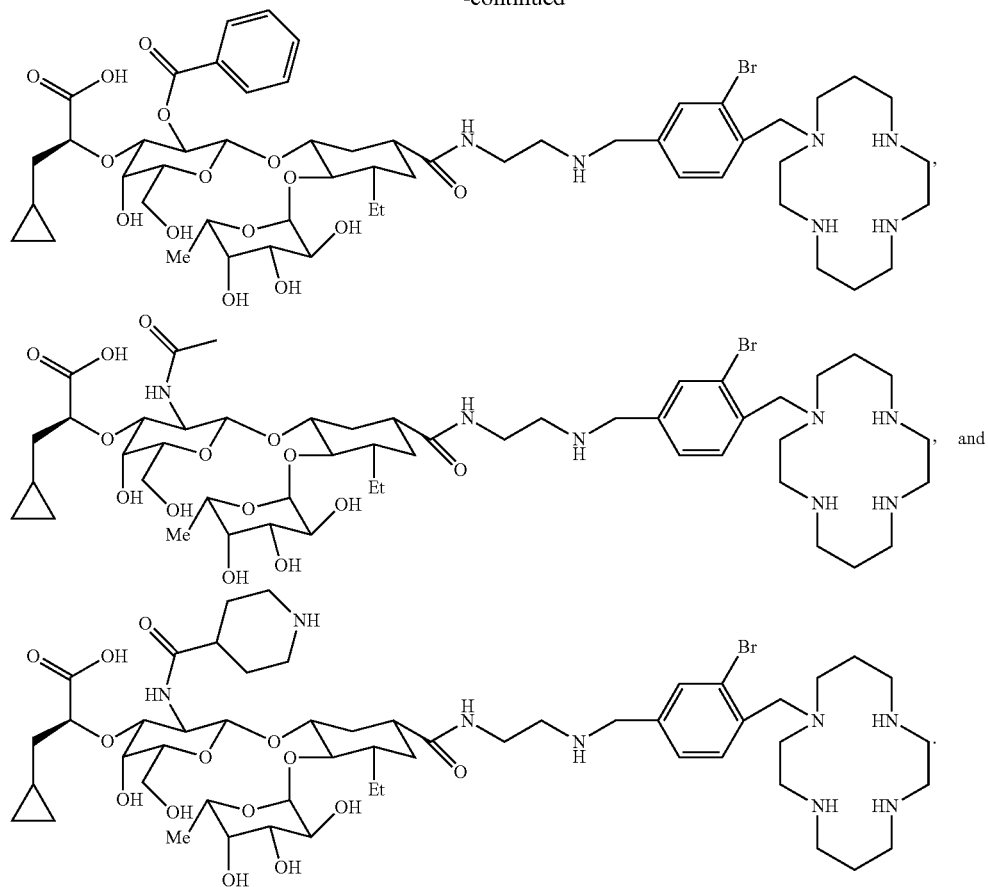
In some embodiments, the heterobifunctional inhibitors are chosen from compounds of the following Formulae:
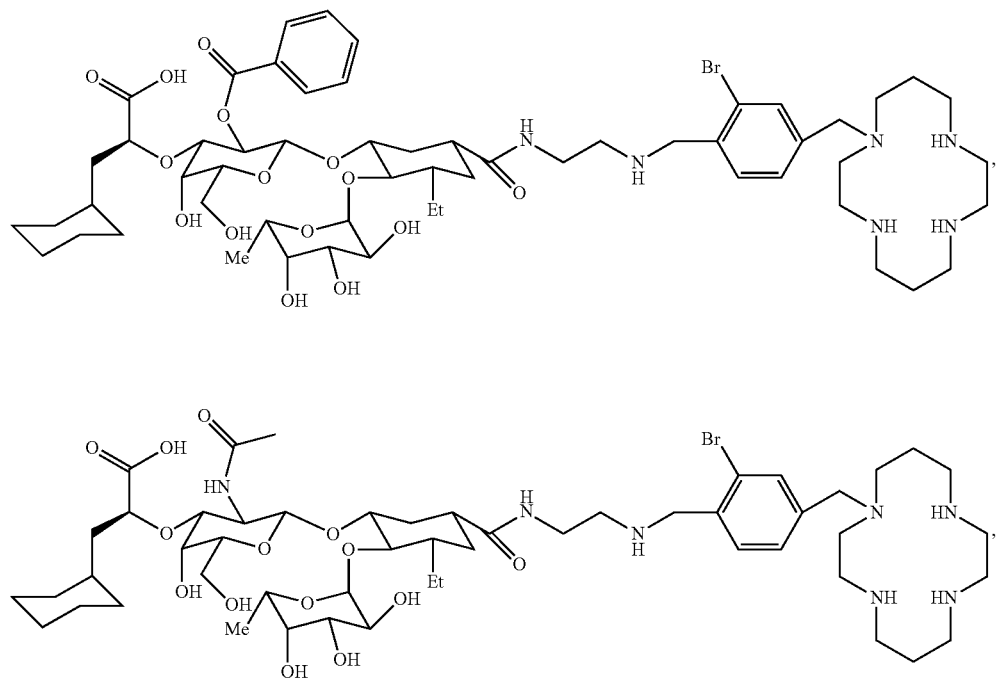

-continued

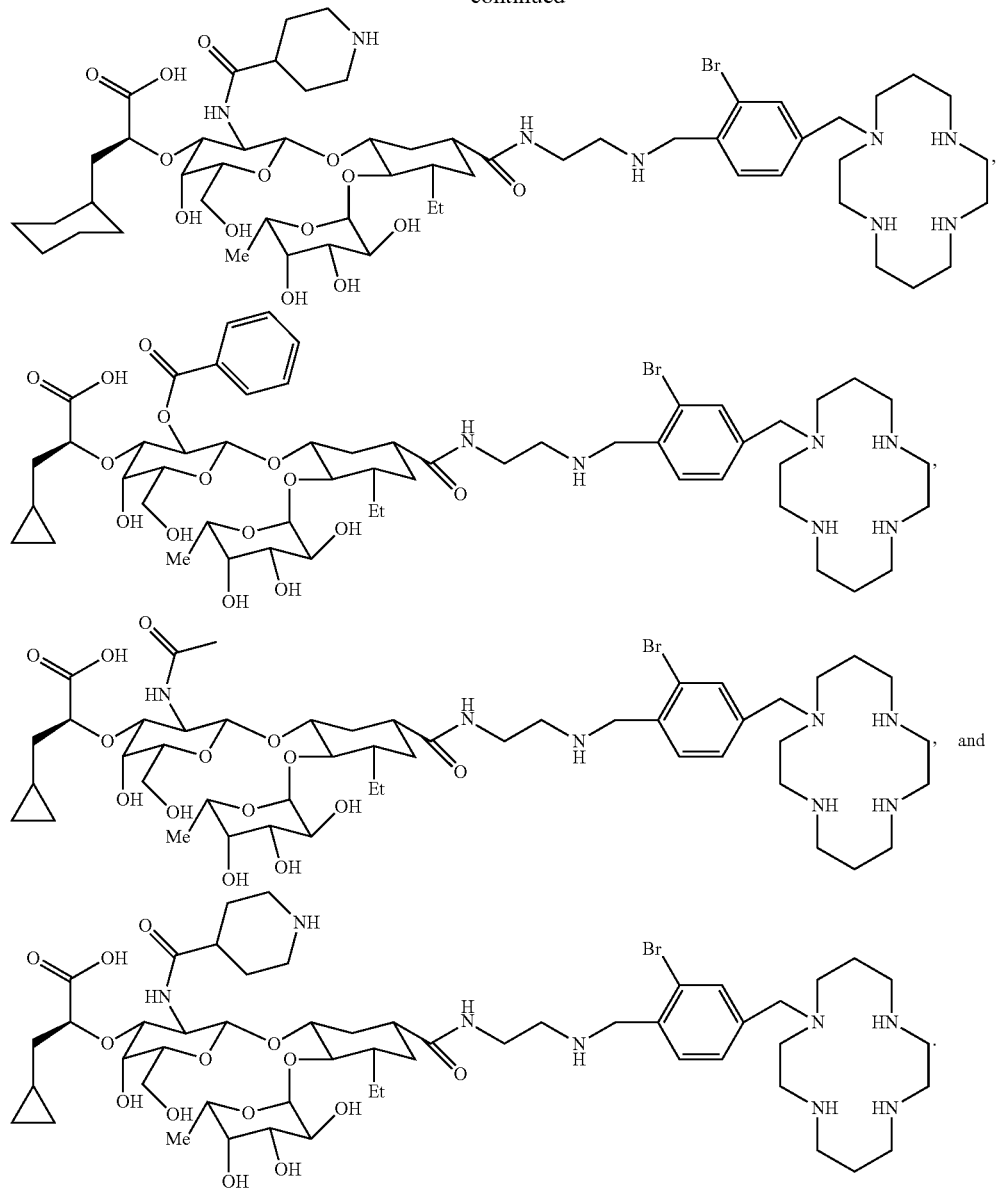

In some embodiments, the heterobifunctional inhibitors are chosen from heterobifunctional inhibitors disclosed in U.S. Pat. No. 8,410,066 and PCT/US2015/063191, which are hereby incorporated by reference. In some embodiments, the heterobifunctional inhibitor is GMI-1359. See, e.g., Steele, Maria M. et al., "A small molecule glycomimetic antagonist of E-selectin and CXCR4 (GMI-1359) prevents pancreatic tumor metastasis and improves chemotherapy [abstract]," Proceedings of the 106th Annual Meeting of the American Association for Cancer Research, 2015 Apr. 18-22, Philadelphia, Pa.; Philadelphia (Pa.): AACR, Cancer Res 2015, 75(15 Suppl):Abstract nr 425. doi:10.1158/1538-7445.AM2015-425; Gravina, Giovanni L. et al., "Dual E-selectin and CXCR4 inhibition reduces tumor growth and increases the sensitivity to docetaxel in experimental bone metastases of prostate cancer [abstract]," Proceedings of the 106th Annual Meeting of the American Association for Cancer Research, 2015 Apr. 18-22, Philadelphia, Pa.; Philadelphia (Pa.): AACR, Cancer Res 2015, 75(15 Suppl): Abstract nr 428. doi:10.1158/1538-7445.AM2015-428, all of which are incorporated by reference.

In some embodiments, the at least one disease, disorder, or condition is chosen from cancers. In some embodiments, the cancers are chosen from liquid cancers (e.g., MM, ALL, and AML) and solid cancers (e.g., prostate cancer). In some embodiments, the cancers are chosen from liquid cancers. In some embodiments, the cancers are chosen from solid cancers. In some embodiments, the subject is treated locally at a tumor of a solid cancer.

In some embodiments, the rate of increase of cancerous cells (e.g., tumor growth or cancer cell proliferation) is reduced or halted. In some embodiments, the number of cancer cells is reduced. In some embodiments, the cancer cells are eliminated. In some embodiments, metastasis of cancer cells reduced. In some embodiments, the metastasis of cancer cells is halted. In some embodiments, infiltration of the cancer into bone marrow is reduced or halted.

In some embodiments, the subject has cancer and has received or will receive chemotherapy and/or radiotherapy. In some embodiments, the chemotherapy comprises administering a therapeutically effective amount of at least one compound chosen from platinum, cisplatin, carboplatin, oxaliplatin, mechlorethamine, cyclophosphamide, chlorambucil, azathioprine, mercaptopurine, vincristine, vinblastine, vinorelbine, vindesine, etoposide, teniposide, paclitaxel, docetaxel, irinotecan, topotecan, amsacrine, etoposide, etoposide phosphate, teniposide, 5-fluorouracil (5-FU), leucovorin, methotrexate, gemcitabine, taxane, leucovorin, mitomycin C, tegafur-uracil, idarubicin, fludarabine, mitoxantrone, ifosfamide and doxorubicin.

In some embodiments, the chemotherapy comprises administration of bortezomib. In some embodiments, the chemotherapy comprises administration of gemcitabine.

In some embodiments, the at least one disease, disorder, or condition is chosen from a bacterial infection, a viral infection, and a condition relating to a bacterial or viral infection. In some embodiments, the viral infection is an HIV infection and/or the patient has been diagnosed with AIDS or an HIV-related illness. In some embodiments, the bacterial infection is sepsis and/or the subject has been diagnosed with a septic condition.

In some embodiments, the administration to the subject of at least one T-cell checkpoint inhibitor and the at least one other inhibitor suitably overlap so that the therapeutic effect of one agent (i.e. the time period post use where a measurable benefit to the patient is observed) is concurrent, at least at some point, with the period of therapeutic effect of the second agent. In some embodiments, the at least one T-cell checkpoint inhibitor and the at least one other inhibitor are administered concurrently. In some embodiments, the at least one T-cell checkpoint inhibitor and the at least one other inhibitor are administered at the different times. In some embodiments, the at least one T-cell checkpoint inhibitor and the at least one other inhibitor are administered sequentially.

In some embodiments, the at least one T-cell checkpoint inhibitor and the at least one other inhibitor are administered in a single pharmaceutical composition.

In some embodiments, the at least one T-cell checkpoint inhibitor and the at least one other inhibitor are administered in separate pharmaceutical compositions.

In some embodiments, the pharmaceutical composition(s) further comprises at least one additional pharmaceutically acceptable ingredient.

In pharmaceutical dosage forms, any one or more of the compounds of the present disclosure may be administered in the form of a pharmaceutically acceptable derivative, such as a salt, and/or it/they may also be used alone and/or in appropriate association, as well as in combination, with other pharmaceutically active compounds.

An "effective amount" or "therapeutically effective amount" refers to an amount of a compound of the present disclosure or a composition comprising at least one such compound that, when administered to a subject, either as a single dose or as part of a series of doses, is effective to produce at least one therapeutic effect. For example, in the case of cancer, a therapeutic effect can be killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

Optimal doses may generally be determined using experimental models and/or clinical trials. Design and execution of pre-clinical and clinical studies for each of the therapeutics (including when administered for prophylactic benefit) described herein are well within the skill of a person of ordinary skill in the relevant art. The optimal dose of a therapeutic may depend upon the body mass, weight, and/or blood volume of the subject. The minimum dose that is sufficient to provide effective therapy may be used in some embodiments. Subjects may generally be monitored for therapeutic effectiveness using assays suitable for the disease or condition being treated or prevented, which assays will be familiar to those having ordinary skill in the art and are described herein. The level of a compound that is administered to a subject may be monitored by determining the level of the compound (or a metabolite of the compound) in a biological fluid, for example, in the blood, blood fraction (e.g., serum), and/or in the urine, and/or other biological sample from the subject. Any method practiced in the art to detect the compound, or metabolite thereof, may be used to measure the level of the compound during the course of a therapeutic regimen.

The dose of a compound described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease or disorder may be determined according to parameters understood by a person of ordinary skill in the medical art.

Pharmaceutical compositions may be administered in any manner appropriate to the disease or disorder to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the pharmaceutical composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively delivers an effective amount of the compound. Non-limiting suitable administrative routes include topical, oral, nasal, intrathecal, enteral, buccal, sublingual, transdermal, rectal, vaginal, intraocular, subconjunctival, sublingual, and parenteral administration, including subcutaneous, intravenous, intramuscular, intrasternal, intracavernous, intrameatal, and intraurethral injection and/or infusion.

The pharmaceutical composition described herein may be sterile aqueous or sterile non-aqueous solutions, suspensions or emulsions, and may additionally comprise at least one pharmaceutically acceptable excipient (i.e., a non-toxic material that does not interfere with the activity of the active ingredient). Such compositions may be in the form of a solid, liquid, or gas (aerosol). Alternatively, the compositions described herein may be formulated as a lyophilizate, or compounds described herein may be encapsulated within liposomes using technology known in the art. The pharmaceutical compositions may further comprise at least one additional pharmaceutically acceptable ingredient, which may be biologically active or inactive. Non-limiting examples of such ingredients include buffers (e.g., neutral buffered saline or phosphate buffered saline), carbohydrates (e.g., glucose, mannose, sucrose or dextrans), mannitol, proteins, polypeptides, amino acids (e.g., glycine), antioxidants, chelating agents (e.g., EDTA and glutathione), stabilizers, dyes, flavoring agents, suspending agents, and preservatives.

Any suitable excipient or carrier known to those of ordinary skill in the art for use in pharmaceutical compositions may be employed in the compositions described herein. Excipients for therapeutic use are well known, and are described, for example, in Remington: The Science and Practice of Pharmacy (Gennaro, $21^{st}$ Ed. Mack Pub. Co., Easton, Pa. (2005)). In general, the type of excipient is selected based on the mode of administration, as well as the chemical composition of the active ingredient(s). Pharmaceutical compositions may be formulated for the particular mode of administration. For parenteral administration, pharmaceutical compositions may further comprise water, saline, alcohols, fats, waxes, and buffers. For oral administration, pharmaceutical compositions may further comprise at least one ingredient chosen, for example, from any of the aforementioned excipients, solid excipients and carriers, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose, and magnesium carbonate.

The pharmaceutical compositions (e.g., for oral administration or delivery by injection) may be in the form of a liquid. A liquid pharmaceutical composition may include, for example, at least one the following: a sterile diluent such as water for injection, saline solution, physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity, such as sodium chloride or dextrose. A parenteral preparation can be enclosed in ampoules, disposable syringes or multiple dose vials made of glass or plastic. In some embodiments, the pharmaceutical composition comprises physiological saline. In some embodiments, the pharmaceutical composition an injectable pharmaceutical composition, and in some embodiments, the injectable pharmaceutical composition is sterile.

For oral formulations, at least one of the compounds of the present disclosure can be used alone or in combination with at least one additive appropriate to make tablets, powders, granules and/or capsules, for example, those chosen from conventional additives, disintegrators, lubricants, diluents, buffering agents, moistening agents, preservatives, coloring agents, and flavoring agents. The pharmaceutical compositions may be formulated to include at least one buffering agent, which may provide for protection of the active ingredient from low pH of the gastric environment and/or an enteric coating. A pharmaceutical composition may be formulated for oral delivery with at least one flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable; the formulation may also provide a relatively constant level of active component release. The amount of active therapeutic contained within a sustained release formulation depends upon the site of implantation, the rate and expected duration of release, and the nature of the condition to be treated or prevented.

The pharmaceutical compositions described herein can be formulated as suppositories by mixing with a variety of bases, such as emulsifying bases or water-soluble bases. The pharmaceutical compositions may be prepared as aerosol formulations to be administered via inhalation. The compositions may be formulated into pressurized acceptable propellants, such as dichlorodifluoromethane, propane, nitrogen and the like.

The compounds of the present disclosure and pharmaceutical compositions comprising these compounds may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques, such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneräs et al., *J. Pharm. Pharmacol.* 54:499-508 (2002); Karande et al., *Pharm. Res.* 19:655-60 (2002); Vaddi et al., *Int. J. Pharm.* 91:1639-51 (2002); Ventura et al., *J. Drug Target* 9:379-93 (2001); Shokri et al., *Int. J. Pharm.* 228(1-2):99-107 (2001); Suzuki et al., *Biol. Pharm. Bull.* 24:698-700 (2001); Alberti et al., *J. Control Release* 71:319-27 (2001); Goldstein et al., *Urology* 57:301-5 (2001); Kiijavainen et al., *Eur. J. Pharm. Sci.* 10:97-102 (2000); and Tenjarla et al., *Int. J. Pharm.* 192: 147-58 (1999).

Routes of administration include, but are not limited to, intradermal, intramuscular, intraperitoneal, intravenous, intrathecal, and subcutaneous routes. In some embodiments, the compounds or compositions are administered locally (i.e., near a cancer tumor). In some embodiments, one or more of the compounds or compositions are administered using different routes of administration.

The compounds or pharmaceutical composition(s) can be administered in one or more doses and treatment regimens, which may be the same or different. In one embodiment, each of the compounds or pharmaceutical composition(s) is administered in an amount ranging from about 1 mg/kg to about 50 mg/kg once a day. In other embodiments, the dosage may be at any dosage including, but not limited to, about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg.

In some embodiments, the compounds or pharmaceutical composition(s) are administered in any of these amounts and ranges once a day, more than once a day, every other day, every two days, etc. In some embodiments, the at least one T-cell checkpoint inhibitor and the at least one E-selectin inhibitor, CXCR4 receptor inhibitor, and/or heterobifunctional inhibitor, wherein an E-selectin inhibitor is linked to a CXCR4 receptor inhibitor, are administered concurrently and/or in the same number of treatments per day. In some embodiments, the at least one T-cell checkpoint inhibitor and the at least one E-selectin inhibitor, CXCR4 receptor inhibitor, and/or heterobifunctional inhibitor, wherein an E-selectin inhibitor is linked to a CXCR4 receptor inhibitor, are administered on different schedules. One of more treatment cycles may be repeated, and any number of cycles is contemplated. The number of treatments per day and the amount per dose for each compound or pharmaceutical composition may vary during each cycle.

Kits comprising unit doses of at least one compound or pharmaceutical composition of the present disclosure, for example, in oral or injectable doses, are provided. Such kits may include a container comprising the unit dose, an informational package insert describing the use and attendant benefits of the therapeutic in treating the pathological condition of interest, and/or optionally an appliance or device for delivery of the at least one compound and/or pharmaceutical composition comprising the same.

EXAMPLES

Overview

The primary goal of the studies was to determine the anti-cancer activity of treatments comprising the administration of T-cell checkpoint inhibitor with an E-selectin inhibitor and/or a CXCR4 receptor inhibitor. The T-cell checkpoint inhibitor used was an anti-mPD-L1 antibody. Heterobifunctional inhibitor GMI-1359, an inhibitor of both E-selectins and CXCR4 receptors, was used.

The anti-cancer activity of an anti-mPD-L1 antibody (10F.9G2) and GMI-1359 was compared to a rat isotype control antibody against indeterminate subcutaneous CT26.WT carcinoma xenografts in female Balb/c mice. An immune profile of each mouse was determined by sampling tumors and spleens, staining for several markers of an active immune response, and detecting the levels of these markers via flow cytometry. Flow cytometry markers included: T-Cells ($CD4^+$ and $CD8^+$), Regulatory T-Cells ($T_{regs}$). ($CD4^+/CD25^+/FoxP3^+$), MDSCs ($CD11b^+/Gr1^+$) and co-expression of $CCR7^+$ and $CD62^+$ added to the existing CD4/CD8 panel.

Materials & Methods

Chemicals:

GMI-1359 (MW=1115 g/mol, Lot #50.279) was obtained as a pre-weighed crystalline powder. Upon receipt, it was stored protected from light at −20° C. GMI-1359 was formulated in sterile saline. The vehicle (sterile saline) was added to the pre-weighed compound to achieve a concentration of 0.1 mg/ml. The formulation was then stirred overnight at 20° C. The final dosing solution was clear and colorless with a pH of 9.99. The dosing formulation was prepared fresh weekly and was stored protected from light at 20° C. when not in use. Dose levels of GMI-1359 were given as bulk drug substance.

InVivoMAb anti-KLH; Rat IgG2b, LTF-2 (5.8 mg/ml, Lot #5535-3-6-7/0515) was obtained as a clear, colorless stock solution. Upon receipt, it was stored protected from light at 4° C. The dosing solution was prepared by diluting the stock solution with PBS (phosphate buffered saline) to a final concentration of 1 mg/ml. The final dosing solution was clear and colorless with a pH of 7.29. The dosing formulation was prepared once weekly and was stored protected from light at 4° C. when not in use. On each dosing day, the dosing formulations were stored on ice prior to and during dosing.

Anti-mPD-L1 (10F.9G2, 6.39 mg/ml, Lot #5592-4-6/0615) was obtained as a clear, colorless stock solution. Upon receipt, it was stored protected from light at 4° C. The dosing solution was prepared by diluting the stock solution with PBS 1 mg/mi. The final dosing solution was clear and colorless with a pH of 6.96. The formulation was prepared once weekly and was stored protected from light at 4° C. when not in use. On each dosing day, the dosing formulations were stored on ice prior to and during dosing.

Animals and Husbandry:

Female Harlan Balb/c mice (BALB/cAnNHsd) were used in this study. They were 6-7 weeks old on Day 1 of the experiment. The animals were fed irradiated Harlan 2918.15 Rodent Diet and water ad libitum. Animals were housed in static cages with Bed-O'Cobs™ bedding inside Biobubble® Clean Rooms that provide H.E.P.A filtered air into the bubble environment at 100 complete air changes per hour. All treatments, body weight determinations, and tumor measurements were carried out in the bubble environment. The environment was controlled to a temperature range of 70° ±2F and a humidity range of 30-70%. All procedures carried out in these experiments were conducted in compliance with all the laws, regulations and guidelines of the National Institutes of Health (NIH) in an AAALAC accredited facility.

Cell Preparation:

CT26.WT cells were grown in RPMI 1640 medium which was modified with 1 mM Na pyruvate, 10 mM HEPES, 2.5 g/L glucose and supplemented with 10% nonheat-inactivated Fetal Bovine Serum (FBS) and 1% 100X Penicillin/Streptomycin/L-Glutamine (PSG). The growth environment was maintained in an incubator with a 5% CO2 atmosphere at 37° C.

When expansion was complete, the cells were trypsinized using 0.25% trypsin-EDTA solution. Following cell detachment, the trypsin was inactivated by dilution with complete growth medium and any clumps of cells were separated by pipetting. The cells were centrifuged at 200 rcf for 8 minutes at 4° C., the supernatant was aspirated, and the pellet was re-suspended in cold Dulbecco's Phosphate Buffered Saline (DPBS) by pipetting. An aliquot of the homogeneous cell suspension was diluted in a trypan blue solution and counted using a Luna automated cell counter. The preimplantation cell viability was 92%. The cell suspension was centrifuged at 200 rcf for 8 minutes at 4° C. The supernatant was aspirated and the cell pellet was re-suspended in cold serum-free medium to generate a final concentration of 2.50E+06 trypan-excluding cells/ml. The cell suspension was maintained on wet ice during implantation. Following implantation, an aliquot of the remaining cells was diluted with a trypan blue solution and counted to determine the post-implantation cell viability (91%).

Test animals were implanted subcutaneously, high in the axilla (just under the fore limb) on Day 0 with 5.00E+05 cells in 0.2 ml of serum-free medium using a 27-gauge needle and syringe.

The following classification was used in the following experiments. Of all the CD8$^+$ cells the $T_{naive}$ population was CD62hi CD44$^-$; the $T_{CM/SCM}$ population was CD62hi CD44$^+$; and the TEM population was CD44$^+$ CD62$^-$ population. An increase in the TCM/SCM mouse cell population was observed (see FIGS. 1 through 6).

Experimental Study Groups:

All mice were sorted into study groups based on body weights such that the mean body weights in each group was within 10% of the overall mean. Treatment began on Day 3.

Groups 1 and 7:

The Vehicle Control (saline) was dosed intraperitoneally, every day for 20 days (Days 3-22) and every day for 12 days (Days 3-14) for Groups 1 and 7, respectively.

Groups 2 and 8:

GMI-1359 was dosed intraperitoneally at 40 mg/kg, every day for 20 days (Days 3-22) and every day for 12 days (Days 3-14) for Groups 2 and 8, respectively.

Groups 3 and 9:

Anti-KLH; Rat IgG2b, LTF-2 was dosed intraperitoneally at 10 mg/kg, every 3 days for 2 treatments, with 3 days off for 2.5 weeks (Days 3, 6, 10, 13 and 17) for Group 3. Group 9 was dosed intraperitoneally at 10 mg/kg, every 3 days for 2 treatments, with 3 days off for 2 weeks (Days 3, 6, 10 and 13).

Groups 4 and 10: Anti-mPD-L1, 10F.9G2 was dosed intraperitoneally at 10 mg/kg, every 3 days for 2 treatments, with 3 days off for 2.5 weeks (Days 3, 6, 10, 13 and 17) for Group 4.

Group 10 was dosed intraperitoneally at 10 mg/kg, every 3 days for 2 treatments, with 3 days off for 2 weeks (Days 3, 6, 10 and 13).

Groups 5 and 11:

GMI-1359 was dosed in combination with anti-KLH; Rat IgG2b, LTF intraperitoneally at 40 mg/kg and 10 mg/kg, respectively. In Group 5, GMI-1359 was dosed once a day for 20 days (Days 3-22) and anti-KLH; Rat IgG2b was given every 3 days for 2 treatments, with 3 days off for 2.5 weeks (Days 3, 6, 10, 13 and 17). In Group 11, GMI-1359 was dosed once a day for 12 days (Days 3-14) and anti-KLH; Rat IgG2b was dosed every 3 days for 2 treatments, with 3 days off for 2 weeks and (Days 3, 6, 10 and 13). On days when both compounds were dosed, GMI-1359 was given first and then anti-KLH; Rat IgG2b, LTF was given within minutes thereafter.

Groups 6 and 12: GMI-1359 and anti-mPD-L1, 10F.9G2 were dosed in a combination regimen intraperitoneally at 40 mg/kg and 10 mg/kg, respectively. In Group 6, GMI-1359 was dosed once a day for 20 days (Days 3-22) and anti-mPD-L1, 10F.9G2 was given every 3 days for 2 treatments, with 3 days off for 2.5 weeks and (Days 3, 6, 10, 13, and 17).

In Group 12, GMI-1359 was dosed once a day for 12 days (Days 3-14) and anti-mPD-L1 was dosed every 3 days for 2 treatments, with 3 days off for 2 weeks (Days 3, 6, 10, and 13). On days in which both compounds were given, GMI-1359 was given first and anti-mPD-L1, 10F.9G2 was dosed within minutes thereafter.

All mice were dosed according to individual body weight on the day of treatment (0.2 ml/20 g).

The toxicity and efficacy data for the various treatment groups is presented in FIG. 19.

Sampling:

At 24 hours after the final dose of GMI-1359 (Day 15), all mice from Groups 7-12 were euthanized for tumor and spleen collection. All mice were euthanized via over exposure to carbon dioxide. The tumors and spleens were excised and placed in a labeled 5 mL sampling tube filled with cold PBS and placed on ice. The tumors and spleens were provided to the Molecular Imaging's in vitro group for flow cytometric analysis.

Figure 1:
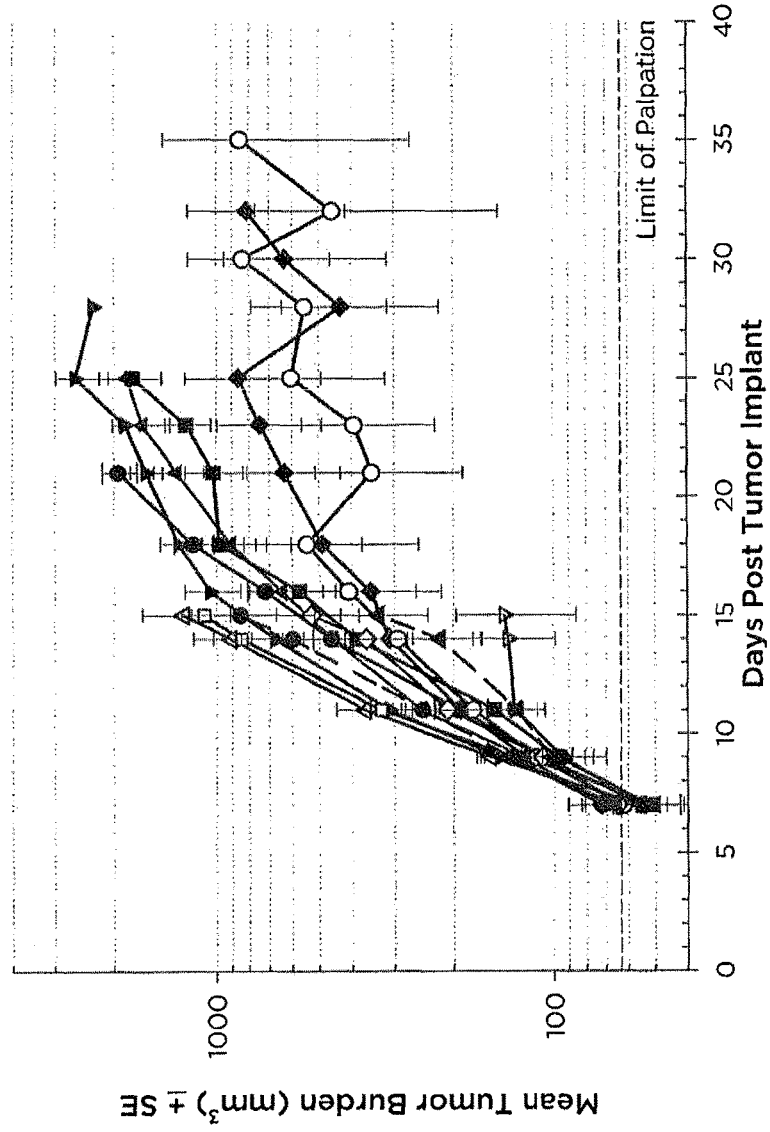
FIG. 1 is a graph of the mean tumor growth, shown as mean tumor burden in mm³, in 12 groups of experimental mice (control groups included as well), with standard error.
Figure 2:
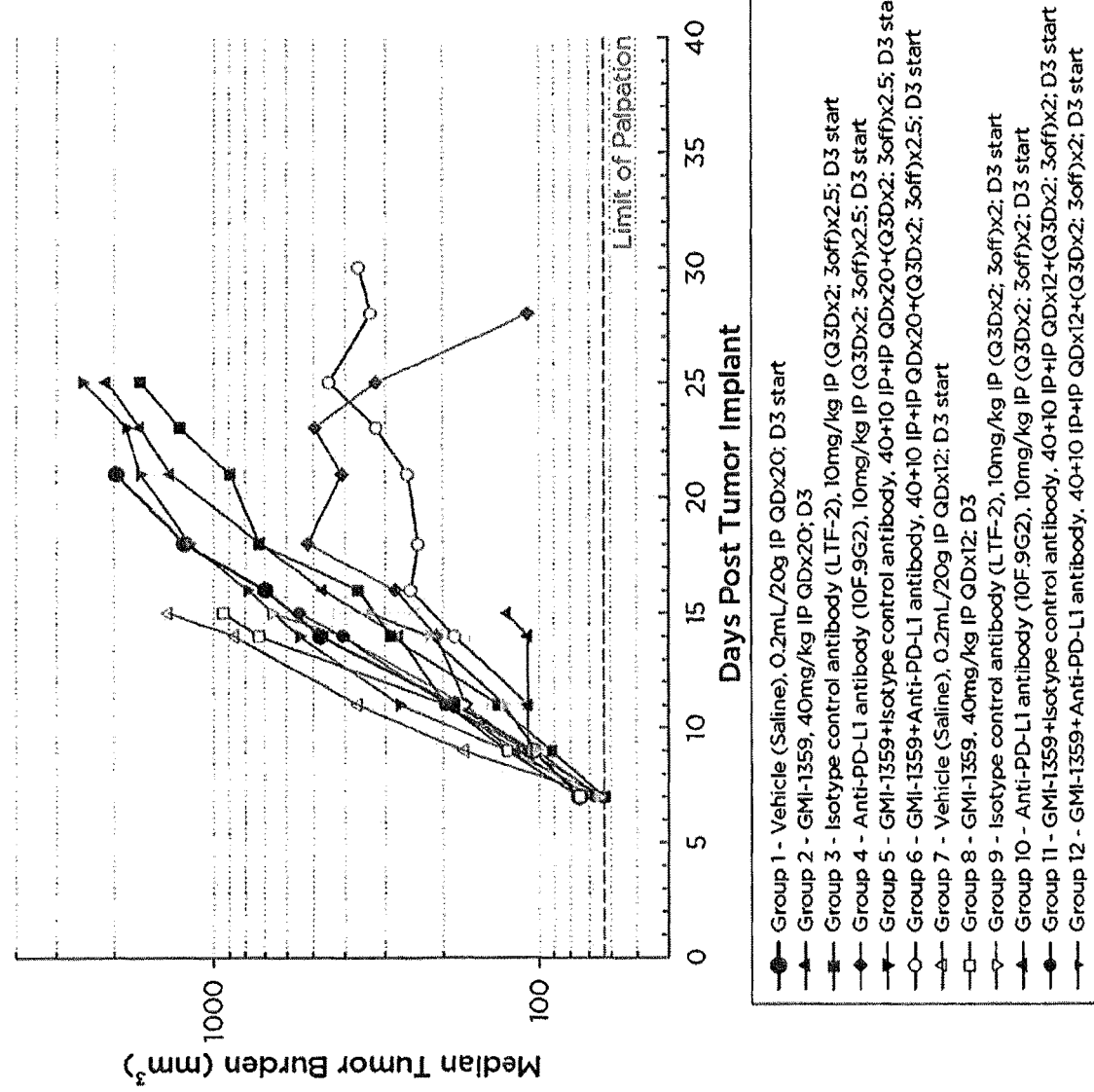
FIG. 2 is a graph of the median tumor growth, shown as median tumor burden in mm³, in 12 groups of experimental mice (control groups included as well), with standard error.
Figure 3A:
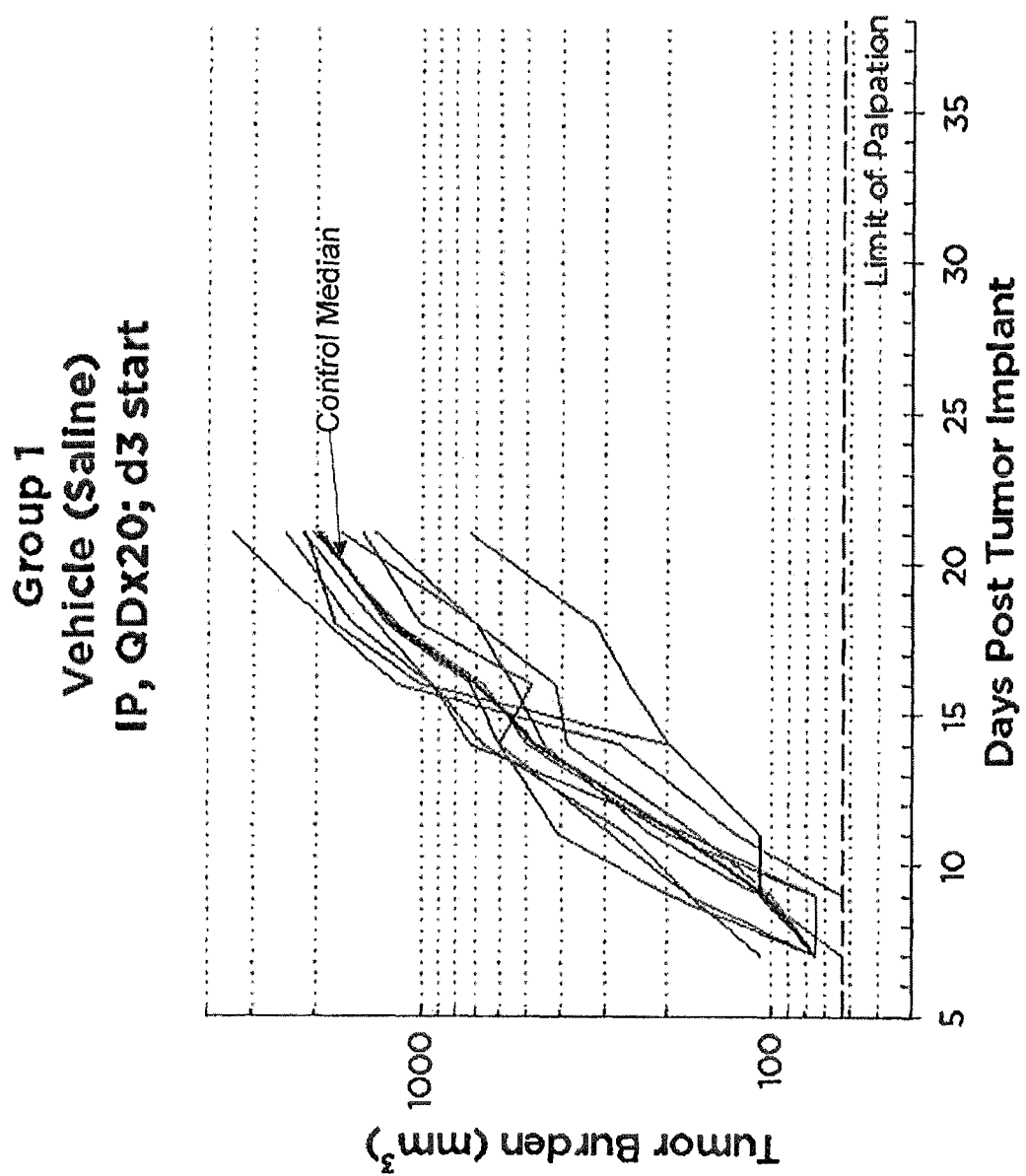
FIGS. 3A-D are graphs of the tumor growth of individual mice of group 1 (saline control group, FIG. 3A); group 2 (GMI-1359 treatment, FIG. 3B); group 3 (isotype control antibody LTF-2, FIG. 3C); and group 4 (anti-PD-L1 antibody treatment, FIG. 3D), shown as tumor burden in mm³ and including control median and group median.
Figure 3B:
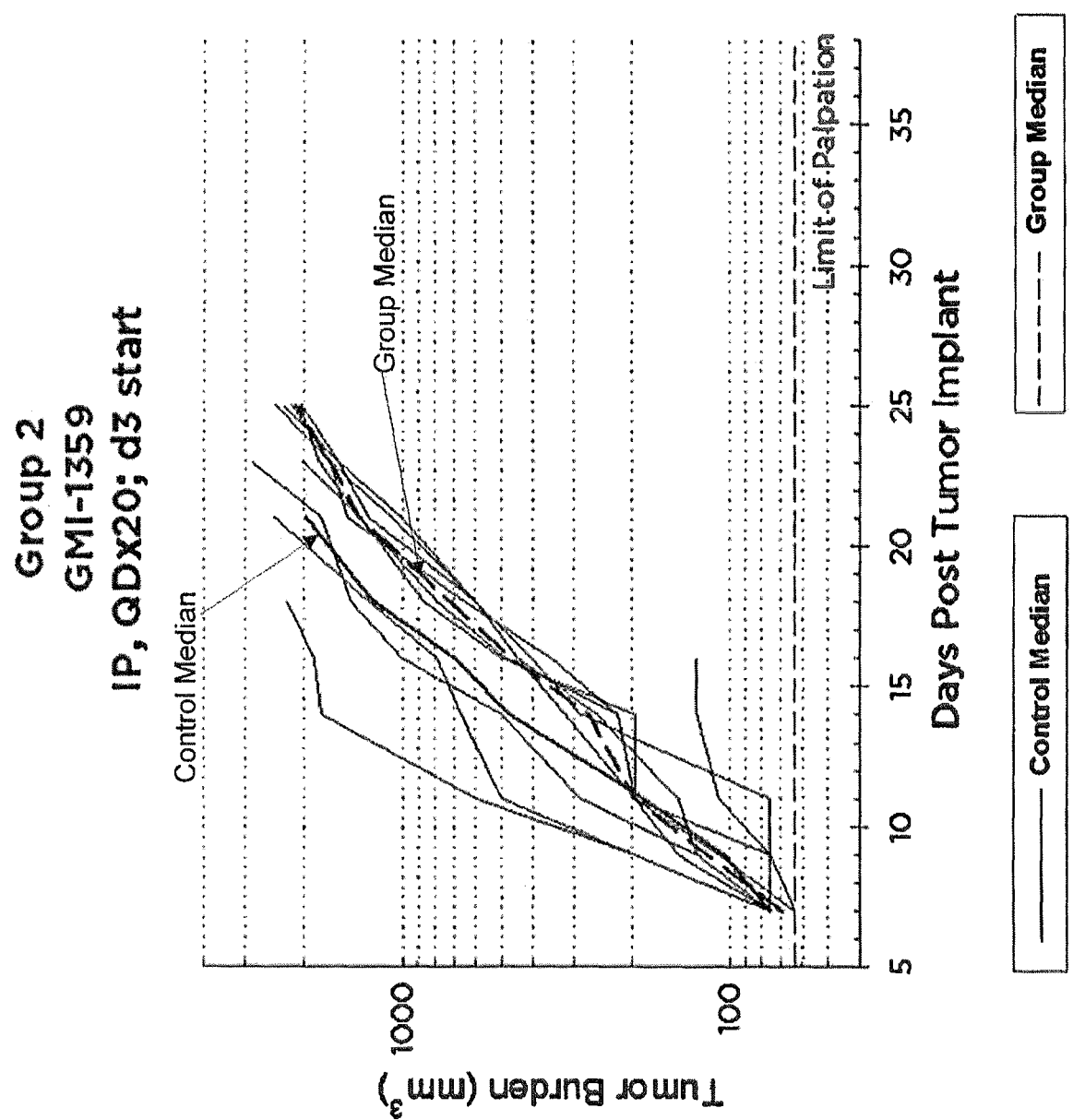
Figure 3C:
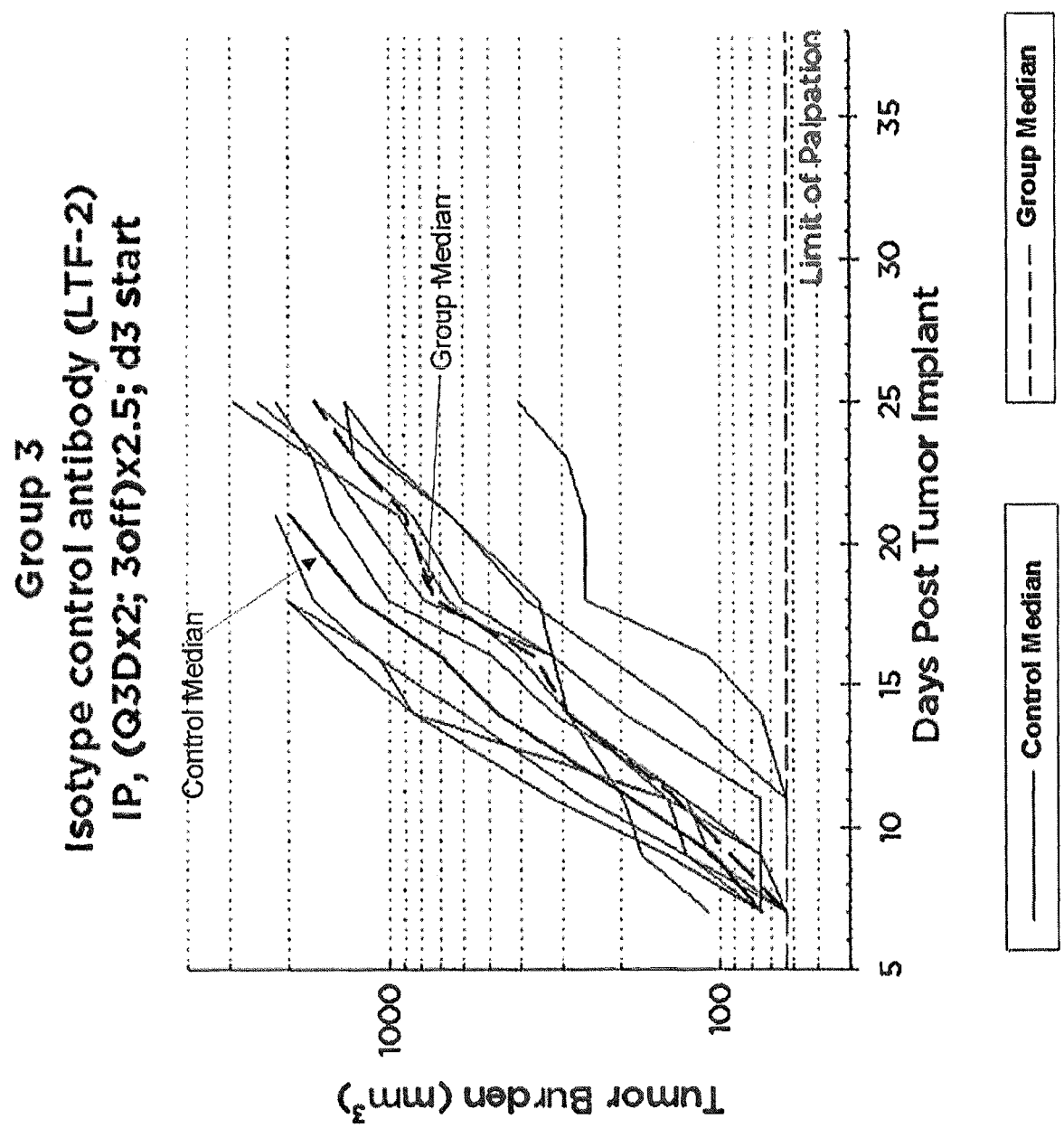
Figure 3D:
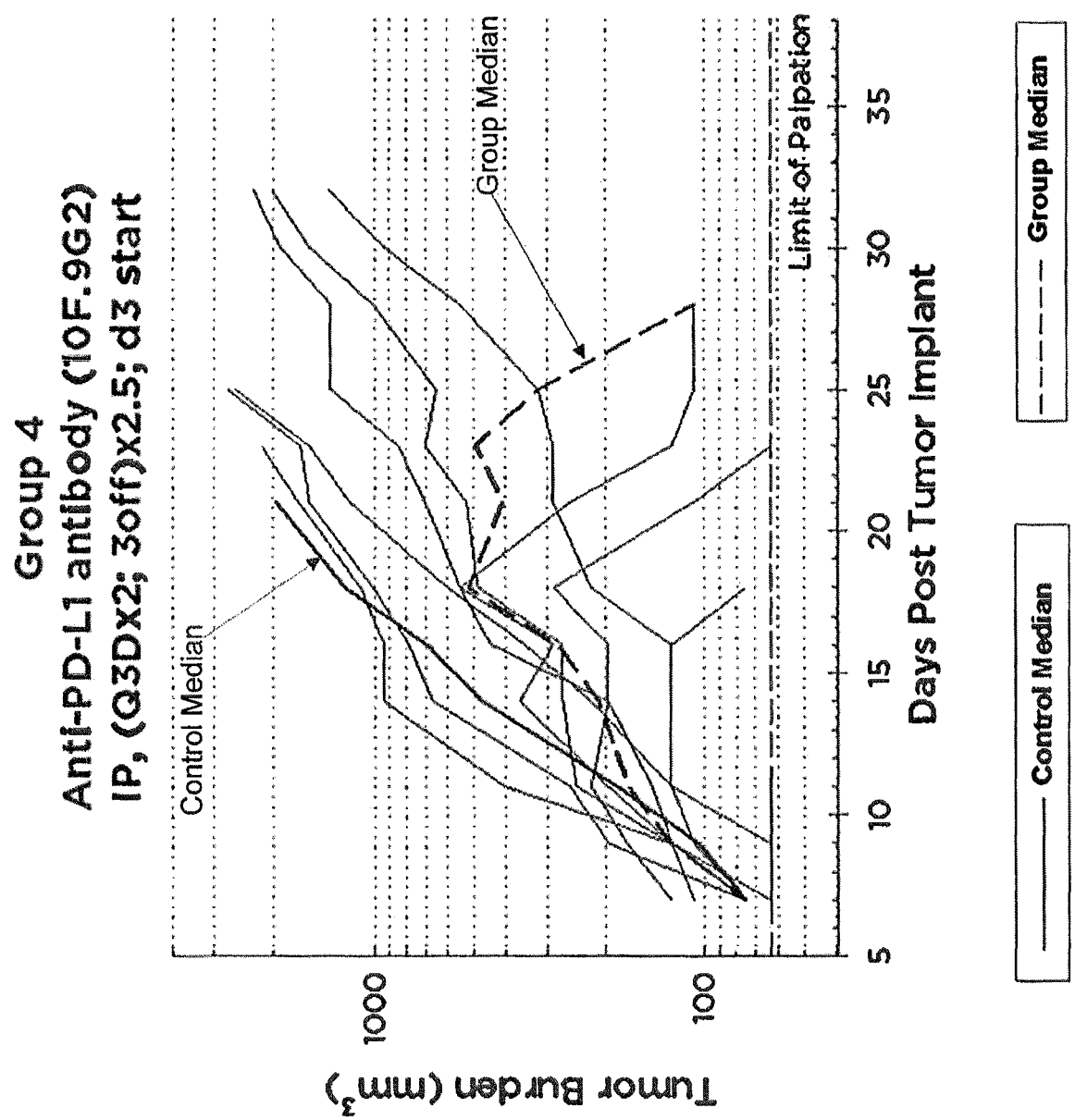

Measurement and Endpoints:

Testing in this experiment was generally carried out adhering to the general principles established by the groups of Schabel, Skipper, Griswold, Corbett, Leopold, Ross and the NCI (1-7). Tumor measurements were recorded three times weekly. Tumor burden (mm$^3$) was estimated from caliper measurements by the formula for the volume of a prolate ellipsoid assuming unit density as: Tumor burden (mm$^3$)=(L×W$^2$)/2, where L and W are the respective orthogonal tumor length and width measurements (mm). Mean tumor burdens of each of the test groups are shown in FIG. 1. Median tumor burdens of each of the test groups are shown in FIG. 2. Tumor burdens for individuals in groups 1-4, as well as the group median for each of groups 1-4, are plotted in FIGS. 3A-D, respectively; tumor burdens for individuals in groups 5-8, as well as the group median for each of groups 5-8, are plotted in FIGS. 4A-D, respectively; and tumor burdens for individuals in groups 9-12, as well as the group median for each of groups 9-12, are plotted in FIGS. 5A-D, respectively. The median tumor burden for the control group (i.e., the median for group 1 (saline)) is also plotted in each of FIGS. 3A-D, 4A-D, and 5A-D for reference.

Animals with tumors in excess of 2000 mm$^3$ were euthanized, as were those found in obvious distress or in a moribund condition. Treatment started on day 3, when there were no measurable tumors, effectively preventing analysis of tumor regressions. The nature of the therapies examined suggested that little or no on-target immune-based therapeutic effect was likely prior to Day 10. For this reason, and because all of the mice had evident tumors, Day 9 was chosen as a tumor volume benchmark for which response characteristics were determined.

The primary endpoints used to evaluate efficacy were: Tumor growth delay ("T-C"), the number of tumor-free survivors at the end of the study, and the Incidences of progressive disease, stable disease and regressing disease. The mean tumor growth for each group, shown as mean tumor burden in mm$^3$ for the 12 experimental groups is shown in FIG. 1. The median tumor growth for each group, shown as mean tumor burden in mm$^3$ for the 12 experimental groups is shown in FIG. 2.

Tumor Growth Delay (T-C) is the difference between the median times it takes the treated and control groups to reach the stated evaluation size. This is calculated from the median times to evaluation size for each animal in the group, not from interpolation of the median growth curve. Tumor growth delay results showing the statistically significant delays for this study are provided in table 1.

TABLE 1

Tumor Growth Delay

| Group | G1 | G2 | G3 | G4 | G5 | G6 | G7 | G8 | G9 | G10 | G11 | G12 |
|---|---|---|---|---|---|---|---|---|---|---|---|---|
| G1-Vehicle (Saline) | | | | | | | | | | | | |
| G2-GMI-1359 | NS | | | | | | | | | | | |
| G3-anti KLH; Rat IgG2b, LTF-2 | NS | NS | | | | | | | | | | |
| G4-anti-mPD-L1 | NS | NS | NS | | | | | | | | | |
| G5-GMI-1359 + anti KLH; Rat IgG2b, LTF-2 | NS | NS | NS | NS | | | | | | | | |
| G6-GMI-1359 + anti-mPD-L1 | NS | NS | NS | NS | NS | | | | | | | |
| G7-Vehicle (Saline) | NS | NS | NS | + | NS | + | | | | | | |
| G8-GMI-1359 | NS | NS | NS | NS | NS | NS | NS | | | | | |
| G9-anti KLH; Rat IgG2b, LTF-2 | NS | NS | NS | + | NS | + | NS | NS | | | | |
| G10-anti-mPD-L1 | NS | NS | + | + | NS | + | NS | NS | NS | | | |
| G11-GMI-1359 + anti KLH; Rat IgG2b, LTF-2 | NS | NS | NS | + | NS | + | NS | NS | NS | NS | | |
| G12-GMI-1359 + anti-mPD-L1 | NS | NS | + | + | NS | + | NS | NS | NS | NS | NS | |

+ = P < 0.05
NS = Nonsignificant

In this study, a therapeutic response was expected to require the activation of an immune response which takes approximately 1-2 weeks. At the time of first treatment, tumor burdens were not evident. For these reasons a Benchmark day (Day 9) was selected as the first day a response could theoretically have begun to occur. Growth and/or progression delay were calculated from the first day of dosing. Other parameters such as progression free survival and tumor doubling times were measured from the benchmark day.

An animal was coded as one with progressing disease if its tumor burden increased to ≥2 fold that on the benchmark day (Day 9).

The time from Day 9 to progression was used to estimate "progression-free survival." A mouse was declared to have stabilized disease if its tumor burden failed to progress (defined above) for at least 2 control group doubling times, and also failed to regress to less than 50% of the Day 9 burden.

Mice were coded as having regressing disease if their tumor burden decreased less than 50% of that at Day 9.

Tumor doubling times were calculated for all mice with measurable tumors starting on Day 9.

Assessment of Side Effects:

All animals were observed for clinical signs at least once daily. Animals were weighed on each day of treatment. Individual body weights were recorded 3 times weekly. Treatment-related weight loss in excess of 20% was considered unacceptably toxic. In this report, a dosage level is described as tolerated if treatment-related weight loss (during and two weeks after treatment) is <20% and mortality during this period in the absence of potentially lethal tumor burdens is ≤10%. FIG. 6 provides a graph of the percent mean body weight change for the 12 experimental groups. As indicated in FIG. 6 (and the Maximum Treatment Related Weight Loss column in FIG. 19 indicating that all subjects gained weight), the treatments were all well-tolerated and no weight loss was observed.

Upon death or euthanasia, all animals were necropsied to provide a general assessment of potential cause of death and perhaps target organs for toxicity. The presence or absence of metastases was also noted. Remarkable observations of clinical signs and necropsy findings were tabulated as well as individual and group toxicity findings.

Statistics:

The data were analyzed by the application of a one-way analysis of variance (ANOVA), with post-hoc analysis by the method of Shapiro-Wilk. In cases where the data did not pass testing for either normality or equal variance, a Kruskal-Wallis ANOVA by ranks was performed with post-hoc analysis by the method of Dunn's. The statistical comparisons were performed on the time to evaluation size (750 mm$^3$).

Flow Cytometry Methods:

For tumor dissociation, the tumor was weighed and <1 g tissue was processed according to Miltenyi Tumor Dissociation Protocol 2.2.1, Dissociation of soft tumors, before proceeding to the red blood cell lysis.

For spleen dissociation, the plunger on a 3 mL syringe was used to crush the spleen in 10 mL DPBS until organ was well broken up and the DPBS became cloudy with cells. The cell suspension was then filtered with a 70 μm strainer on a 50 mL tube and washed with 20 mL DPBS. The suspension was then centrifuged for 7 minutes at 300 rcf and the supernatant was discarded before proceeding the red blood cell lysis.

For the red blood cell lysis, each of the tumor and spleen samples were re-suspended in 3 mL ACK Lysis Buffer and then incubated for 5 minutes at room temperature. The suspension was diluted by adding 10 mL DPBS, and then the cells were collected via centrifugation for 5 minutes at 300 rcf. The cells were again re-suspended in 30 mL DPBS and counted. The suspension was centrifuged again, and the supernatant was discarded before proceeding to the Fc block.

For the Fc block, each of the tumor and spleen samples were re-suspended at 1E+06 cells per 100 μL in Flow Cytometry Staining buffer with 1 μL Fc block per 1E+06 cells. The suspensions were incubated for 5 minutes at room temperature, then centrifuged for 5 minutes at 300 rcf, and the supernatant was removed before proceeding to surface staining.

For the surface staining, the following antibody dilutions were prepared, 50 μL per reaction in Flow Cytometry Staining Buffer (except FoxP3):

T-Cells—Tumor: CD4 1:1000+CD8a 1:1000+5 μL CD197+5 μL CD62L

T-Cells—Spleen: CD4 1:2000+CD8a 1:2000+5 μL CD197+5 μL CD62L

CD11b & GR1—Tumor: CD11b 1:500+GR1 1:1000
CD11b & GR1—Spleen: CD11b 1:500+GR1 1:1000
PD-1—Tumor: 1:1000
PD-1—Spleen: 1:1000
PD-L1—Tumor: 1:250
PD-L1—Spleen: 1:500
CTLA-4—Tumor: 1:500
CTLA-4—Spleen: 1:500
CD8a & Ki67—Tumor: CD8a 1:1000+Ki67 1:1000

CD8a & Ki67—Spleen: CD8a 1:2000+Ki67 1:1000

CD4, CD25, & FoxP3—Tumor: CD4 1:1000+CD25 1:500; FoxP3: 1:500 in permeabilization buffer CD4, CD25, & FoxP3—Spleen: CD4 1:2000+CD25 1:500; 1. FoxP3: 1:500 in permeabilization buffer For surface staining, the tumor and spleen cells were re-suspended at 1E+06 cells per 50 µL. Each of the 50 µL cell suspensions containing 1E+06 cells was added to 50 µL antibodies diluted in staining buffer in round-bottom 96-well plate. The plate was incubated for 30 minutes in the dark at room temperature on the orbital shaker, setting 2.5. The samples were diluted by adding 200 µL Flow Cytometry Staining Buffer and then centrifuged for 5 minutes at 300 rcf. The supernatant was aspirated and the cells were washed wash by re-suspending in 250 µL Flow Cytometry Staining Buffer and spinning. If staining for intracellular markers, after washing, the sample was then prepared according to the intracellular staining procedure described below. The samples were then re-suspended in 250 µL Flow Cytometry Staining Buffer and were ready for Flow Cytometry Analysis.

When staining for intracellular markers, following the wash step, the cells were re-suspended in 200 µL FoxP3 Fixation/Permeabilization working solution and incubated for 30 minutes in the dark at room temperature. The samples were then centrifuged at 400 rcf for 5 minutes at room temperature, then the supernatant was discarded. 200 µL 1× permeabilization buffer was added to each well. The samples were centrifuged at 400 rcf for 5 minutes at room temperature, then the supernatant was discarded. 200 µL 1× permeabilization buffer was added to each well for a second time. The samples were again centrifuged at 400 rcf for 5 minutes at room temperature, then the supernatant was again discarded. The cells were then re-suspended in 50 µL permeabilization buffer and 50 µL 1× permeabilization buffer with anti-FoxP3 or Ki67 was added. The suspension was incubated for 60 minutes in the dark at 4° C. The samples were diluted by adding 200 µL 1× permeabilization buffer, and then centrifuged for 5 minutes at 400 rcf. The supernatant was removed, the cells were washed with 250 µL Flow Cytometry Staining Buffer per well, followed by centrifugation for 5 min at 400 rcf. The washing was repeated once (supernatant again removed, the cells washed with 250 µL Flow Cytometry Staining Buffer per well, followed by centrifugation for 5 min at 400 rcf). The cells were re-suspended in 250 µL Flow Cytometry Staining Buffer per well, and the samples are ready for Flow Cytometry Analysis.

For the flow cytometry analysis, once the samples were prepared, the 96-well plate is loaded into the Attune Autosampler. Several samples (from which no data were generated) were required to define the instrument settings—these include unlabeled cells for voltage optimization and gating, as well as fluorescence-minus-one controls to validate the gates. The workspace was customized, beginning with a side scatter (SSC) versus forward scatter (FSC) dot plot and adding relevant "daughter" plots to display fluorescence data. This initial plot was used to gate on live cells, live tumor cells, or live lymphocytes, and further analysis was performed on only the selected populations. Once the workspace was set up, the autosampler acquired data.

In order to generate a compensation matrix, AbC mouse/rat beads were used. These beads contain two components: capture beads which bind to the heavy chain of any antibody generated in their designated species and negative beads with no antibody binding capacity. The beads provide very strong positive and negative signals which can be used to calculate the emission spillover between channels from fluorophores being used.

To begin, the AbC capture beads and negative beads were re-suspended by vortexing prior to use. For each fluorophore-conjugated antibody used, a sample tube was prepared with 1 drop of the appropriate species-specific capture beads and 50 µL antibody at the determined working dilution. The solution in the sample tube was mixed well and incubated for 15 minutes are room temperature in the dark. 3 mL Flow Cytometry Staining Buffer was added to sample tubes to dilute antibody, and then centrifuged for 5 minutes at 200 rcf. The supernatant was removed and the bead pellet was re-suspended in 500 µL Flow Cytometry Staining Buffer. One drop of negative beads was added to each tube and mixed well. The samples were then analyzed by flow cytometry.

FIGS. 7-14 provide graphs of the results of the flow cytometry analysis for various markers tested in groups 7 through 12. The graphs also categorize each of the individuals in the groups as having progressive disease, stable disease, or as a tumor-free survivor. FIG. 7 graphs the percentage of $CD4^+/CCR7^+/CD62L^+$ cells in tumors; FIG. 8 graphs the percentage of $CD8^+/CCR7^+/CD62L^+$ cells in tumors; FIG. 9 graphs the percentage of $CD11b^+/GR1^+$ cells in tumors; FIG. 10 graphs the percentage of $CD4^+/CD25^+/FoxP3^+$ cells ($T_{reg}$ cells) in tumors; FIG. 11 graphs the percentage of $CD4^+/CCR7^+/CD62L^+$ cells in spleens; FIG. 12 graphs the percentage of $CD8^+/CCR7^+/CD62L^+$ cells in spleens; FIG. 13 graphs the percentage of $CD11b^+/GR1^+$ cells in spleens; and FIG. 14 graphs the percentage of $CD4^+/CD25^+/FoxP3^+$ cells ($T_{reg}$ cells) in spleens.

Experimental Glossary

Day 0—The day tumors are implanted into the animals (not to be confused with the first day of treatment which is always indicated relative to Day 0).

Evaluation size—The tumor burden ($mm^3$) selected for calculation of tumor growth delay. The Evaluation Size is selected from the exponential portion of the control tumor growth curve where the error of measurement tends to be minimal (usually between 500 and 1000 $mm^3$).

Progressive Disease (PD)—An animal was credited with progressive disease when within the time frame of the experiment there was a >2× increase in tumor size when compared to the benchmark day. FIG. 19, PD column, discloses the percentage of the subjects within each group presenting with progressive disease.

Stable Disease (SD)—An animal was credited with stable disease when within the time frame of the experiment there is a period of time during which the tumor never gets to >2× the size observed on the benchmark day or never gets to less than 50% of the size vs the benchmark day. FIG. 19, SD column, discloses the percentage of the subjects within each group presenting with stable disease.

Tumor-Free Survivors (TFS)—Any animal with no measurable evidence of disease on the last day of the experiment. This value is exclusive of CRs. FIG. 19, TFS column, discloses the percentage of the subjects within each group presenting as tumor free.

Rx Related Death—An animal is presumed to experience a treatment-related death if it is found dead or is euthanized in moribund condition within 2 weeks of the last treatment with a tumor burden less than half that of the smallest lethal tumor in the control group and shows no evidence of infection, mechanical dosing trauma, or other obvious causes of morbidity at necropsy. This is an individual toxicity parameter. As shown in FIG. 19, Rx Related Death column, all of the treatments were well tolerated as no individuals died or were euthanized as a result of any treatment.

Tumor Doubling Time—The growth rate of the tumor expressed as the volume doubling time (days). Calculated from a log-linear least squares regression of the exponential portion of the tumor growth curve. These values are used to compute tumor cell kill, fractional effect, and surviving fraction estimates. They are also used to assess the appropriateness of the biology of the tumor in this experiment against historical values.

Therapeutic Index—We define therapeutic index as simply the range of tolerated dosage levels that produce substantial anticancer activity. Substantial activity for this purpose is defined as a tumor growth delay that is ≥ the duration of treatment and that is also statistically different from the control at the P≤0.05 level.

Time to Evaluation Size—The time (days) it takes a tumor to reach the specified Evaluation Size. Calculated from a log-linear least squares best fit of tumor burden versus time for the exponential portion of the final (post-treatment) tumor growth curve. This value is calculated for every animal in the experiment. The group medians are then used to calculate the Tumor Growth Delay. This is an individual efficacy parameter.

Tumor Burden at Last Rx—The tumor burden on the last day of treatment. This value is calculated from a log-linear least squares best fit of tumor burden versus time for the exponential portion of the final (post-treatment) tumor growth curve. (Presented to facilitate T/C comparisons.)

Example 1

A study was undertaken to evaluate anti-tumor effects, and thus, potential cancer treatments of at least one T-cell checkpoint inhibitor in combination with at least one E-selectin inhibitor and/or at least one CXCR4 receptor inhibitor. In particular, this study investigated anti-tumor effects of administering at least one anti-mPD-L1 immune checkpoint inhibitor antibody and GMI-1359 as well as of administering GMI-1359 alone. In addition, a preliminary examination of potential changes in immune cell endpoints was undertaken.

All mice were distributed into treatment groups at the time of implant prior to a tumor being established. All animals weighed 216.6 g at the initiation of therapy. Mean group body weights for all animals at first treatment were well-matched (range 17.4-18.3 g). A tumor burden of 750 mm$^3$ was chosen for evaluation of efficacy by tumor growth delay.

Group 1, Vehicle (Saline), 0.2 mL/20_. QDx20: D3 Group 7. Vehicle (Saline), 0.2 mL/20 g, QDx12: D3

Between Days 21-30, all Group 1 control animals were euthanized via CO2 inhalation due to tumor burden exceeding >2000 mm$^3$. Necropsies were performed and the findings were: enlarged spleens (9/10), and white striated tissue located on the right ventricle (1/10). One mouse did not have remarkable necropsy findings.

The median time to evaluation size was 15.9 days from the start of dosing (Day 3) and the median post Day 9 tumor volume doubling time for Group 1 was 3.1 days. There were no spontaneous regressions in the control group and the take rate was 100%. All mice in the Control Group were identified with progressive disease. The median time to progression was on Day 11.6 and the progression free survival period was 2.6 days.

On Day 15 all Group 7 control animals were euthanized via CO2 inhalation 24 hours post dose for tumor and spleen collection. Necropsies were performed and the following findings were noted: enlarged spleens, (3/5 mice), enlarged uterine horn (1/5), white striated tissue located on the right ventricle (2/5). One mouse did not have any remarkable necropsy findings.

The median time to evaluation size was 12.6 days and the median post Day 9 tumor volume doubling time for Group 7 was 2.1 days. There were no spontaneous regressions in the control group and the take rate was 100%. All mice in the group were identified with progressive disease. These findings indicate that Groups 1 and 7 were closely matched for tumor growth characteristics.

The average percentage of T-cells detected in the Group 7 tumors via flow cytometry was 7.52% CD4$^+$ cells and 23.83% CD8$^+$ cells. There was an average of 4.14% myeloid-derived suppressor cells (MDSCs) and 3.37% regulatory T-cells ($T_{regs}$) in the tumors. The average percentages of cells expressing PD-1, PD-L1, and CTLA-4 were 28.07%, 29.57%, and 36.51%, respectively. Neither CD4$^+$/CCR7$^+$/CD62L$^+$ nor CD8$^+$/CCR7$^+$/CD62L$^-$ populations were detected in the tumor samples. The average percentage of CD4$^+$ T-cells expressing both CCR7 and CD62L was 28.75% while the average percentage of CD4$^+$ T-cells expressing CD62L but not CCR7 was 25.54%. Within the CD8$^+$ T-cell population, the average percentage of CCR7$^+$/CD62L$^+$ cells was 26.47% while the percentage of CD8$^+$ T-cells expressing CD62L but not CCR7 was 23.82%.

In the spleens of the Group 7 mice, an average of 12.62% of the cells were CD4$^+$ and 8.04% were CD8$^+$. The average percentage of MDSCs was 2.95% and $T_{reg}$ was 8.29%. The average percentages of cells expressing PD-1, PD-L1, and CTLA-4 were 4.17%, 82.74%, and 7.11%, respectively. The average percentage of CD4$^+$ T-cells expressing both CCR7 and CD62L was 3.69%, expressing CCR7 but not CD62L was 33.57%, and expressing CD62L but not CCR7 was 8.06%.

Within the CD8$^+$ T-cell population, the average percentage of CCR7$^+$/CD62L$^+$ cells was 2.10%, expressing CCR7 but not CD62L was 29.49%, and expressing CD62L but not CCR7 was 6.04%.

Group 2, GMI-1359, 40 mg/kg, QDx20; D3/Group 8, GMI-1359, 40 mg/kg, QDx12: D3

In Group 2, treatment with GMI-1359 was well tolerated, resulting in no treatment-related mortality. No weight loss was associated with treatment. Treated animals experienced a 16.8% mean weight gain during the treatment regimen. Between Days 18-49, all Group 2 animals were euthanized via CO2 inhalation due to tumor burden exceeding >2000 mm$^3$. Necropsies findings were similar to those in vehicle treated mice (Groups 1 and 7).

In Group 8, treatment with GMI-1359 was well tolerated, resulting in no treatment-related mortality. No weight loss was associated with treatment. Treated animals experienced a 7.0% mean weight gain during the treatment regimen. On Day 15, all Group 8 animals were euthanized via CO2 inhalation 24 hours post dose for tumor and spleen collection. Necropsies were unremarkable. These findings indicate that treatment with GMI-1359 was well tolerated and that Groups 2 and 8 were closely matched for tolerance to treatment.

Group 3, anti-KLH; Rat IgG2b, LTF-2, 10 mg/kg, (Q3Dx2: 3off)×2.5; D3/Group 9, anti-KLH; Rat IgG2b, LTF-2, 10 mg/kg, (Q3Dx2: 3off)×2; D3

In Group 3, treatment with anti-KLH; Rat IgG2b, LTF-2 was well tolerated, resulting in no treatment-related mortality. No weight loss was associated with treatment. Treated animals experienced a 9.7% mean weight gain during the treatment regimen. Between Days 18-37, all Group 3 animals were euthanized via CO2 inhalation due to tumor burden exceeding >2000 mm³. Necropsies were performed and the following findings were noted: enlarged spleens (10/10), and white striated tissue located on the right ventricle (1/10). One mouse had a non-weeping ulcerated tumor.

In Group 9, treatment with anti-KLH; Rat IgG2b, LTF-2 was also well tolerated, resulting in no treatment-related mortality. No weight loss was associated with treatment. Treated animals experienced a 9.3% mean weight gain during the treatment regimen. On Day 15, all Group 9 animals were euthanized via CO2 inhalation 24 hours post dose for tumor and spleen collection. Necropsies were unremarkable.

These findings indicate that treatment with anti-KLH; Rat IgG2b, LTF-2 was well tolerated and that Groups 3 and 9 were well matched for tolerance to treatment with anti-KLH; Rat IgG2b, LTF-2.

Group 4, anti-mPD-L1, 10F.9G2, 10 mg/kg, (Q3Dx2: 3off)x2.5; D3/Group 10, anti-mPD-L1, 10F, 9G2, 10 mg/kg, (Q3Dx2: 3off)x2; D3

In Group 4, treatment with anti-mPD-L1, 10F.9G2 was well tolerated, resulting in no treatment-related mortality. No weight loss was associated with treatment. Treated animals experienced a 10.1% mean weight gain during the treatment regimen. Between Days 23-37, Mice 1, 2, 3, 4, 5 and 9 were euthanized via CO2 inhalation due to tumor burden exceeding >2000 mm³. Necropsies were performed and the following findings were noted: enlarged spleens (6/10), enlarged uterine horn (3/10), and one mouse had a non-weeping ulcerated tumor.

Mice 6, 7, 8 and 10 were re-implanted subcutaneously (left, high axilla) on Day 44 post initial implant. On Day 81, Mice 6, 7, 8 and 10 were euthanized via CO2 inhalation per client request. Mice 8 and 10 enlarged uterine horns at necropsy. Necropsies of Mice 6 and 7 were unremarkable.

In Group 10, treatment with anti-mPD-L2, 10F.9G2 was also well tolerated, resulting in no treatment-related mortality. No weight loss was associated with treatment. Treated animals experienced a 1.6% mean weight gain during the treatment regimen. On Day 15, all Group 10 animals were euthanized via CO2 inhalation 24 hours post dose for tumor and spleen collection. Necropsies were performed and the following findings were noted: enlarged uterine horn (3/5); and 1/5 mice was noted as having white striated tissue located on the right ventricle. These findings indicate that treatment with anti-mPD-L2, 10F.9G2 was well tolerated and that Groups 4 and 10 were well matched with respect to tolerance of the treatment regimen.

Group 5, GMI-1359+anti-KLH; Rat IgG2b, LTF-2, 40+10 mg/kg, QDx20+(Q3Dx2: 3off)x2.5: D3/Group 11, GMI-1359+anti KLH: Rat IgG2b. LTF-2, 40+10 mg/kg, QDx12+(Q3Dx2: 3off)x2; D3

In Group 5, treatment with GMI-1359+anti KLH; Rat IgG2b, LTF-2 was well tolerated, resulting in no treatment-related mortality. No weight loss was associated with treatment. Treated animals experienced a 16.7% mean weight gain during the treatment regimen. Between Days 16-28, all Group 5 animals were euthanized via CO2 inhalation due to tumor burden exceeding >2000 mm³. Necropsies were performed and the following findings were noted: enlarged spleens (10/10); white striated tissue located on the right ventricle (1/10); enlarged uterine horn (3/10); and 2/10 mice were noted as having slightly discolored "black" intestines.

In Group 11, treatment with GMI-1359+anti KLH, Rat IgG2b, LTF-2 was also well tolerated, resulting in no treatment-related mortality. No weight loss was associated with treatment. Treated animals experienced a 3.5% mean weight gain during the treatment regimen. On Day 15, all Group 10 animals were euthanized via CO2 inhalation 24 hours post dose for tumor and spleen collection. Necropsies were performed and the following findings were noted: enlarged spleen (1/5); enlarged uterine horn (2/5); white striated tissue located on the right ventricle (1/5); and 2/5 mice were noted as having no remarkable findings.

These findings indicate that treatment with GMI-1359+anti KLH, Rat IgG2b, LTF-2 was well tolerated and that Groups 5 and 11 were well matched with respect to tolerance of the treatment regimen.

Group 6, GMI-1359+anti-mPD-L1, 10F.9G2, 40+10 mg/kg, QDx20+(Q3Dx2: 3off)x2.5; D3/Group 12, GMI-1359+anti-mPD-L1, 10F.9G2, 40+10 mg/kg, QDx12+(Q3Dx2: 3off)x2; D3

In Group 6, treatment with GMI-1359+anti-mPD-L1, 10F.9G2 was well tolerated, resulting in no treatment-related mortality. No weight loss was associated with treatment. Treated animals experienced a 9.5% mean weight gain during the treatment regimen. Between Days 18-37, Mice 1, 2, 3, 5, 7 and 10 were euthanized via CO2 inhalation due to tumor burden exceeding >2000 mm³. Necropsies were performed and the following findings were noted: enlarged spleens (6/10), alopecia on the nose/muzzle (2/10), non-weeping ulcerated tumors (2/10), and 4 mice without remarkable findings. Mice 4, 6, 8, and 9 were re-implanted subcutaneously (left, high axilla) on Day 44 post initial implant. On Day 81, Mice 4, 6, 8, and 9 were euthanized via CO2 inhalation per client request. Mice 4, 6, 8, and 9 had unremarkable necropsies.

In Group 12, treatment with GMI-1359+anti-mPD-L1, 10F.9G2 was well tolerated, resulting in no treatment-related mortality. No weight loss was associated with treatment. Treated animals experienced a 2.5% mean weight gain during the treatment regimen. On Day 15, all Group 10 animals were euthanized via CO2 inhalation 24 hours post dose for tumor and spleen collection. Necropsies were unremarkable.

The findings indicate that combination therapy with GMI-1359+anti-mPD-L1, 10F.9G2 is well tolerated and that Groups 6 and 12 were well matched in regard to tolerance of the treatment regimen.

Efficacy

Group 2, GMI-1359, 40 mg/kg, IP, QDx20; D3/Group 8, GMI-1359, 40 mg/kg, IP, QDx12; D3

In Group 2, the median time to evaluation size (750 mm³) was 18.4 days from the start of dosing resulting in a tumor growth delay of 2.5 days and the median post Day 9 tumor volume doubling time for Group 2 was 3.3 days, essentially identical to the control tumor doubling time. Treatment with GMI-1359 produced no regressions or tumor free survivors. All mice were identified with progressive disease (100%). Treatment with GMI-1359 produced no regressions or tumor free survivors. All mice were identified with progressive disease (100%). The median time to evaluation size was 14.3 days and the median post Day 9 tumor volume doubling time for Group 8 was 1.8 days. The median time to progression was on Day 14.5, and the progression free survival period was 5.5 days.

The average percentage of T-cells detected in the Group 8 tumors via flow cytometry was 7.02% $CD4^+$ cells and 15.61% $CD8^+$ cells. There was an average of 2.66% myeloid-derived suppressor cells (MDSCs) and 2.93% regulatory T-cells (T_{regs}) in the tumors. The average percentages of cells expressing PD-1, PD-L1, and CTLA-4 were 23.39%, 34.44%, and 42.80%, respectively. Neither CD4$^+$/CCR7$^+$/CD62L$^-$ nor CD8$^+$/CCR7$^+$/CD62L$^-$ populations were detected in the tumor samples. The average percentage of CD4$^+$ T-cells expressing both CCR7 and CD62L was 25.32% while the average percentage of cells expressing CD62L but not CCR7 was 31.43%. Within the CD8$^+$ T-cell population, the average percentage of CCR7$^+$/CD62L$^+$ cells was 25.84% while the percentage of CD8$^+$ T-cells expressing CD62L but not CCR7 was 25.65%.

In the spleens of the Group 8 mice, an average of 13.43% of the cells were CD4$^+$ and 8.77% were CD8$^+$. The average percentage of MDSCs was 3.70% and T_{regs} was 10.00%. The average percentages of cells expressing PD-1, PD-L1, and CTLA-4 were 5.53%, 81.50%, and 12.31%, respectively. The average percentage of CD4$^+$ T-cells expressing both CCR7 and CD62L was 2.05%, expressing CCR7 but not CD62L was 33.36%, and expressing CD62L but not CCR7 was 5.42%. Within the CD8$^+$ T-cell population, the average percentage of CCR7$^+$/CD62L$^+$ cells was 1.00%, expressing CCR7$^+$/CD62L$^-$ was 27.95%, and expressing CD62L but not CCR7 was 2.94%.

Group 3, anti-KLH; Rat IgG2b, LTF-2, 10 mg/kg, (Q3D×2; 3off)×2.5; D3/Group 9, anti-KLH; Rat IgG2b, LTF-2, 10 mg/kg, (Q3D×2; 3off)×2; D3

In Group 3, the median time to evaluation size (750 mm$^3$) was 19.1 days from the start of dosing resulting in a tumor growth delay of 3.2 days and the median post Day 9 tumor volume doubling time for Group 3 was 3.2 days. Treatment with anti KLH; Rat IgG2b, LTF-2 produced no regressions or tumor free survivors. All mice were identified with progressive disease (100%). The median time to progression was on Day 12.4 and the progression free survival period was 3.4 days. The results in Group 9 were similar. However, one mouse never developed a tumor. A no-take was distinguishable from a response to treatment.

The average percentage of T-cells detected in the Group 9 tumors via flow cytometry was 7.18% CD4$^+$ cells and 19.99% CD8$^+$ cells. There was an average of 3.14% myeloid-derived suppressor cells (MDSCs) and 6.81% regulatory T-cells (T_{regs}) in the tumors. The average percentages of cells expressing PD-1, PD-L1, and CTLA-4 were 26.57%, 28.63%, and 38.68%, respectively. Neither CD4$^+$/CCR7$^+$/CD62L$^-$ nor CD8$^+$/CCR7$^+$/CD62L$^-$ populations were detected in the tumor samples. The average percentage of CD4$^+$ T-cells expressing both CCR7 and CD62L was 28.09% while the average percentage of cells expressing CD62L but not CCR7 was 31.62%. Within the CD8$^+$ T-cell population, the average percentage of CCR7$^+$/CD62L$^+$ cells was 23.50% while the percentage of CD8$^+$ T-cells expressing CD62L but not CCR7 was 26.95%.

In the spleens of the Group 9 mice, an average of 15.00% of the cells were CD4$^+$ and 10.91% were CD8$^+$. The average percentage of MDSCs was 2.28% and T_{regs} was 10.88%. The average percentages of cells expressing PD-1, PD-L1, and CTLA-4 were 4.80%, 84.78%, and 8.46%, respectively. The average percentage of CD4$^+$ T-cells expressing both CCR7 and CD62L was 1.91%, expressing CCR7 but not CD62L was 37.23%, and expressing CD62L but not CCR7 was 3.52%. Within the CD8$^+$ T-cell population, the average percentage of CCR7$^+$/CD62L$^+$ cells was 0.77%, expressing CCR7 but not CD62L was 31.59%, and expressing CD62L but not CCR7 was 1.48%.

Group 4, anti-mPD-L1, 10F.9G2, 10 mg/kg, (Q3D×2; 3off)×2.5; D3/Group 10, anti-mPD-L1, 10F.9G2, 10 mg/kg, (Q3D×2; 3off)×2; D3

Treatment with anti-mPD-L1, 10F.9G2 was well-tolerated. The median time to evaluation size (750 mm$^3$) was >28 days from start of dosing resulting in a tumor growth delay of 11.7 days and the median post Day 9 tumor volume doubling time for Group 4 was 4.2 days. Treatment produced a 60% incidence of progressive disease (in Mice 1, 2, 3, 4, 5 and 9) and a 40% incidence of regressing disease (Mice 6, 7, 8 and 10) which all resulted in tumor-free survivors. These mice were later re-challenged and neither primary nor re-challenged implants had any regrowth. The median time to progression was on Day 12.8 and the progression free survival period was 3.8 days.

In Group 10, response status was assigned based on substantially increased tumor doubling time for responders. Euthanasia for sampling prevented an assessment of potential tumor regressions. Treatment with anti-mPD-L1, 10F.9G2 produced a 20% incidence of progressive disease and 80% stable disease. The median time to evaluation size was not determined because the sampling group came down for analysis. The median post Day 9 tumor volume doubling time for Group 10 was 8.1 days.

The average percentage of T-cells detected in the Group 10 tumors via flow cytometry was 7.42% CD4$^+$ cells and 15.52% CD8$^+$ cells. There was an average of 2.69% myeloid-derived suppressor cells (MDSCs) and 1.69% regulatory T-cells (T_{regs}) in the tumors. The average percentages of cells expressing PD-1, PD-L1, and CTLA-4 were 26.46%, 53.49%, and 43.76%, respectively. Neither CD4$^+$/CCR7$^+$/CD62L$^-$ nor CD8$^+$/CCR7$^+$/CD62L$^-$ populations were detected in the tumor samples. The average percentage of CD4$^+$ T-cells expressing both CCR7 and CD62L was 21.30% while the average percentage of cells expressing CD62L but not CCR7 was 34.21%. Within the CD8$^+$ T-cell population, the average percentage of CCR7$^+$/CD62L$^+$ cells was 21.98% while the percentage of CD8$^+$ T-cells expressing CD62L but not CCR7 was 26.26%.

In the spleens of the Group 10 mice, an average of 12.80% of the cells were CD4$^+$ and 6.16% were CD8$^+$. The average percentage of MDSCs was 1.62% and T_{regs} was 11.24%. The average percentages of cells expressing PD-1, PD-L1, and CTLA-4 were 6.42%, 37.32%, and 17.15%, respectively. The average percentage of CD4$^+$ T-cells expressing both CCR7 and CD62L was 13.00%, expressing CCR7 but not CD62L was 25.47%, and expressing CD62L but not CCR7 was 24.17%. Within the CD8$^+$ T-cell population, the average percentage of CCR7$^+$/CD62L$^+$ cells was 6.69%, expressing CCR7 but not CD62L was 27.90%, and expressing CD62L but not CCR7 was 19.21%.

Group 5, GMI-1359+anti KLH; Rat IgG2b, LTF-2, 40+10 mg/kg, QD×20+(Q3D×2; 3off)×2.5; D3/Group 11, GMI-1359+anti KLH; Rat IgG2b, LTF-2, 40+10 mg/kg, QD×12+(Q3D×2; 3off)×2; D3

In Group 5, treatment with GMI-1359+anti KLH; Rat IgG2b, LTF-2 was well-tolerated. The median time to evaluation size (750 mm$^3$) was 15.8 days from the start of dosing resulting in a tumor growth delay of −0.1 days and the median post Day 9 tumor volume doubling time for Group 5 was 2.8 days. Treatment with GMI-1359+anti KLH; Rat IgG2b, LTF-2 produced no regressions or tumor free survivors. All mice were identified with progressive disease (100%). The median time to progression was on Day 11.2 and the progression free survival period was 2.2 days.

Findings in Group 11 were similar. There were no regressions or tumor free survivors. All mice were identified with progressive disease (100%). The median time to evaluation size was not determined because the sampling group came down for analysis. The median post Day 9 tumor volume doubling time for Group 11 was 2.2 days.

The average percentage of T-cells detected in the Group 11 tumors via flow cytometry was 5.25% CD4$^+$ cells and 8.22% CD8$^+$ cells. There was an average of 3.29% myeloid-derived suppressor cells (MDSCs) and 1.79% regulatory T-cells (T$_{regs}$) in the tumors. The average percentages of cells expressing PD-1, PD-L1, and CTLA-4 were 25.85%, 55.52%, and 53.54%, respectively. Neither CD4$^+$/CCR7$^+$/CD62L$^-$ nor CD8$^+$/CCR7$^+$/CD62L$^-$ populations were detected in the tumor samples. The average percentage of CD4$^+$ T-cells expressing both CCR7 and CD62L was 24.14% while the average percentage of cells expressing CD62L but not CCR7 was 31.16%. Within the CD8$^+$ T-cell population, the average percentage of CCR7$^+$/CD62L$^+$ cells was 17.51% while the percentage of CD8$^+$ T-cells expressing CD62L but not CCR7 was 23.27%.

In the spleens of the Group 11 mice, an average of 13.33% of the cells were CD4$^+$ and 9.06% were CD8$^+$. The average percentage of MDSCs was 3.09% and T$_{regs}$ was 11.14%. The average percentages of cells expressing PD-1, PD-L1, and CTLA-4 were 8.18%, 84.00%, and 18.44%, respectively. The average percentage of CD4$^+$ T-cells expressing both CCR7 and CD62L was 11.19%, expressing CCR7 but not CD62L was 31.45%, and expressing CD62L but not CCR7 was 17.33%. Within the CD8$^+$ T-cell population, the average percentage of CCR7$^+$/CD62L$^+$ cells was 5.68%, expressing CCR7 but not CD62L was 35.85%, and expressing CD62L but not CCR7 was 11.18%.

Groups 6 and 12, GMI-1359+anti-mPD-L1, 10F.9G2, 40+10 mg/kg

In Group 6, the median time to evaluation size (750 mm$^3$) was >29 days from the start of dosing resulting in a tumor growth delay of 13.5 days and the median post Day 9 tumor volume doubling time for Group 6 was 5.9 days. Treatment with GMI-1359+anti-mPD-L1, 10F.9G2 produced a 60% incidence of progressive disease, and a 30% incidence of regressing disease. Mice 4, 6, 8 and 9 were identified as tumor free survivors. Mouse 9 was unable to be identified as PD, SD, or RD because a tumor never became present and could be considered as a complete responder or in a rare incidence a no-take. The incidence of no-takes in control groups was 2% across 7 previous studies.

Response characteristics in Group 12 were similar. The median time to evaluation size was not determined because the sampling group came down for analysis. The median post Day 9 tumor volume doubling time for Group 12 was 3.7 days. The median time to progression was on Day 12.6 and the progression free survival period was 3.6 days.

The average percentage of T-cells detected in the Group 12 tumors via flow cytometry was 8.25% CD4$^+$ cells and 16.98% CD8$^+$ cells. There was an average of 4.38% myeloid-derived suppressor cells (MDSCs) and 0.91% regulatory T-cells (T$_{regs}$) in the tumors. The average percentages of cells expressing PD-1, PD-L1, and CTLA-4 were 23.76%, 50.24%, and 45.71%, respectively. Neither CD4$^+$/CCR7$^+$/CD62L$^-$ nor CD8$^+$/CCR7$^+$/CD62L$^-$ populations were detected in the tumor samples. The average percentage of CD4$^+$ T-cells expressing both CCR7 and CD62L was 21.70% while the average percentage of cells expressing CD62L but not CCR7 was 25.84%. Within the CD8$^+$ T-cell population, the average percentage of CCR7$^+$/CD62L cells was 20.24% while the percentage of CD8$^+$ T-cells expressing CD62L but not CCR7 was 23.32%.

In the spleens of the Group 12 mice, an average of 12.33% of the cells were CD4$^+$ and 8.01% were CD8$^+$. The average percentage of MDSCs was 2.22% and T$_{regs}$ was 11.66%. The average percentages of cells expressing PD-1, PD-L1, and CTLA-4 were 9.23%, 47.91%, and 17.93%, respectively. The average percentage of CD4$^+$ T-cells expressing both CCR7 and CD62L was 7.15%, expressing CCR7 but not CD62L was 32.54%, and expressing CD62L but not CCR7 was 12.52%. Within the CD8$^+$ T-cell population, the average percentage of CCR7$^+$/CD62L$^+$ cells was 2.77%, expressing CCR7 but not CD62L was 35.65%, and expressing CD62L but not CCR7 was 6.36%.

FIG. 19, Tumor Growth Delay column, provides the results, in days, that each treatment delayed tumor growth. Treatment with GMI-1359 alone did not produce a statistically significant (p>0.05) anti-tumor effect and all animals were identified with progressive disease with a minimal tumor growth delay of 2.5 days. Treatment with anti-mPD-L1 as a single agent produced a statistically significant (p<0.05) anti-tumor effect where 30% of the mice were identified as having regressing disease and 40% as tumor free survivors with a median tumor growth delay of 11.7 days.

Treatment with GMI-1359 in combination with anti-mPD-L1 also produced a statistically significant (p<0.05) anti-tumor effect vs. all groups where 30% of the mice were identified as having regressing disease and 40% as tumor free survivors with a median tumor growth delay of 13.5 days.

In Group 4 (anti-mPD-L1 alone) and Group 6 (GMI-1359+anti-mPD-L1) four mice each were re-implanted subcutaneously (left, high axilla) on Day 44. All re-challenged mice were held out to Day 81 when they were euthanized per client request as no re-growth occurred. That is, as indicated in FIG. 20, mice that achieved a complete response, even those with a quicker complete response due to the treatment combining both GMI-1359 and anti-mPD-L1, rejected a subsequent challenge to CT-26.

Within the efficacy arms, there was a difference between the anti-mPD-L1 monotherapy arm and the GMI-1359+anti-mPD-L1 combination arm. While the overall response rate was the same, the mice in the combination group demonstrated an earlier response. Furthermore, mice in group 1 (saline control) and group 2 (with single agent GMI-1359) were all identified with progressive disease (see FIG. 19). In contrast, as shown in FIGS. 19 and 20, treatment with anti-mPD-L1 alone (group 4) or in combination with GMI-1359 (group 6) produced a 40% complete response (CR), or tumor free survivor (TFS), rate.

The median time to CR was shorter when anti-mPD-L1 was combined with GMI-1359 (group 6) compared to anti-mPD-L1 alone (group 4). As shown in FIG. 20, the median time to CR for treatment group 6, treated with anti-mPD-L1 was combined with GMI-1359, versus 23 days for group 4, treated with anti-mPD-L1 alone (p<0.0471). Evaluation of tumor infiltrating cells showed that combination therapy with GMI-1359 and anti-mPD-L1 antibody (group 12) reduced the percentage of T$_{reg}$ compared to treatment with saline (group 7), GMI-1359 (group 8), or the anti-mPD-L1 antibody (group 10) as single treatments (0.9% vs. 3.3%, 2.9% and 1.9%, respectively (see FIG. 10)). No other T cell subsets were affected (see, e.g., FIGS. 7 and 8 (other T cells) as compared to FIG. 10 (T$_{reg}$ cells)). In spleens, the median percentage of T$_{reg}$ were unaffected by any of the treatments (see, e.g., FIG. 14) and suggest that the reduction in intratumoral T$_{reg}$ by combined treatment with anti-PD-L1 and the heterobifunctional E-selectin and CXCR4 receptor inhibitor GMI-1359 was an attenuated response to maintenance and homing signals in the tumor microenvironment.

Within the CD4- and CD8-positive T cell population's expression of CCR7 and CD6L, two lymph node homing molecules were investigated. Co-expression of CCR7 and CD62L is found on central memory T cells (TCM). The tumor lymphocytes were found to differ from the splenic lymphocytes in that, within the tumor, no CD4$^+$/CCR7$^+$/CD62L$^-$ or CD8$^+$/CCR7$^+$/CD62L$^-$ populations could be found whereas, within the spleen, these populations were quite abundant.

Furthermore, the combination of GMI-1359 and anti-mPD-L1 treatments resulted in the lowest levels of T regulatory ($T_{reg}$) cells and the least amount of intra-group variability in the data.

In both spleens and tumors, the CTLA-4$^+$ population increased following treatment with anti-mPDL1 antibody. TIL CD4$^+$/CCR7$^+$/CD62L$^+$ appear to decrease with anti-mPD-L1 or GMI-1359 and anti-mPD-L1 treatments. TIL PD-L1 levels increase with anti-mPD-L1 alone, GMI-1359+isotype control and GMI-1359+anti-mPD-L1 treatments as compared to vehicle, GMI-1359 alone, or isotype control alone, respectively. FIG. 7 provides a graph of the percentage of CD4$^+$/CCR7$^+$/CD62L$^+$ in tumors for the individuals in experimental groups 7-12, and FIG. 11 provides a graph of the percentage of CD4$^+$/CCR7$^+$/CD62L$^+$ in the spleens of the individuals in experimental groups 7-12.

In the tumors, the average percentage of $T_{reg}$ cells remained the same when the mice were treated with the anti-mPD-L1 antibody (see, e.g., exemplary scatter plot for Group 10, FIG. 15A) or the GMI-1359 plus the isotype control antibody (see, e.g., exemplary scatter plot for Group 11, FIG. 15B). However, when the mice were treated with a combination of GMI-1359 and anti-mPD-L1 antibody (see, e.g., exemplary scatter plot for Group 12, FIG. 15C), the average percentage of $T_{reg}$ cells decreased.

More differences in markers between treatment groups were observed in the spleens compared to the tumors. Treatment with the anti-mPD-L1 antibody (Group 10), GMI-1359+isotype control antibody (Group 11), or the combination of GMI-1359 and the anti-mPD-L1 antibody (Group 12) significantly increased the percentages of CD4$^+$/CCR7$^+$/CD62L$^+$ cells compared to treatment with the vehicle (Group 1), GMI-1359 (Group 2), or the isotype control antibody (Group 3), respectively.

As noted above, FIG. 16A is a representative scatter plot showing the CD4$^+$/CCR7$^+$/CD62L$^+$ cells in spleens of an individual (mouse 4, group 8) treated with GMI-1359. FIG. 16B is a representative scatter plot showing the CD4$^+$/CCR7$^+$/CD62L$^+$ cells in spleens of an individual (mouse 1, group 12) treated with GMI-1359 and anti-PD-L1 antibody treatment. These graphs indicate that GMI-1359 in combination with the isotype control antibody affected the percentage of CD4$^+$/CCR7$^+$/CD62L$^+$ cells while GMI-1359 as a single agent did not.

Differences between groups in the percentages of cells that were CD8$^+$/CCR7$^+$/CD62L$^+$ were also detected in the spleens. FIG. 12 provides a graph of the percentage of CD8$^+$/CCR7$^+$/CD62L$^+$ cells in the spleens in experimental groups 7 through 12. When the mice were treated with the anti-mPD-L1 antibody (Group 10) or GMI-1359 together with the isotype control antibody (Group 11) the average percentage of CD8$^+$/CCR7$^+$/CD62L$^+$ cells increased compared to the vehicle control (Group 7). FIG. 17A shows a representative scatter plot of data from Mouse 4 in Group 7, and FIG. 17B shows a representative scatter plot of data from Mouse 3 in Group 10. When the mice were grouped according to the state of the disease and the percentages were dot-plotted in columns, the mice with stable disease in Group 12 had statistically significantly lower percentages of MDSCs than the mice with progressive disease (FIG. 13, providing a graph of the percentage of CD11b$^+$/GR1$^+$ (MDSCs) in Spleens in groups 7-12). Representative scatter plots showing these differences are shown in FIGS. 18A-C. Mouse 3 from Group 9 (FIG. 18A) represents all of those from Group 9, Mouse 3 from Group 12 (FIG. 18B) represents those mice from Group 12 with stable disease, and Mouse 4 from Group 12 (FIG. 18C) represents those mice from Group 12 with progressive disease.

Example 2

FIG. 21 relates to an experiment carried out to determine the competitive binding activity (IC50) of GMI-1359 against E-selectin and CXCR4. GMI-1359 was assessed for inhibition of sialyl Le$^x$ binding to immobilized E-selectin and α-CXCR4 antibody binding to Raji cells.

The inhibition assay to screen GMI-1359 as an antagonist of E-selectin was a competitive binding assay, which allowed the determination of IC$_{50}$ values. Human E-selectin/Ig chimera was immobilized by incubation at 37° C. for 2 hour in 96-well microtiter plates. To reduce nonspecific binding, BSA was added to each well and incubated at room temperature for 2 hours. After incubation with E-selectin/Ig chimera, the plate was washed and serial dilutions of the test compounds were added to the wells in the presence of conjugates of biotinylated, sLe$^a$-polyacrylamide with streptavidin/horseradish peroxidase and incubated for 2 hours at room temperature. To determine the amount of sLe$^a$ bound to immobilized E-selectin after washing, the peroxidase substrate, 3,3',5,5' tetramethylbenzidin (TMB) was added. After 3 minutes, the enzyme reaction was stopped by the addition of H$_3$PO$_4$, and the absorbance of light at a wavelength of 450 nm was determined. The absorbance of light readings were plotted as a function of increasing concentration of GMI-1359 using GraphPad Prism software, and the concentration of GMI-1359 compound required to inhibit binding by 50% was determined and reported as the IC$_{50}$ value for GMI-1359.

The inhibition assay to screen GMI-1359 as an antagonist of CXCR4 was a flow based competitive binding assay, which allowed the determination of IC$_5$ values. Raji cells (ATCC number TIB-152) were washed twice with Hanks Balanced Saline Solution (HBSS) containing 0.05% bovine serum albumin (BSA). After the second wash, the cells were resuspended to about 2.5×10$^6$ cells per mL and 80 µl of cells (approximately 2×10$^5$ cells) were added to BD 2063 tubes. Next, 10 µl of either GMI-1359 or HBSS/BSA (as a negative control) were added to the cells and the tube was placed at room temperature for 10 minutes. Then, 10 µl of a phycoerythrin-conjugated anti-CXCR4 antibody (R&D Systems, FAB170P) or as a negative control, 10 µl of an isotype control antibody (R&D Systems, IC003P) was added to the cells with HBSS/BSA. The antibodies were allowed to bind to the cells for 1 hour at 4° C. Next, 2 mL of cold HBSS/BSA were added to all the tubes, and the cells were pelleted by centrifugation at 250×g for 10 minutes. The supernatants were discarded and the cell pellets were resuspended in 1 mL of HBSS/BSA. The cells were pelleted again as before, suspended in 150 µl of HBSS/BSA and fixed by the addition of 150 µl of 2% formaldehyde. Binding of the anti-CXCR4-PE antibody to the cells was assessed by flow cytometry, and the median fluorescent intensity was determined. The median fluorescent intensities were plotted as a function of increasing concentration of GMI-1359 using GraphPad Prism software, and an IC50 (defined as the concentration of GMI-1359 resulting in a 50% inhibition of phycoerythrin-conjugated anti-CXCR4 antibody) was determined. As shown in FIG. 21, the results showed that the small molecule glycomimetic, GMI-1359, inhibits ligand binding to both E-selectin and CXCR4.

Example 3

FIG. 22 relates to an experiment carried out to determine percentages of CD4+, CD8+, and Regulatory T cells (CD4+, FoxP3+, and CD25+) in spleen and tumor tissue samples, in vivo, on study day 15, from each treatment group. Details of the experimental treatments for each of the groups are provided above with respect to Example 1.

Twenty-four hours following the final dose of GMI-1359, five mice from each treatment group were euthanized and spleens and tumors were processed for flow cytometry. Tumors were dissociated according to Miltenyi Dissociation Protocol for soft tumors. Single cell suspensions from spleen were obtained by maceration.

The following cell determinants were assessed using fluorescent conjugated reagents for flow cytometry: rat anti-CD4 FITC conjugate, clone GK1.5, rat anti-CD8a APC-AlexaFluor 750 conjugate, rat anti-CD11b PE conjugate, clone M1/70.15, rat anti-CD25 PE conjugate, clone PC61 5.3, mouse anti-FoxP3 APC conjugate, clone 3G3, rat anti-GR1 (LY6C/G) APC conjugate, clone 1A8, rat anti-CD62L PE conjugate, clone MEL 12-H2.100, hamster anti-CD152 (CTLA-4) PE conjugate, clone UC10-4F10-11, rat anti-CD279 (PD-1) FITC conjugate, clone RMPI-30, and rat anti-CD274 (PD-L1, B7-H1) APC conjugate, clone 10F.9G2.

Once the samples were prepared, a 96-well plate was loaded into the Attune Autosampler. Several samples (from which no data were generated) were required to define the instrument settings—these include unlabeled cells for voltage optimization and gating, as well as fluorescence-minus-one controls to validate the gates. The workspace was customized, beginning with a side scatter (SSC) versus forward scatter (FSC). This initial plot was used to gate on live cells, live tumor cells, or live lymphocytes, and further analysis was performed on only the selected cell determinants. Data was acquired from either 250,000 events or 180 µL, whichever threshold was reached first.

FIG. 22 shows the results for percentage of total CD4+ and CD8+ lymphocytes and regulatory T cells.

Example 4

FIG. 23 relates to an experiment carried out to determine the ratio of CD8/regulatory T cells in spleen and tumor tissue samples, in vivo, on day 15. Details of the experimental treatments for each of the groups are provided above with respect to Example 1.

Twenty-four hours following the final dose of GMI-1359, five mice from each treatment group were euthanized and spleens and tumors were processed for flow cytometry. Tumors were dissociated according to Miltenyi Dissociation Protocol for soft tumors. Single cell suspensions from spleen were obtained by maceration.

The following cell determinants were assessed using fluorescent conjugated reagents for flow cytometry: rat anti-CD4 FITC conjugate, clone GK1.5, rat anti-CD8a APC-AlexaFluor 750 conjugate, rat anti-CD25 PE conjugate, clone PC61 5.3, and mouse anti-FoxP3 APC conjugate, clone 3G3.

Once the samples were prepared, a 96-well plate was loaded into the Attune Autosampler. Several samples (from which no data were generated) were required to define the instrument settings—these include unlabeled cells for voltage optimization and gating, as well as fluorescence-minus-one controls to validate the gates. The workspace was customized, beginning with a side scatter (SSC) versus forward scatter (FSC). This initial plot was used to gate on live cells, live tumor cells, or live lymphocytes, and further analysis was performed on only the selected cell determinants. Data was acquired from either 250,000 events or 180 µL, whichever threshold was reached first.

The results showed that combination therapy with GMI-1359 and anti-PD-L1 antibody reduced the percentage of intratumoral $T_{reg}$ compared to treatment with saline, GMI-1359, or the anti-mPD-L1 antibody as single treatments (0.9% vs. 3.3%, 2.9%, and 1.9%, respectively). No other T cell subsets were affected. As shown in FIG. 23, reduction in intratumoral $T_{reg}$ cells resulted in a more favorable increase in the ratio of total CD8 T cells to $T_{reg}$ cells. In spleens, the median percentage of $T_{reg}$ cells were unaffected by any of the treatments, which suggests that the reduction in intratumoral $T_{reg}$ cells by combined treatment with anti-PD-L1 and GMI-1359 was an attenuated response to maintenance and homing signals in the tumor microenvironment.

Example 5

FIGS. 24A and 24B relate to an experiment carried out to compare the mean tumor burden and the responsiveness to treatments in each group. Details of the experimental treatments for each of the groups are provided above with respect to Example 1.

Tumor volumes were estimated from caliper measurements recorded three times weekly beginning at the start of treatment. Tumor burden ($mm^3$) was calculated by the formula for the volume of a prolate ellipsoid assuming unit density as: Tumor burden $(mm^3)=(L \times W^2)/2$, where L and W are the respective orthogonal tumor length and width measurements (mm). Animals with tumors in excess of 2000 $mm^3$ were euthanized.

FIG. 24A shows the primary endpoints used to evaluate efficacy: tumor growth delay; the number of tumor-free survivors at the end of the study; the incidences of progressive disease, stable disease, and regressing disease; and the response. Additionally, FIG. 24B shows the number of days post tumor implant on the x-axis and the mean tumor burden ($mm^3$) in each treatment group on the y-axis.

As shown in FIGS. 24A and 24B, all treatments of tumor-bearing mice were well tolerated, resulting in no treatment-related mortality. Likewise, as shown in FIG. 24A, treatment with GMI-1359 in combination with anti-PD-L1 or anti-PD-L1 alone was associated with a tumor-growth delay of 13.5 and 11.7 days, respectively, and a 40% complete response rate.

The various embodiments described above can be combined to provide further embodiments. All U.S. patents, U.S. patent application publications, U.S. patent applications, non-U.S. patents, non-U.S. patent applications, and non-patent publications referred to in this specification and/or listed in the Application Data Sheet are incorporated herein by reference, in their entirety. Aspects of the embodiments can be modified, if necessary, to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

ARTICLES

Callahan M K et al. Anti-CTLA-4 Antibody Therapy: Immune Monitoring During Clinical Development of a Novel Immunotherapy. Semin Oncol. October 2010; 37(5):473-484.

Postow M A, Callahan M K, Wolchok J D. Immune Checkpoint Blockade in Cancer Therapy. J. Clin. Oncol. January 2015; Epub.

Dunn G P, Old L J, & Schreiber R D. The Immunobiology of Cancer Immunosurveillance and Immunoediting. Immunity. August 2004; 21:137-148.

Naidoo J, Page D B, & Wolchok J D. Immune modulation for cancer therapy. British Journal of Cancer. September 2014; 111:2214-2219.

Kim R, Emi M, & Tanabe K. Cancer immunoediting from immune surveillance to immune escape. Immunology. May 2007; 121(1):1-14.

Schabel F, Griswold D, Laster W, Corbett T, Lloyd H. Quantitative evaluation of anticancer agent activity in experimental animals. Pharmac. Ther. A.

(1) 411-435, 1977.

Corbett, T, Griswold D, Roberts B, Peckham J, Schabel F Evaluation of single agents and combinations of chemotherapeutic agents in mouse colon carcinomas. Cancer 1977; 40(5); 2660-2690.

Schabel F, Griswold D, Corbett T, Laster R, Mayo J, Lloyd H. Testing therapeutic hypotheses in mice and man: Observations on the therapeutic activity against advanced solid tumors of mice treated with anticancer drugs that have demonstrated or potential clinical utility for treatment of advanced solid tumors of man. Methods in Cancer Research (17) 3-51, 1979.

Plowman J, Dykes D, Hollingshead M, Simpson-Herren L, and Alley M. Human tumor xenograft models in NCI drug development. In: Anticancer drug development guide: preclinical screening, clinical trials, and approval. Teicher (ed) Humana Press Inc. 1993.

Corbett T, Valeriote F, LoRusso P, Polin L, Panchapor C. Pugh S. White K, Knight J, Demchik L, Jones J, Jones L, Lowichik N, Biernat L, Foster B, Wozniak A, Lisow L, Valdivieso M, Baker L, Leopold W, Sebolt J, Bissery M, Mattes K, Dzubow J, Rake J, Perni R, Wentland M, Coughlin S, Shaw J M, Liversidge G, Liversidge E, Bruno J, Sarpotdar P, Moore R, Patterson G. Tumor models and the discovery and secondary evaluation of solid tumor active agents. Int J Pharmacognosy 1995; 33(supplement): 102-122.

Corbett T, Roberts B J, Lawson A J, Leopold W R, et al. Transplantable Syngeneic Rodent Tumors: Solid Tumors of Mice. In: Tumor Models in Cancer Research (BA Teicher 2nd ed). Humana Press, New York, N.Y. pp. 43-78, 2011.

R Development Core Team. R: A Language and Environment for Statistical Computing. 2005, R Foundation for Statistical Computing: Vienna, Austria. R, D.C.T., R: A Language and Environment for Statistical Computing. 2005, R Foundation for Statistical Computing: Vienna, Austria.

What is claimed is:

1. A method for treating a cancer chosen from multiple myeloma, acute lymphocytic leukemia, acute myeloid leukemia, colorectal cancer, and prostate cancer comprising administering to a subject in need thereof:
   (1) an effective amount of pembrolizumab; and
   (2) an effective amount of at least one heterobifunctional inhibitor chosen from compounds of Formula (II):

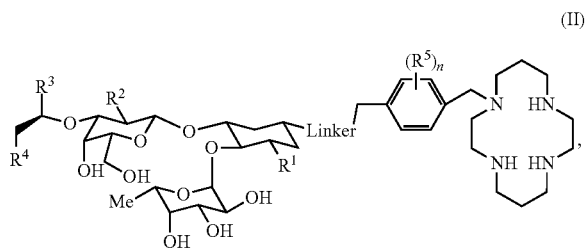

isomers of compounds of Formula (II), tautomers of compounds of Formula (II), and pharmaceutically acceptable salts of any of the foregoing, wherein:

$R^1$ is chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups;

$R^2$ is chosen from —OH, —NH$_2$, —OC(=O)Y$^1$, —NHC(=O)Y$^1$, and —NHC(=O)NHY$^1$ groups, wherein Y$^1$ is chosen from $C_{1-8}$ alkyl, $C_{2-8}$ alkenyl, $C_{2-8}$ alkynyl, $C_{1-8}$ haloalkyl, $C_{2-8}$ haloalkenyl, $C_{2-8}$ haloalkynyl, $C_{6-18}$ aryl, and $C_{1-13}$ heteroaryl groups;

$R^3$ is chosen from —CN, —CH$_2$CN, and —C(=O)Y$^2$ groups, wherein Y$^2$ is chosen from $C_{1-8}$ alkyl, $C_{2-8}$ alkenyl, $C_{2-8}$ alkynyl, —OZ$^1$, —NHOH, —NHOCH$_3$, —NHCN, and —NZ$^1$Z$^2$ groups, wherein Z$^1$ and Z$^2$, which may be identical or different, are independently chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, wherein Z$^1$ and Z$^2$ may together form a ring;

$R^4$ is chosen from $C_{3-8}$ cycloalkyl groups;

$R^5$ is independently chosen from H, halogen, $C_{1-8}$ alkyl $C_{2-8}$ alkenyl, $C_{2-8}$ alkynyl, $C_{1-8}$ haloalkyl, $C_{2-8}$ haloalkenyl, and $C_{2-8}$ haloalkynyl groups;

n is chosen from integers ranging from 1 to 4; and

Linker is chosen from linker groups.

2. The method of claim 1, wherein at least one of (1) pembrolizumab and (2) the at least one heterobifunctional inhibitor is in the form of at least one pharmaceutical composition.

3. The method of claim 1, wherein pembrolizumab is in the form of a first pharmaceutical composition and the at least one heterobifunctional inhibitor is in the form of a second pharmaceutical composition.

4. The method of claim 2, wherein said at least one pharmaceutical composition further comprises at least one pharmaceutically acceptable ingredient.

5. The method of claim 1, wherein the at least one heterobifunctional inhibitor is chosen from compounds of Formula (IIa):

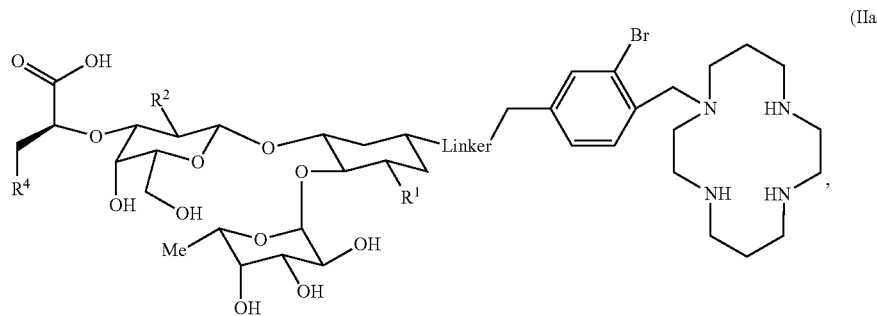

(IIa)

isomers of compounds of Formula (IIa), tautomers of compounds of Formula (IIa), and pharmaceutically acceptable salts of any of the foregoing.

6. The method of claim 1, wherein the at least one heterobifunctional inhibitor is GMI-1359.

7. The method of claim 1, wherein the subject has received or will receive chemotherapy and/or radiotherapy.

8. The method of claim 7, wherein the chemotherapy comprises administering an effective amount of bortezomib and/or gemcitabine.

9. The method of claim 1, wherein Linker is chosen from

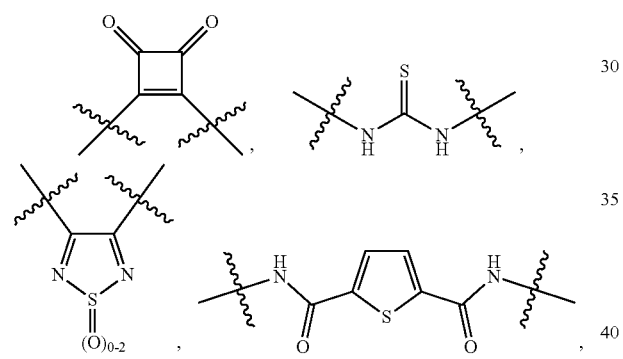

-continued

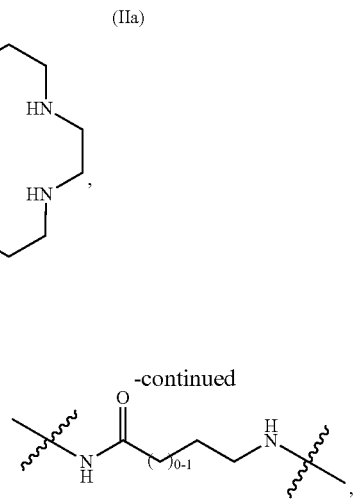

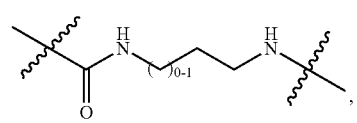

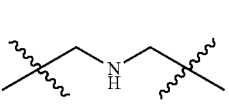 and .

10. The method of claim 1, wherein the at least one heterobifunctional inhibitor is chosen from:

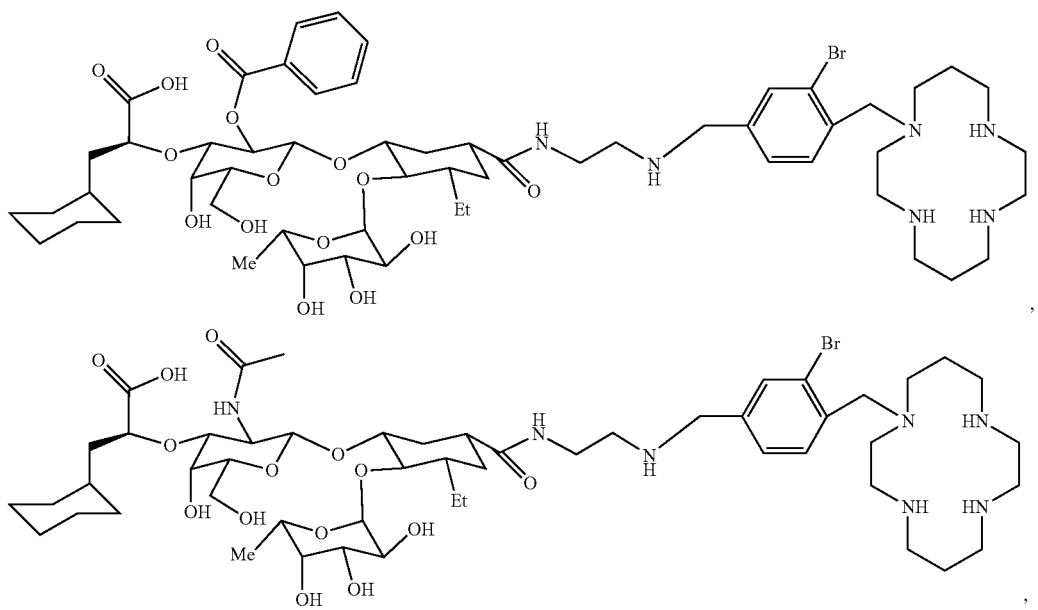

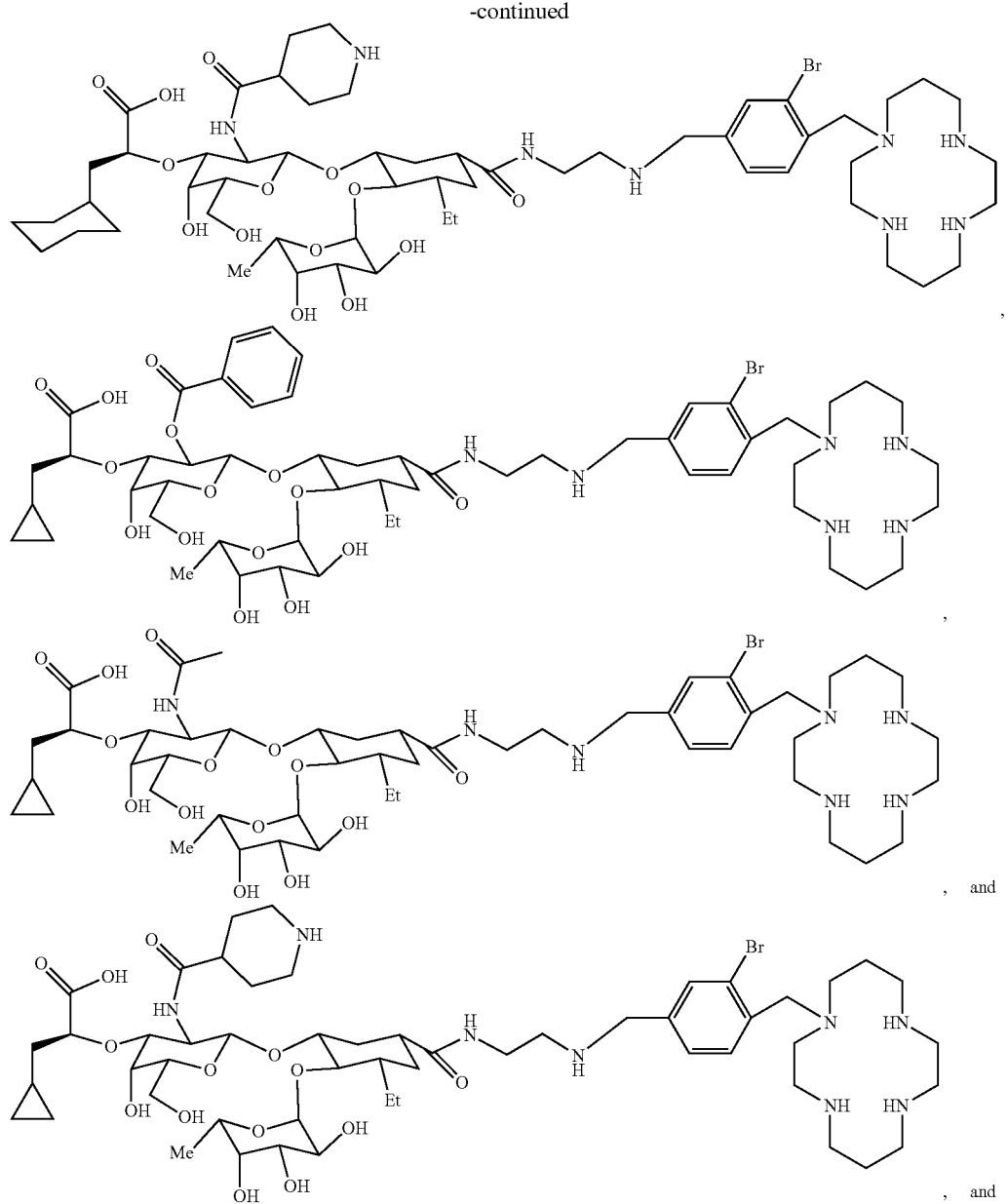
pharmaceutically acceptable salts of any of the foregoing.
11. The method of claim 1, wherein the at least one heterobifunctional inhibitor is chosen from:
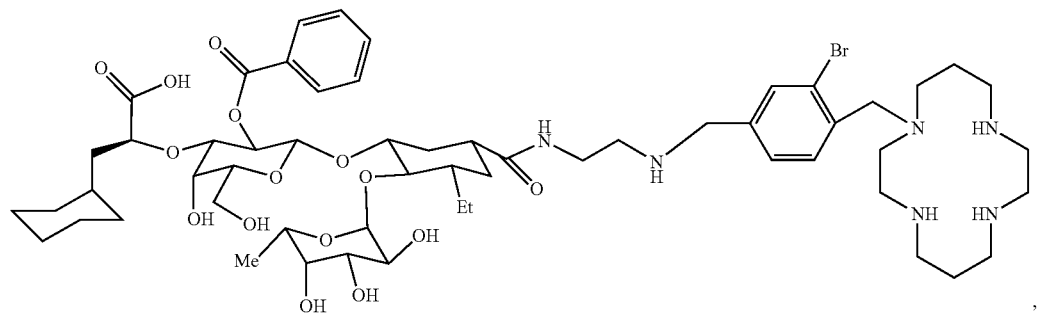

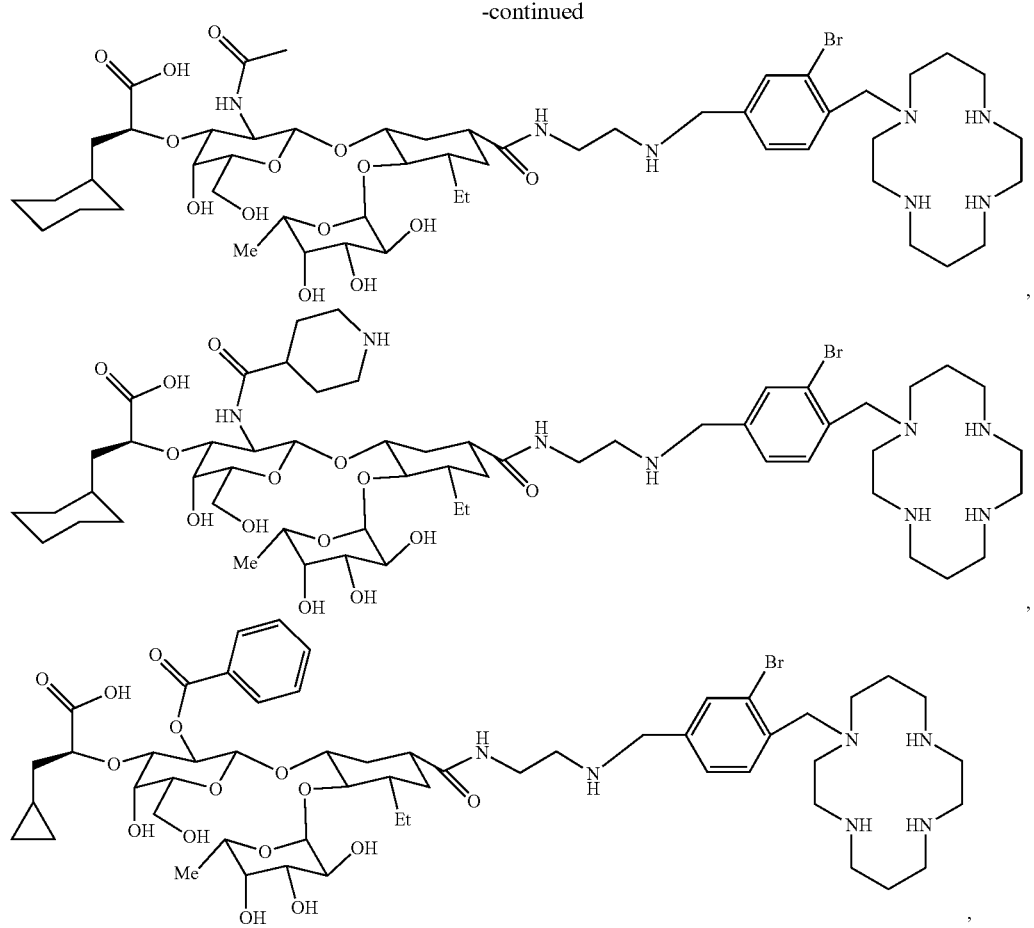
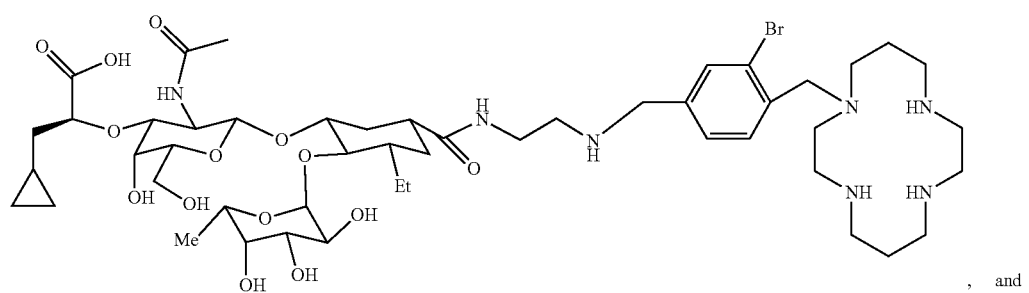
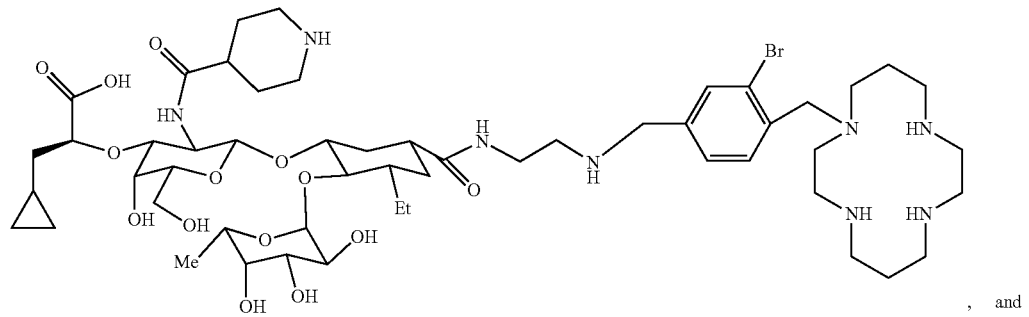
pharmaceutically acceptable salts of any of the foregoing.

12. The method of claim 1, wherein the at least one heterobifunctional inhibitor is chosen from
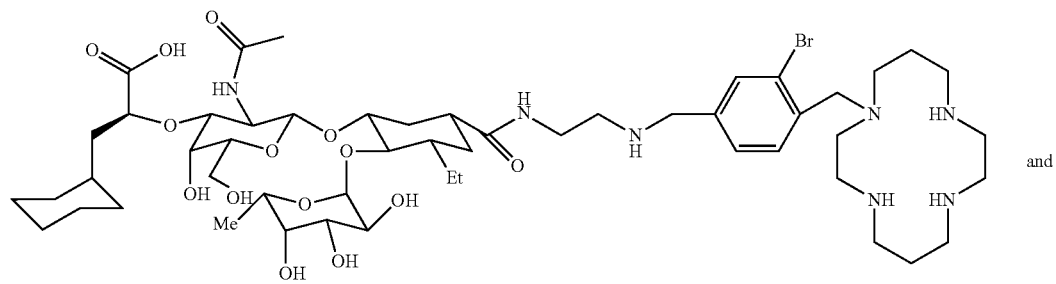 [SMILES: CCC1CC(C(=O)NCCNCc2ccc(CN3CCCNCCNCCCNCC3)c(Br)c2)CC(OC2OC(CO)C(O)C(O[C@@H](CC3CCCCC3)C(=O)O)C2NC(C)=O)C1OC1OC(C)C(O)C(O)C1O] and
pharmaceutically acceptable salts thereof.
* * * * *